US012778762B2

(12) United States Patent
Unis et al.

(10) Patent No.: US 12,778,762 B2
(45) Date of Patent: Nov. 3, 2026

(54) CUSTOMIZED TIBIAL TRAYS, METHODS, AND SYSTEMS FOR KNEE REPLACEMENT

(71) Applicant: ICAHN SCHOOL OF MEDICINE AT MOUNT SINAI, New York, NY (US)

(72) Inventors: Douglas B. Unis, New York, NY (US); Chris Scifert, Austin, TX (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 838 days.

(21) Appl. No.: 17/460,943

(22) Filed: Aug. 30, 2021

(65) Prior Publication Data

US 2021/0386552 A1 Dec. 16, 2021

Related U.S. Application Data

(63) Continuation of application No. PCT/US2020/020279, filed on Feb. 28, 2020.

(Continued)

(51) Int. Cl.

*A61F 2/38* (2006.01)
*A61B 17/15* (2006.01)

(Continued)

(52) U.S. Cl.

CPC ............ *A61F 2/389* (2013.01); *A61B 17/157* (2013.01); *A61B 34/30* (2016.02);

(Continued)

(58) Field of Classification Search

CPC .................. A61F 2/389; A61F 2/30942; A61F 2002/30131; A61F 2002/30948;

(Continued)

(56) References Cited

U.S. PATENT DOCUMENTS 5,122,144 A 6/1992 Bert et al.
5,271,737 A 12/1993 Baldwin et al.

(Continued)

FOREIGN PATENT DOCUMENTS

DE 19705733 8/1998
EP 3930632 1/2022

(Continued)

OTHER PUBLICATIONS

Unis et al., European Examination Report for European Patent Application No. 20763146.6 (published as EP3930632), mailed Sep. 27, 2024, 7 pages, Sep. 27, 2024.

(Continued)

*Primary Examiner* — Yashita Sharma

(74) *Attorney, Agent, or Firm* — HESLIN ROTHENBERG FARLEY & MESITI P.C.

(57) ABSTRACT

A tibial tray for a resurfaced proximal portion of a tibia for a knee replacement for a patient includes, for example, a body having a superior portion, and an inferior tibia-engaging portion having a peripheral inferiorly-extending portion contactable with an underlying cortical bone and/or spaced apart from the underlying inner surface of the cortical of the tibia of the patient. In some embodiments in the total knee replacement, a greater portion of a shearing force acting transversely on the tibial tray and the resected portion of the proximal portion of the tibia of the patient is resisted by the at least one inferiorly-extending wall and the periphery of the resected proximal portion of the tibia compared to a portion of the shearing force being resisted along the center inferior surface of the tibial tray and the resected cancellous bone surface. Methods, robotic systems, and cutting guides are also disclosed.

16 Claims, 35 Drawing Sheets

Related U.S. Application Data

(60) Provisional application No. 62/879,800, filed on Jul. 29, 2019, provisional application No. 62/811,855, filed on Feb. 28, 2019.

(51) Int. Cl.
*A61B 34/30* (2016.01)
*A61F 2/30* (2006.01)

(52) U.S. Cl.
CPC ..................... *A61F 2/30942* (2013.01); *A61F 2002/30131* (2013.01); *A61F 2002/30948* (2013.01); *A61F 2002/30985* (2013.01)

(58) Field of Classification Search
CPC .......... A61F 2002/30985; A61F 2/3859; A61F 2/3877; A61F 2002/30878; A61F 2002/30884; A61F 2002/30891; A61F 2002/30957; A61F 2002/3895; A61F 2/38; A61B 17/157; A61B 34/30; A61B 17/1764
See application file for complete search history.

(56) References Cited

U.S. PATENT DOCUMENTS

| | | | | |
|---|---|---|---|---|
| 5,480,444 | A | 1/1996 | Incavo et al. | |
| 5,486,180 | A | 1/1996 | Dietz et al. | |
| 5,683,471 | A | 11/1997 | Incavo et al. | |
| 6,056,779 | A | 5/2000 | Noyer et al. | |
| 6,966,928 | B2 | 11/2005 | Fell et al. | |
| 7,524,334 | B2 | 4/2009 | Haidukewych | |
| 8,317,870 | B2 | 11/2012 | Wagner et al. | |
| 8,328,874 | B2 | 12/2012 | Lee | |
| 8,690,955 | B2 | 4/2014 | Rolston | |
| 8,771,364 | B2 | 7/2014 | May et al. | |
| 8,900,316 | B2 | 12/2014 | Lenz et al. | |
| 8,906,106 | B2 | 12/2014 | Goodfellow et al. | |
| 9,345,578 | B2 | 5/2016 | Collazo et al. | |
| 9,468,531 | B2 | 10/2016 | Cook et al. | |
| 9,554,912 | B2 | 1/2017 | Goodfellow et al. | |
| 9,636,229 | B2 | 5/2017 | Lang et al. | |
| 9,717,598 | B2 | 8/2017 | Otto | |
| 9,861,372 | B2 | 1/2018 | Servidio | |
| 9,872,773 | B2 | 1/2018 | Lang et al. | |
| 10,052,208 | B2 | 8/2018 | Fell | |
| 10,085,804 | B2 | 10/2018 | Nortman et al. | |
| 10,828,168 | B2 * | 11/2020 | Logan | A61F 2/38 |
| 10,945,848 | B2 | 3/2021 | Unis et al. | |
| 2005/0043809 | A1 | 2/2005 | Ryd | |
| 2005/0125068 | A1 | 6/2005 | Hozack et al. | |
| 2005/0203632 | A1 | 9/2005 | Daniels | |
| 2005/0267353 | A1 | 12/2005 | Marquart et al. | |
| 2006/0178749 | A1 | 8/2006 | Pendleton et al. | |
| 2007/0010890 | A1 | 1/2007 | Collazo | |
| 2007/0203582 | A1 | 8/2007 | Campbell | |
| 2007/0233269 | A1 | 10/2007 | Steines et al. | |
| 2008/0027557 | A1 | 1/2008 | Tuke | |
| 2008/0119939 | A1 | 5/2008 | Termanini | |
| 2009/0228113 | A1 | 9/2009 | Lang et al. | |
| 2010/0100191 | A1 | 4/2010 | May et al. | |
| 2010/0217400 | A1 | 8/2010 | Nortman et al. | |
| 2010/0249941 | A1 | 9/2010 | Fell et al. | |
| 2011/0190898 | A1 * | 8/2011 | Lenz | A61F 2/38 623/20.32 |
| 2014/0243990 | A1 | 8/2014 | Collazo et al. | |
| 2014/0257508 | A1 | 9/2014 | Bojarski et al. | |
| 2014/0277544 | A1 | 9/2014 | Viscogliosi et al. | |
| 2015/0088265 | A1 | 3/2015 | Lenz et al. | |
| 2017/0042684 | A1 * | 2/2017 | Yoo | A61F 2/389 |
| 2017/0119533 | A1 | 5/2017 | Goodfellow et al. | |
| 2017/0216038 | A1 | 8/2017 | Lang et al. | |
| 2017/0231783 | A1 | 8/2017 | Lang et al. | |
| 2017/0360567 | A1 | 12/2017 | Fitz et al. | |
| 2018/0049879 | A1 | 2/2018 | Ingwer et al. | |
| 2018/0235762 | A1 | 8/2018 | Radermacher et al. | |
| 2018/0271665 | A1 | 9/2018 | Lenz et al. | |
| 2018/0325683 | A1 | 11/2018 | Logan et al. | |
| 2019/0029764 | A1 | 1/2019 | Nortman et al. | |
| 2019/0175351 | A1 | 6/2019 | Bojarski et al. | |

FOREIGN PATENT DOCUMENTS

| | | | |
|---|---|---|---|
| EP | 4153096 | A1 | 3/2023 |
| JP | H08275963 | A | 10/1996 |
| JP | 2012505726 | A | 3/2012 |
| JP | 2013517911 | A | 5/2013 |
| WO | 2017177182 | A1 | 10/2017 |
| WO | 2020176824 | A1 | 9/2020 |
| WO | 2021236736 | A1 | 11/2021 |

OTHER PUBLICATIONS

Unis et al., Extended European Search Report for European Application No. 21808537.1 (published as EP4153096), mailed May 10, 2024, 6 pages, May 10, 2024.

Extended European Search Report for European Patent Application No. 20763146.6, 9 pages, Sep. 28, 2022.

International Preliminary Report on Patentability for International Application No. PCT/US2020/020279, Aug. 25, 2021, 19 pages, International Bureau of WIPO.

Unis et al., U.S. Appl. No. 18/057,404, "Customizable Tibial Trays, Methods, and Systems for Knee Replacement", filed Nov. 21, 2022.

Unis et al., International Search Report and Written Opinion for PCT/US20/20279 (published as WO 2020/176824), titled "Customized Tibial Trays, Methods, and Systems for Knee Replacement", 23 pages, dated Jun. 18, 2020.

Zimmer Trabecular Metal Monoblock Tibial Component, available from Zimmer Biomet, Warsaw, Indiana, printout from the Internet on Jul. 25, 2021, https://www.zimmerindia.com/content/dam/zimmer-web/documents/en-US/pdf/medical-professionals/knee/zimmer-trabecular-metal-monoblock-tibial-components-brochure-2.pdf, 4 pages, at least as early as 2007.

Stryker Triathlon Tibial Component, available from Stryker Corporation, Kalamazoo, Michigan, printout from the Internet on Jul. 25, 2021, https://www.stryker.com/us/en/portfolios/orthopaedics/joint-replacement/knee.html, (Wayback Verification Crawl Presence, https://web.archive.org/web/20180118205339/https://www.stryker.com/us/en/portfolios/orthopaedics/joint-replacement/knee.html, dated Jan. 18, 2018), 8 pages, at least as early as Jan. 18, 2018.

Andrew Rubin, Knee Replacement, Jamaica Hospital Medical Center, printout from the Internet on Nov. 20, 2018, https://jamaicahospital.org/newsletter/knee-replacement/?p=1003, 1 page, Jul. 21, 2014.

Gosman et al., Development of Cortical Bone Geometry in the Human Femoral and Tibial Diaphysis. The Anatomical Record, 296(5), pp. 774-787. 2013.

ConforMIS iTotal CR and PS Knee Replacement Systems, available from ConforMIS, Inc., Bedford, Massachusetts, printout from the Internet on Jul. 25, 2021, (Wayback Verification Crawl Presence, https://web.archive.org/web/20180116213443/http://www.conformis.com/customized-knee-implants/products/itotal/, dated Jan. 16, 2018, and https://web.archive.org/web/20171125154506/http://www.conformis.com:80/customized-knee-implants/image-to-implant-process/, dated Nov. 25, 2017, 6 pages, at least as early as Jan. 16, 2018.

Unis et al., International Patent Application No. PCT/US2021/033102, filed May 19, 2021, titled "Customized Tibial Trays, Methods, and Systems for Knee Replacement", 130 pages, May 19, 2021.

Unis et al., International Search Report and Written Opinion for PCT/US21/33102 (published as WO 2021/236763), titled "Customized Tibial Trays, Methods, and Systems for Knee Replacement", 20 pages, dated Oct. 26, 2021.

Study of the Normal Tibia (Hrdlicka) Oct. 1, 31898, American Anthropological Association, 11, 307, 312.

Unis et al., Australian Examination Report for Australian Patent Application No. 2020229371, mailed Oct. 11, 2024, 5 pages, Oct. 11, 2024.

(56) References Cited

OTHER PUBLICATIONS

Unis et al., Canadian Requisition for Candian Patent Application No. 3,131,343, mailed Jul. 16, 2025, 9 pages, Jul. 16, 2024.

* cited by examiner

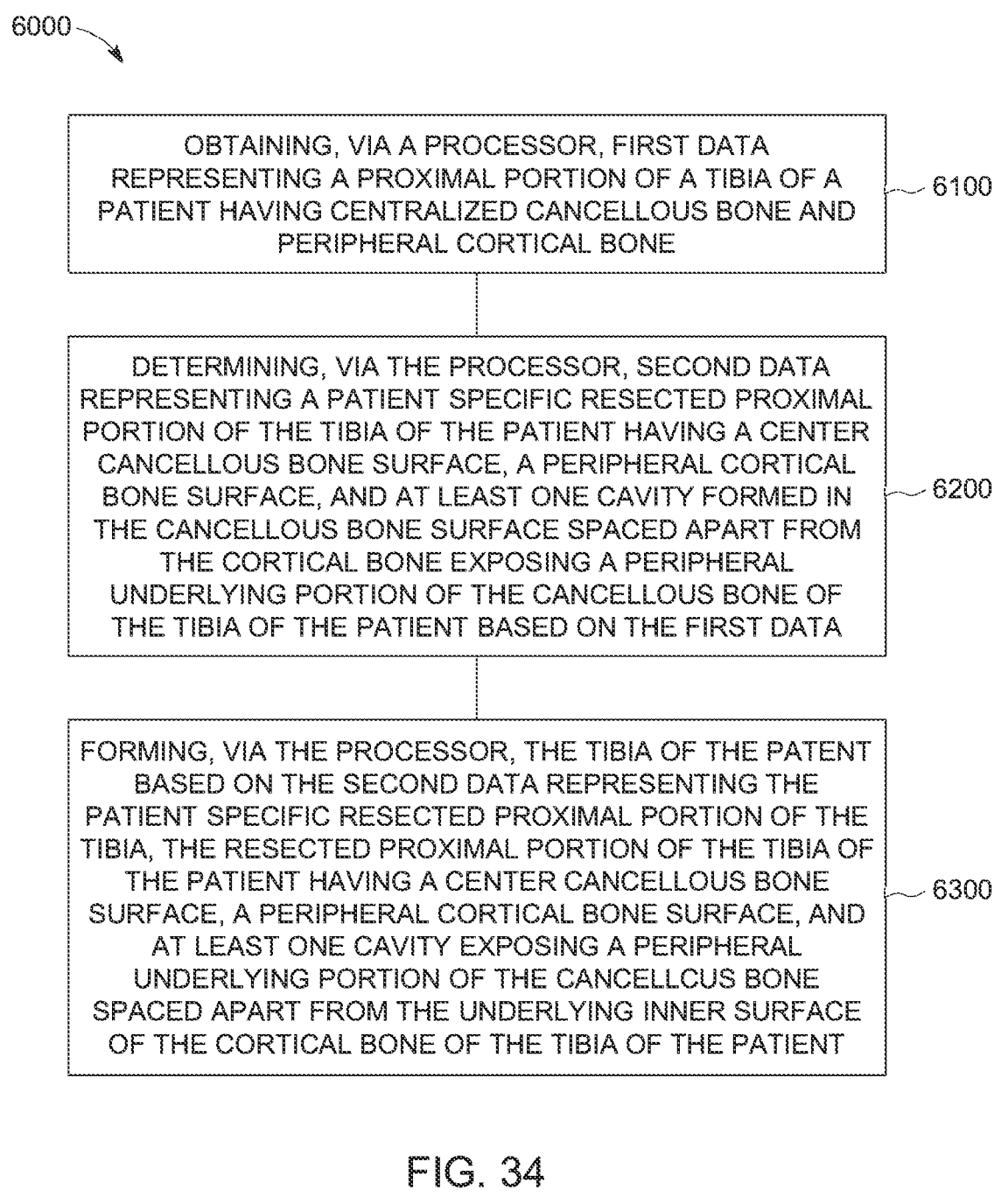

6000

OBTAINING, VIA A PROCESSOR, FIRST DATA REPRESENTING A PROXIMAL PORTION OF A TIBIA OF A PATIENT HAVING CENTRALIZED CANCELLOUS BONE AND PERIPHERAL CORTICAL BONE — 6100

DETERMINING, VIA THE PROCESSOR, SECOND DATA REPRESENTING A PATIENT SPECIFIC RESECTED PROXIMAL PORTION OF THE TIBIA OF THE PATIENT HAVING A CENTER CANCELLOUS BONE SURFACE, A PERIPHERAL CORTICAL BONE SURFACE, AND AT LEAST ONE CAVITY FORMED IN THE CANCELLOUS BONE SURFACE SPACED APART FROM THE CORTICAL BONE EXPOSING A PERIPHERAL UNDERLYING PORTION OF THE CANCELLOUS BONE OF THE TIBIA OF THE PATIENT BASED ON THE FIRST DATA — 6200

FORMING, VIA THE PROCESSOR, THE TIBIA OF THE PATENT BASED ON THE SECOND DATA REPRESENTING THE PATIENT SPECIFIC RESECTED PROXIMAL PORTION OF THE TIBIA, THE RESECTED PROXIMAL PORTION OF THE TIBIA OF THE PATIENT HAVING A CENTER CANCELLOUS BONE SURFACE, A PERIPHERAL CORTICAL BONE SURFACE, AND AT LEAST ONE CAVITY EXPOSING A PERIPHERAL UNDERLYING PORTION OF THE CANCELLCUS BONE SPACED APART FROM THE UNDERLYING INNER SURFACE OF THE CORTICAL BONE OF THE TIBIA OF THE PATIENT — 6300

FIG. 34

CUSTOMIZED TIBIAL TRAYS, METHODS, AND SYSTEMS FOR KNEE REPLACEMENT

CROSS REFERENCE TO RELATED APPLICATIONS

This application is a continuation of International Patent Application No. PCT/US2020/020279, filed on Feb. 28, 2020, entitled "Customized Tibial Trays, Methods, And Systems For Knee Replacement" and published under the PCT Articles in English as WO 2020/176824 on Sep. 3, 2020, which International Patent application claims priority to U.S. Provisional Application No. 62/811,855, filed on Feb. 28, 2019, entitled "Customized Tibial Trays Contactable With An Underlying Cortical Bone, Methods, And Systems For Knee Replacement", and claims priority to U.S. Provisional Application No. 62/879,800, filed Jul. 29, 2019, entitled "Customized Tibial Trays, Methods, And Systems For Knee Replacement", the subject matter of these applications is hereby incorporated herein by reference in their entirety.

FIELD OF THE DISCLOSURE

The present disclosure relates generally to surgical implants, methods, and systems for use in repairing knee joints, and more particularly to patient-specific surgical procedures and customized tibial trays for use in the replacement of knee joints.

BACKGROUND

Typically, the most common indication for revision surgery of Total Knee Arthroplasties is aseptic loosening (29.8%) and subsidence. Aseptic loosening is also a major cause of post-operative pain. These failures are tied to poor osseointegration, imperfect implant coverage, limited support and shear forces introduced by a flat resection plane.

SUMMARY

Shortcomings of the prior art are overcome and additional advantages are provided through the provision, in one embodiment, of a tibial tray for a resection extending transversely across a proximal portion of a tibia of a patient for use in a total knee replacement. The resected proximal portion of the tibia includes a resected cancellous bone surface, a resected peripheral cortical bone surface, and at least one cavity formed in the underlying periphery of the resected cancellous bone. The tibial tray includes a body comprising a superior portion and an inferior tibia-engaging portion. The superior portion includes a superior surface and a peripheral edge. The inferior tibia-engaging portion includes a peripheral inferior surface supportable on the resected peripheral cortical bone surface, a center inferior surface disposable on the resected center cancellous bone surface, and at least one inferiorly-extending wall spaced inwardly from the peripheral inferior surface and extending around at least a portion of the center inferior surface. The at least one inferiorly-extending wall is receivable in the at least one cavity formed in the periphery of the resected cancellous bone surface. The at least one inferiorly-extending wall includes a first U-shaped wall and a spaced apart second U-shaped wall, the at least one inferiorly-extending wall being receivable in the at least one cavity including a first U-shaped cavity and a spaced apart second U-shaped cavity formed in the periphery of the resected cancellous bone surface.

In another embodiment, a method including, for example, resecting a proximal portion of a tibia of a patient, the resected proximal portion of the tibia having a transverse resected cancellous bone surface, a transverse resected peripheral cortical bone surface, and at least one cavity formed in the underlying periphery of the resected cancellous bone, providing a tibial tray having at least one inferiorly-extending wall spaced inwardly from a peripheral edge of the tibial tray and extending around at least a portion of a center inferior surface, inserting the at least one inferiorly-extending wall in the at least one cavity formed in the underlying periphery of the resected cancellous bone surface, and disposing the center inferior surface against the transverse resected cancellous bone surface, wherein in a total knee replacement, a greater portion of a shearing force acting transversely on the tibial tray and the resected portion of the proximal portion of the tibia of the patient is resisted by the at least one inferiorly-extending wall and the periphery of the resected proximal portion of the tibia compared to a portion of the shearing force being resisted along the center inferior surface of the tibial tray and the resected cancellous bone surface.

In another embodiment, a method for forming a patient-specific tibial tray for a total knee replacement of the patient, includes for example, obtaining first data, via at least one processor, representing a proximal portion of the tibia of the patient, the first data corresponding to the proximal portion of the tibia of the patient having an inner cancellous bone, and a peripheral cortical bone having an outer surface and an inner surface, determining, via the at least one processor, second data representing a patient-specific resected proximal portion of the tibia of the patient based on the first data, the resected proximal portion of the tibia of the patient having a center cancellous bone surface, a peripheral cortical bone surface, and at least one cavity formed in the underlying periphery of the resected cancellous bone, the at least one cavity having an outer contoured surface portion corresponding to an adjacent inner surface portion of the resected cortical bone, forming, via the at least one processor, the patient-specific tibial tray based on the second data, the patient-specific tibial tray comprising a body having a superior portion having a superior surface and an inferior tibia-engaging portion, the inferior tibia engaging portion having a center portion contactable with the resected center cancellous bone surface, and at least one inferiorly-extending wall receivable in the at least one cavity, and wherein, in the total knee replacement, a greater portion of a shearing force acting transversely on the patient-specific tibial tray and the resected portion of the proximal portion of the tibia of the patient is resistible by the at least one inferiorly-extending wall and the periphery of the resected proximal portion of the tibia compared to a portion of the shearing force being resistible along the center inferior surface of the tibial tray and the resected cancellous bone surface.

Shortcomings of the prior art are overcome and additional advantages are provided through the provision, in one embodiment, of a tibial tray for a resected proximal portion of a tibia of a patient for a knee replacement. The resected proximal portion of the tibia includes a center cancellous bone surface, a peripheral cortical bone surface, and at least one cavity formed in the cancellous bone exposing at least a portion of an underlying inner surface of the cortical bone. The tibial tray includes a body having a superior portion with a superior surface, and an inferior tibia-engaging portion. The inferior tibia-engaging portion includes a center portion having a center surface contactable with the center cancellous bone surface, and a peripheral, inferiorly-extending portion receivable in the at least one cavity formed in the cancellous bone. A surface of the peripheral inferiorly-extending portion is contactable with the exposed underlying inner surface of the cortical bone of the tibia of the patient.

In another embodiment, a method for forming a patient-specific tibial tray for a knee replacement for the patient includes, for example, determining a patient-specific resected proximal portion of a tibia of the patient, the resected proximal portion of the tibia of the patient having a superior center cancellous bone surface, a peripheral cortical bone surface, and one or more cavities and/or openings in the cancellous bone exposing at least a portion of an underlying inner surface of the cortical bone of the tibia, and forming the patient-specific tibial tray comprising a body having an superior portion with a superior surface and an inferior tibia-engaging portion, the inferior tibia engaging portion having a center portion contactable with the cancellous bone surface, and a peripheral, inferiorly-extending portion receivable in the one or more cavities and/or openings and having one or more surfaces contactable with the exposed underlying inner surface of the cortical bone of the tibia of the patient.

In another embodiment, a robotic method for resecting a proximal portion of a tibia of a patient for a knee replacement includes, for example, obtaining, via a processor, first data representing a proximal portion of the tibia of the patient comprising centralized cancellous bone and peripheral cortical bone, determining, via the processor, second data of a patient-specific resected proximal portion of the tibia of the patient having a center cancellous bone surface, a peripheral cortical bone surface, and at least one cavity formed in the cancellous bone exposing at least a portion of an underlying inner surface of the cortical bone based on the first data, and forming, via the processor, the tibia of the patent based on the second data of the patient-specific resected proximal portion of the tibia, the resected proximal portion of the tibia of the patient having the center cancellous bone surface, a peripheral cortical bone surface, and the at least one cavity exposing the inner surface of the cortical bone of the tibia.

Shortcomings of the prior art are also overcome and additional advantages are provided through the provision, in one embodiment, of a tibial tray for a resected proximal portion of a tibia of a patient for a total knee replacement. The resected proximal portion of the tibia includes a center cancellous bone surface, a peripheral cortical bone surface, and at least one cavity formed in the periphery of the cancellous bone which is spaced apart from the cortical bone exposing an underlying portion of the cancellous bone of the tibia. The tibial tray includes a body having a superior portion with a superior surface, and an inferior tibia-engaging portion. The inferior tibia-engaging portion includes a center portion having a center surface contactable with the center cancellous bone surface, and a peripheral, inferiorly-extending portion receivable in the at least one cavity formed in the cancellous bone surface so that the peripheral inferiorly-extending portion is spaced apart from the underlying inner surface of the cortical bone of the tibia of the patient.

In another embodiment, a method for forming a patient-specific tibial tray for a total knee replacement for the patient includes, for example, determining a patient-specific resected proximal portion of a tibia of the patient, the resected proximal portion of the tibia of the patient having a superior center cancellous bone surface, a peripheral cortical bone surface, and at least one cavity formed in the periphery of the cancellous bone exposing an underlying portion of the cancellous bone of the tibia, and forming the patient-specific tibial tray comprising a body having a superior portion with a superior surface and an inferior tibia-engaging portion, the inferior tibia engaging portion having a center portion contactable with the center cancellous bone surface, and a peripheral, inferiorly-extending portion receivable in the at least one cavity so that the peripheral inferiorly-extending portion is spaced apart from the exposed underlying inner surface of the cortical bone of the tibia of the patient.

In another embodiment, a robotic method for resecting a proximal portion of a tibia of a patient for a total knee replacement includes, for example, obtaining, via a processor, first data representing a proximal portion of the tibia of the patient comprising centralized cancellous bone and peripheral cortical bone, determining, via the processor, second data of a patient-specific resected proximal portion of the tibia of the patient having a center cancellous bone surface, a peripheral cortical bone surface, and at least one cavity formed in the periphery of the cancellous bone spaced apart from the cortical bone exposing an underlying portion of the cancellous bone based on the first data, and forming, via the processor, the tibia of the patent based on the second data representing the patient-specific resected proximal portion of the tibia, the resected proximal portion of the tibia of the patient having a center cancellous bone surface, a peripheral cortical bone surface, and at least one cavity formed in the periphery of the cancellous bone spaced apart from the cortical bone exposing an underlying portion of the cancellous bone of the tibia.

Shortcomings of the prior art are also overcome and additional advantages are provided through the provision, in one embodiment, of a tibial tray for a resected proximal portion of a tibia of a patient for a total knee replacement. The resected proximal portion of the tibia includes a center cancellous bone surface, a peripheral cortical bone surface, and at least one cavity formed in the periphery of the cancellous bone which is spaced apart from the cortical bone exposing an underlying portion of the cancellous bone of the tibia. The tibial tray includes a body having a superior portion with a superior surface, and an inferior tibia-engaging portion. The inferior tibia-engaging portion includes a center portion having a center surface contactable with the center cancellous bone surface, and a peripheral, inferiorly-extending portion receivable in the at least one cavity formed in the cancellous bone surface so that the peripheral inferiorly-extending outer surface portion corresponds to the contour of the underlying inner surface of the cortical bone of the tibia of the patient. In other embodiments, the peripheral, inferiorly-extending portion includes at least a portion of the peripheral inferiorly-extending outer surface portion extending from a proximal portion of the peripheral, inferiorly-extending portion to a distal portion of the peripheral, inferiorly-extending portion contoured to correspond to a contour of a superior edge portion of the cortical bone along the resection plane so that the at least the portion of the peripheral inferiorly-extending outer surface portion is disposable adjacent to a underlying concave inner surface of the cortical bone.

Shortcomings of the prior art are also overcome and additional advantages are provided through the provision, in one embodiment, of a tibial tray for a resected medial or lateral proximal portion of a tibia of a patient for a partial knee replacement, The resected medial or lateral proximal portion of the tibia has a central cancellous bone surface, a partial peripheral cortical bone surface, and at least one cavity formed in the periphery of the cancellous bone in the resected medial or lateral proximal portion of the tibia. The tibial tray includes a body having a superior portion with a superior surface, and an inferior tibia-engaging portion. The inferior tibia-engaging portion includes a center portion having a center surface contactable with the resected central cancellous bone surface, and a peripheral, inferiorly-extending portion receivable in the at least one cavity formed in the resected cancellous bone surface so that the peripheral inferiorly-extending outer surface portion corresponds to the contour of the underlying inner surface of the cortical bone of the tibia of the patient.

Shortcomings of the prior art are also overcome and additional advantages are provided through the provision, in one embodiment, of a cutting guide for forming at least one cavity in a resected proximal portion of a tibia of a patient for knee replacement. The resected proximal portion of the tibia has a center cancellous bone surface and a peripheral cortical bone surface. The cutting guide includes a planar member having a first planar surface and a second planar surface. The planar member has a peripheral outer edge, a portion of which corresponding to at least a portion of an outer peripheral cortical bone along the resection of the proximal portion of the tibial of the patient, and at least one U-shaped opening extending through the planar member from the first planar surface to the second planar surface and spaced from the peripheral outer edge. The U-shaped opening defines a U-shaped axis, and the U-shaped opening has a constant width normal to the U-shape axis. The U-shaped opening has an inner edge and an outer edge, and the outer edge being parallel to the peripheral outer edge. The cutting guide can further include a milling tool having a proximal diameter sized larger than the width of the opening, and a distal diameter sized for passing through the opening.

Shortcomings of the prior art are also overcome and additional advantages are provided through the provision, in one embodiment, a cutting guide for forming a pair of cavities in a resected proximal portion of a tibia of a patient for total knee replacement, the resected proximal portion of the tibia having a center cancellous bone surface and a peripheral cortical bone surface. The cutting guide includes a planar member having a first planar surface and a second planar surface. The planar member includes a peripheral outer edge corresponding to an outer peripheral cortical bone along the resection of the proximal portion of the tibial of the patient. A pair of U-shaped openings extend through the planar member from the first planar surface to the second planar surface and spaced from the peripheral outer edge. Each of the pair of U-shaped openings define a U-shaped axis, and the U-shaped opening has a constant width normal to the U-shape axis. Each of the pair of the U-shaped openings having an inner edge and an outer edge, and the outer edge is parallel to the peripheral outer edge. The cutting guide can further include a milling tool having a proximal diameter sized larger than the width of opening, and a distal diameter sized for passing through the opening.

BRIEF DESCRIPTION OF THE DRAWINGS

The subject matter which is regarded as the disclosure is particularly pointed out and distinctly claimed in the concluding portion of the specification. The disclosure, however, may best be understood by reference to the following detailed description of various embodiments and the accompanying drawings in which:

FIG. 34 is a flowchart of a robotic process for repairing a knee joint of a patient, according to an embodiment of the present disclosure;

DETAILED DESCRIPTION

Generally stated, disclosed herein are resected proximal portions of tibias, tibial trays, and methods and robotic systems for forming the same.

In this detailed description and the following claims, the words proximal, distal, anterior, posterior, medial, lateral, superior, and inferior are defined by their standard usage for indicating a particular part of a bone or implant according to the relative disposition of the natural bone or directional terms of reference.

Positions or directions may be used herein with reference to anatomical structures or surfaces. For example, as the current devices and methods are described herein with reference to use with the bones of the knee, the bones of the knee may be used to describe the surfaces, positions, directions or orientations of the tibial trays, tibial tray installation, and surgical methods. Further, the devices and surgical methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices and surgical methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the apparatus and surgical methods, and the aspects, components, features and the like thereof, described herein with respect to a left knee may be mirrored so that they likewise function with a right knee and vice versa.

Figure 6:
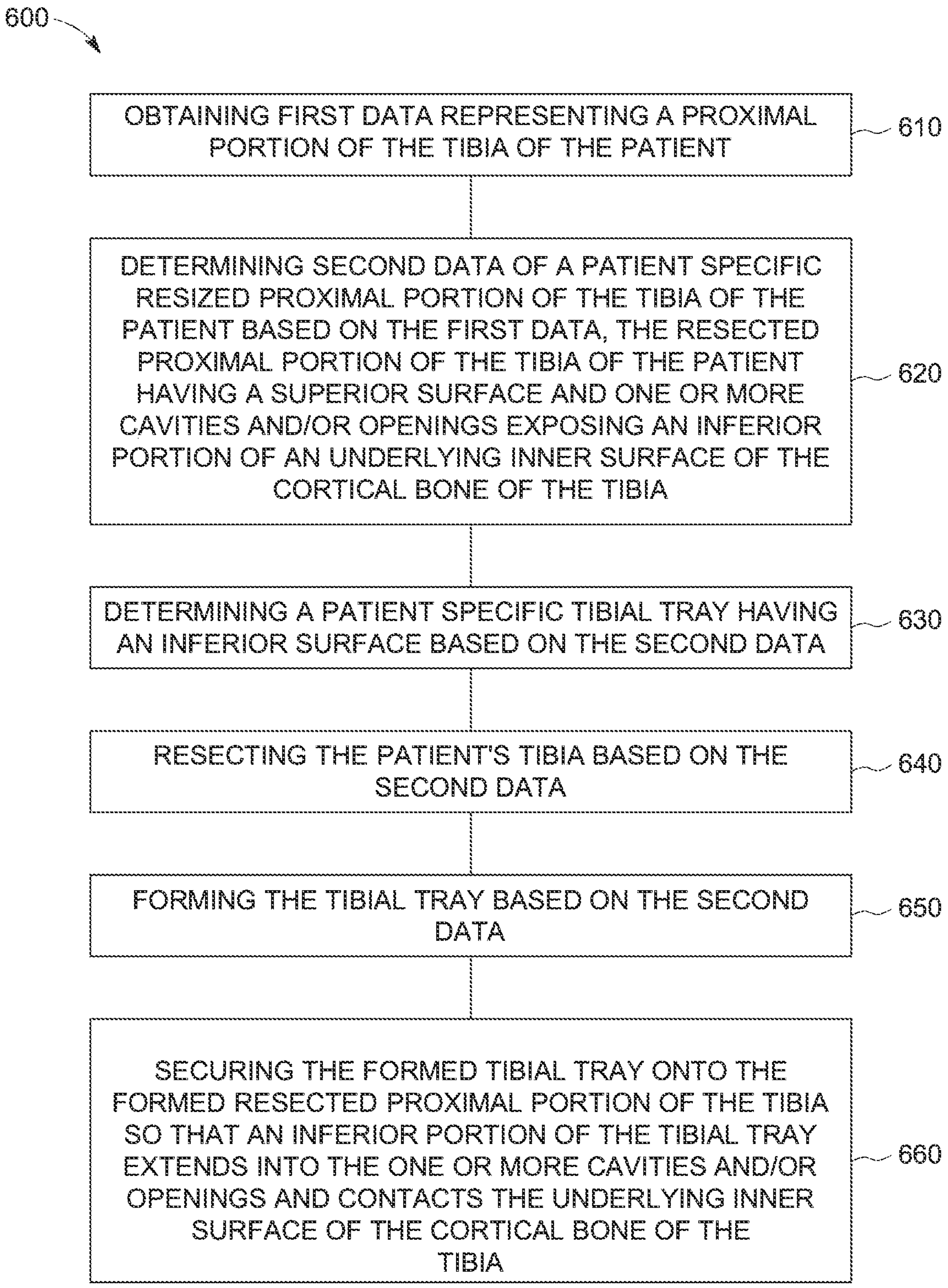
FIG. 6 is a flowchart of a process for repairing a knee joint of a patient, according to an embodiment of the present disclosure.
Figure 7:
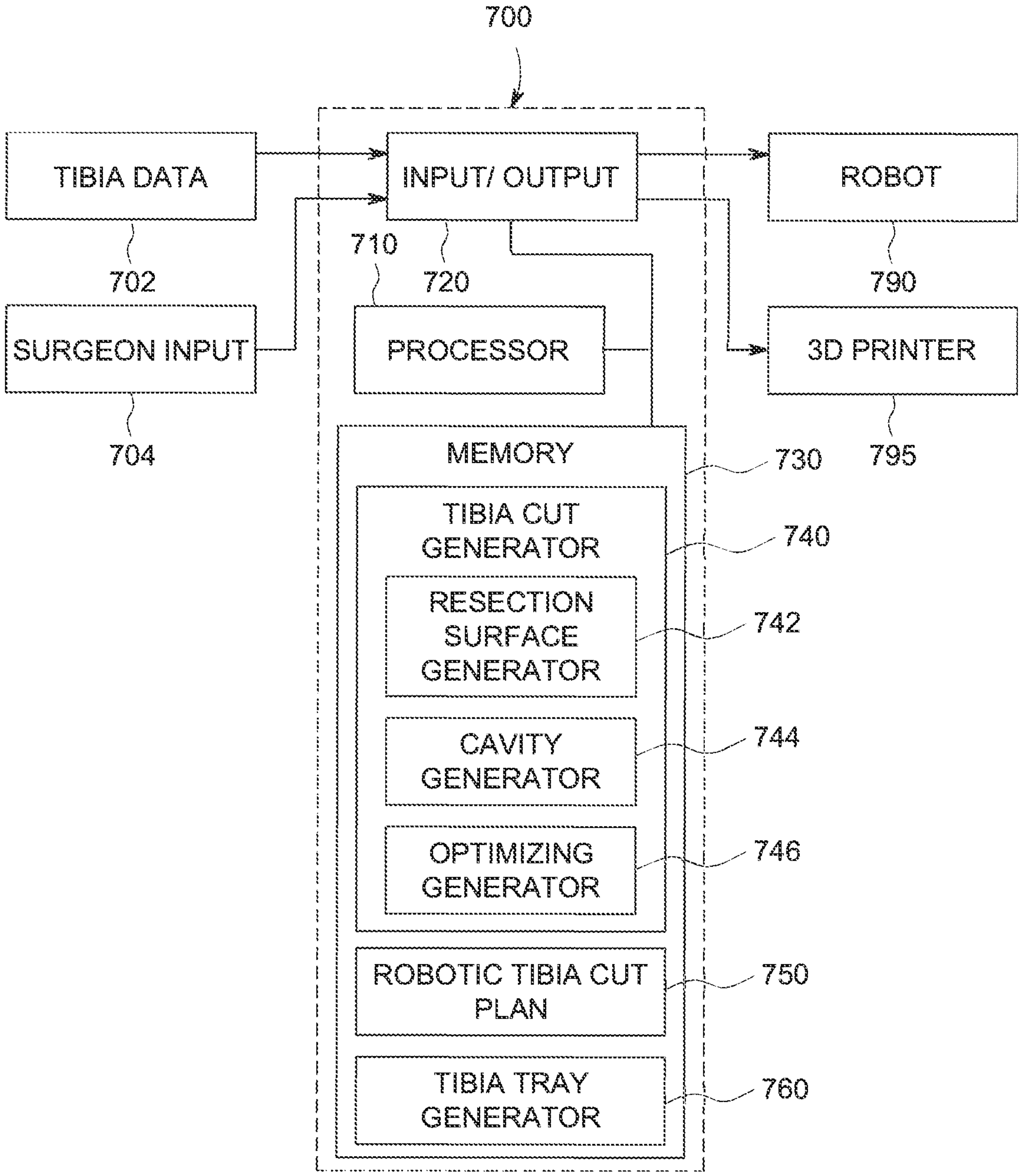
FIG. 7 is a block diagram of a system for repairing a knee joint of a patient, according to an embodiment of the present disclosure.
Figure 33:
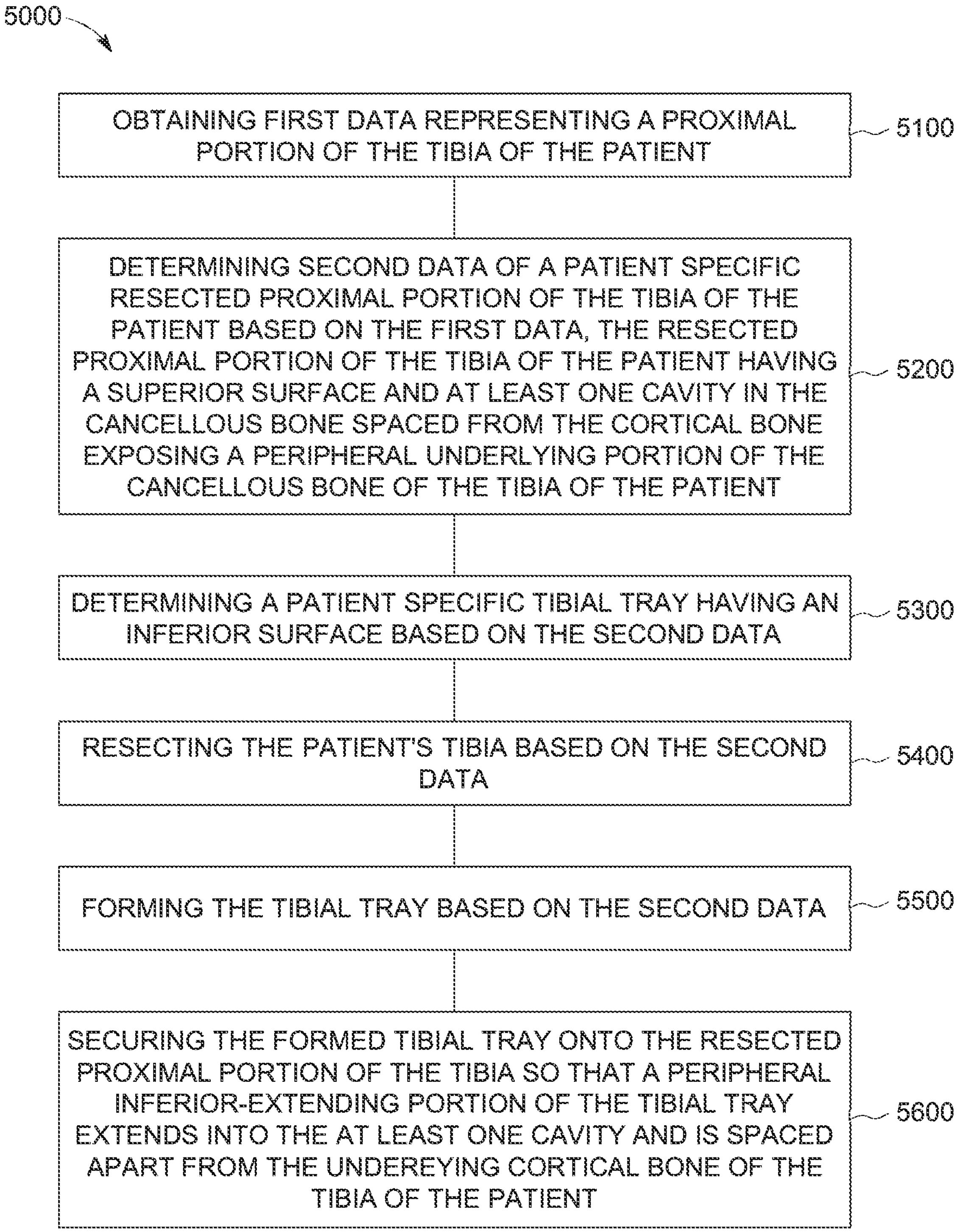
FIG. 33 is a flowchart of a process for repairing a knee joint of a patient, according to an embodiment of the present disclosure.

Referring to the drawings, wherein like reference numerals are used to indicate like or analogous components throughout the several views, and with particular reference to, for example, FIGS. 1, 3, 4, 12-14, 15-21, 22 and 23, 24, and 25 therein illustrated are exemplary embodiments of tibial trays installed on a resected proximal portion of a tibia in which portions of the tibial tray are engageable and/or contactable with an underlying inner surface of the cortical bone for use in a knee replacement. As will be appreciated from the description below, the hard cortical bone of the tibia may provide fixation such as press fitting into this dense bone versus conventional tibial trays which rest on top of the hard cortical bone with a keel in the center in the softer cancellous bone. For example, the present disclosure may result in improved fixation of uncemented tibial trays. FIG. 6 illustrates a method for use in knee replacement surgery, and FIG. 7 illustrates a system for effecting the resecting of the proximal portion of a tibia of a patient and for forming a corresponding, orientated, or matching tibial tray. The methods and systems may be operable for obtaining fully autonomous and automatic resected proximal tibias and corresponding tibial trays from, for example, CT scan data. With reference to FIGS. 26-30, therein illustrated are exemplary embodiments of tibial trays installed on a resected proximal portion of a tibia in which portions of the tibial tray are spaced from and disposed closely adjacent to an underlying inner surface of the cortical bone for use in a knee replacement. As will be appreciated from the description below, the peripheral cancellous bone adjacent to the cortical bone of the tibia may provide fixation to the proximal tibia versus conventional tibial trays which rest on top of the cortical bone with a keel disposed in the center of the softer cancellous bone. For example, the present disclosure may result an in improved fixation of uncemented tibial trays. FIG. 33 illustrates a method for use in knee replacement surgery, for example employing the tibial trays of FIGS. 26-30, which includes effecting the resecting of the proximal portion of a tibia of a patient, and for forming a corresponding, orientated, or matching tibial tray. FIG. 34 illustrates a robotic method for use in knee replacement surgery, which includes effecting the resecting of the proximal portion of a tibia of a patient. The methods and systems may be operable for obtaining fully autonomous and automatic resected proximal tibias and corresponding tibial trays from, for example, CT scan data.

In some embodiments, for example, a patient-specific tibial tray design may mitigate aseptic loosening and subsidence through a combination of high peripheral surface area contact, underside surface geometry, and patient matched pegs that interface with cortical metaphyseal bone. The present disclosure may solve and/or overcome a primary cause for knee implant failure, namely, aseptic loosening of the tibial component and subsidence.

In some embodiments, the present disclosure is directed to methods for generating a three-dimensional model of a tibia and generating a cut plan for excavating a portion of the tibia with a robot or robotic excavator according to the cut plan to allow for the insertion of a custom tibial tray designed to increase or maximize cortical contact with the periphery of the inner tibial wall.

In some embodiments, a technique of the present disclosure is directed to maximizing cortical contact of a tibial tray along the underlying inner surface of the cortical wall of the tibia. A virtual model of the proximal portion of a tibia bone may be used to determine an improved implant that is designed to achieve a higher level of cortical contact. A processor may be employed and configured to generate an excavation protocol for excavating bone from the tibia such that the amount of bone contact between the bone and the implant is increased, such as 10 percent or greater, compared to convention tibial trays.

Figure 1:
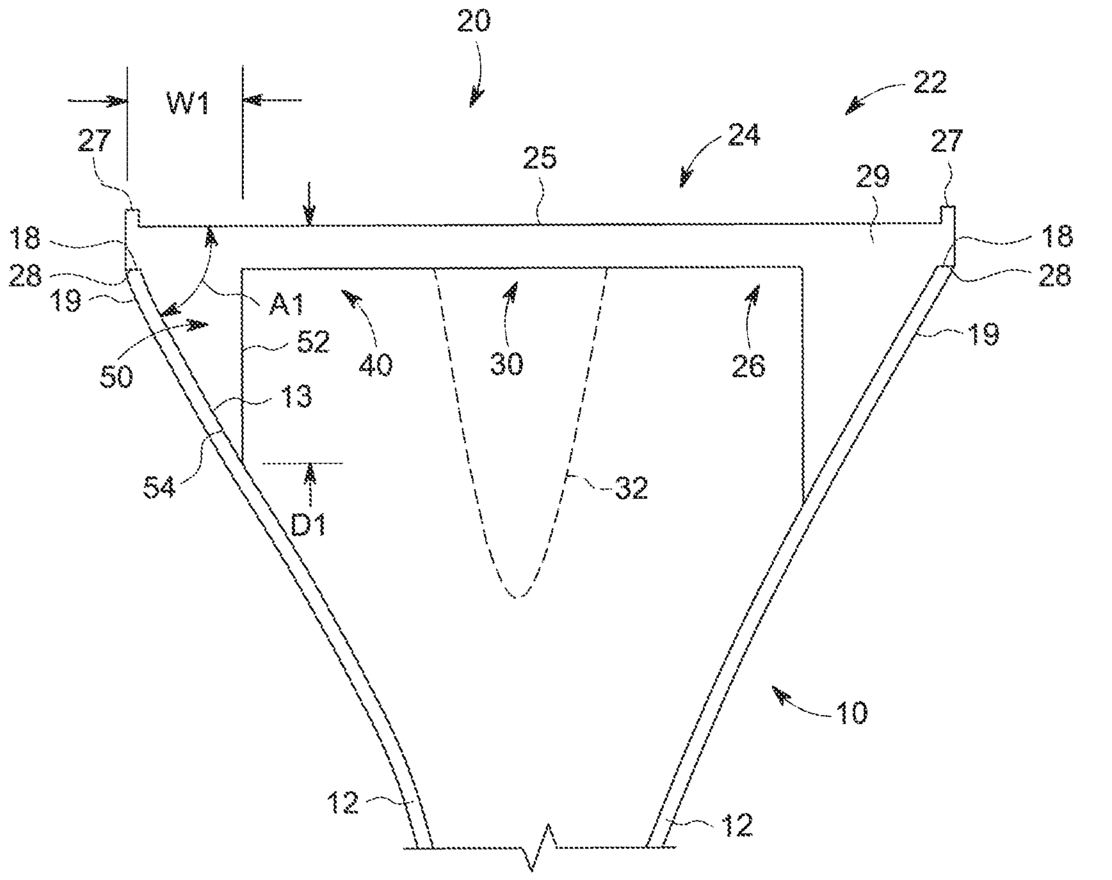
FIG. 1 is a frontal cross-sectional view of a resected proximal portion of a tibia of a patient and a tibial tray, according to an embodiment of the present disclosure.

FIG. 1 illustrates a tibial tray 20 fitted to a resected proximal portion of a tibia 10 for a knee replacement, according to an embodiment of the present disclosure. In this illustrated embodiment, at least a portion of the tibial tray 20 when operably attached to the resected proximal portion of the tibia 10 interfaces and increases contact with an inner surface or side portion of the cortical bone 12 of the proximal portion of the tibia 10.

For example, the tibial tray 20 may include a body 22 having a superior portion 24 and an inferior tibia-engaging portion 26. The superior portion 24 may include a generally planar superior surface 25 for supporting a plastic bearing spacer (not shown in FIG. 1). In some embodiments, the surface 25 includes a peripheral upwardly-extending lip 27 for attaching via a typical snap fit connection and restraining the plastic bearing spacer.

The tibia engaging portion 26 may include a center tibia engaging portion 30 and a peripheral tibia engaging portion 40. In this embodiment, the center tibia engaging portion 30 may include a planar surface contactable with the center cancellous bone surface of the resected proximal portion of the tibia of the patient.

The peripheral tibia-engaging portion 40 may include at least one inferiorly-extending wall 50. The inferiorly-extending wall 50 may include an inner wall surface 52 and an outer wall surface 54. The inner wall surface 52 may be disposed normal or at 90 degrees to the superior surface 25, or at any suitable angle or angles. The outer wall surface 54 may be able to be aligned with and abutting or contacting an inner surface 13 of the cortical bone 12.

For example, the outer wall surface 54 may be disposed at an angle A1, which may be angled at about 25 degrees to about 45 degrees, about 30 degrees to about 40 degrees, about 35 degrees, or other suitable angles relative to the superior surface 25 of the tibial tray 20. The wall 50 is received in a cavity formed in the resected proximal portion of the tibia 10. The cavity may be formed in the cancellous bone, trabecular bone, spongy bone, or light porous bone of the tibia. The wall may increase the contact area with the inner surface 13 of the cortical bone 12. A depth D1 of the wall 50 may extend about 0.5 millimeters (mm) to about 75 mm, about 1 mm to about 50 mm, about 2 mm to about 40 mm, about 4 mm to about 20 mm, exceed 0.5 mm, about 1 mm, about 2 mm, about 3 mm, about 5 mm, about 7 mm, or other suitable depths. In some embodiments, the inferiorly-extending wall 50 may extend along at least 25 percent of the periphery of the body 22, along at least 50 percent of the periphery of the body 22, extend along the entire periphery of the body 22, or extend along another suitable amount along the periphery of the body 22. The width W1 of the wall 50 may be about 5 mm to about 6 mm and is desirably greater than about 0.5 mm and less than about 50 mm. In some embodiments, the peripheral edge 29 of the tibial tray 20 may include a lower surface 28 that extends over the superior cut cortical bone 19, e.g., edge 18. In some embodiments, the tibial tray 20 may feature a keel 32 (shown in dashed lines in FIG. 1) and support pins (not shown in FIG. 1). The access cavity in the proximal portion of the tibia and the tibial tray may be sized and formed manually by a surgeon or as described below, prepared automatically or fully automatically by a robot.

Figure 2:
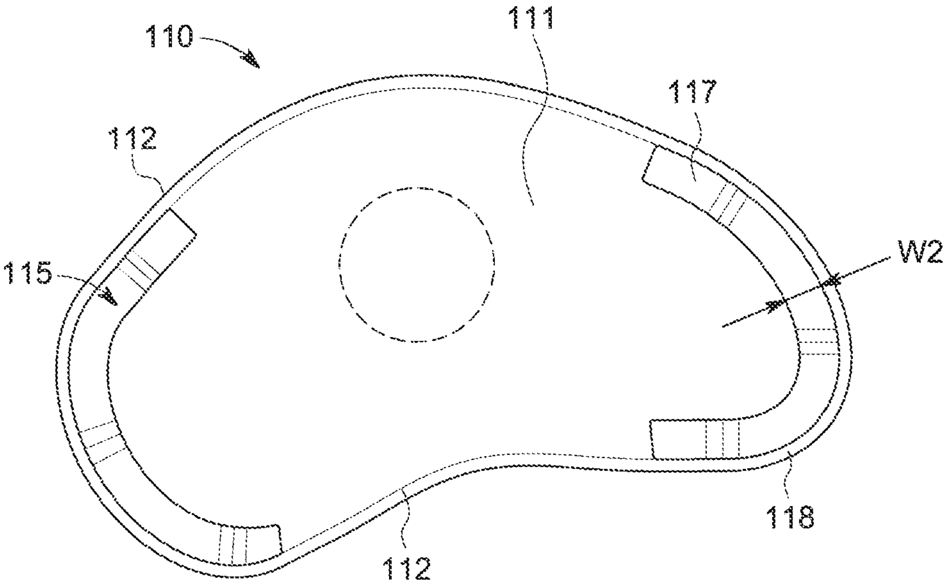
FIG. 2 is a superior view of a resected proximal portion of a tibia of a patient, according to an embodiment of the present disclosure.

FIG. 2 illustrates a superior view of a resected proximal portion of a tibia 110 of a patient for a knee replacement, according to an embodiment of the present disclosure. In this illustrated embodiment, the resected proximal portion of the tibia 110 may include a center cancellous surface 111, and a cortical bone edge surface 118, a first U-shaped cavity 115 disposed along one side of the proximal portion of the tibia 110, and a second U-shaped cavity 117 disposed along an opposite side of the proximal portion of the tibia 110. The cavities 115 and 117 may extend into the cancellous bone, trabecular bone, spongy bone, or light porous bone of the proximal portion of the tibia 110 adjacent to the inner surface of the cortical bone 112 of the proximal portion of the tibia 110. A depth of the cavity may extend about 0.5 millimeters (mm) to about 75 mm, about 1 mm to about 50 mm, about 2 mm to about 40 mm, about 4 mm to about 20 mm, about 1 mm, about 2 mm, about 3 mm, about 5 mm, about 7 mm, or other suitable depth. The width W2 of the wall may be about 5 mm to about 6 mm and is desirably greater than about 0.5 mm and less than about 50 mm. A corresponding tibial tray (not shown in FIG. 2) may have a peripheral edge portion of the tibial tray designed such that the outer edge portion approximates the shape of the tibial edge portion along a resection plane parallel to the tibial tray. As described in greater detail below, the proximal portion of the tibia may be resected or resurfaced manually or robotically such as fully automatically to receive a corresponding tibial tray.

Figure 3:
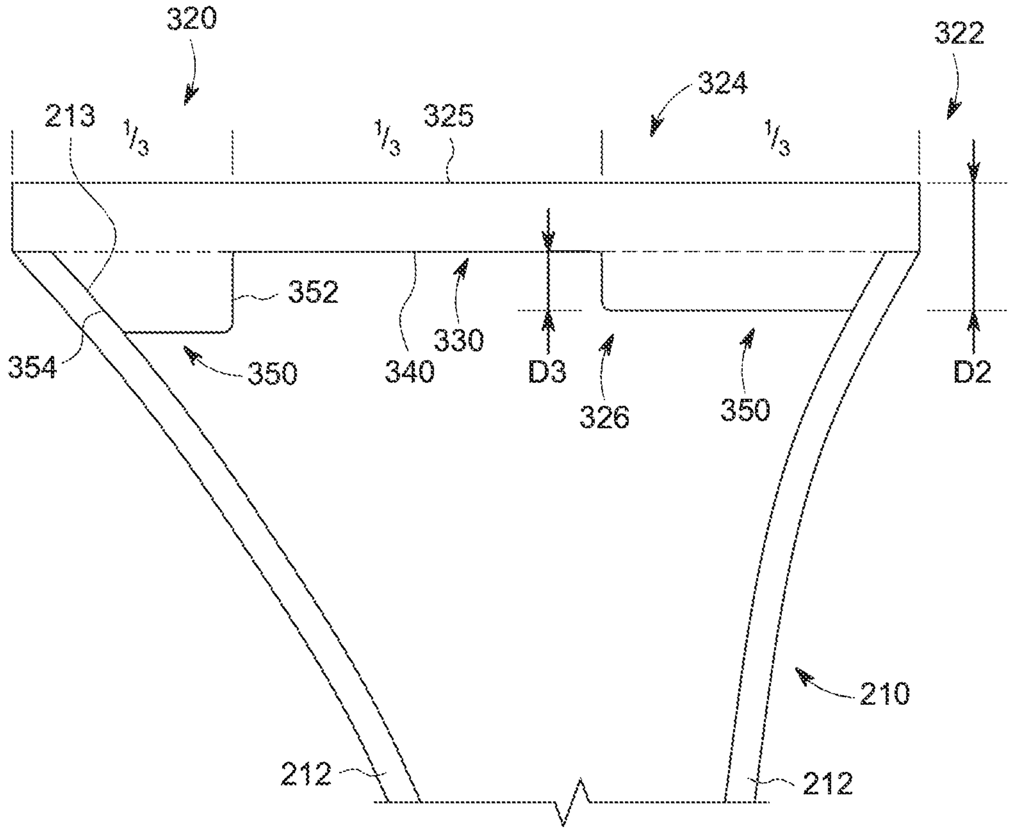
FIG. 3 is a frontal cross-sectional view of a resected proximal portion of a tibia of a patient and a tibial tray, according to an embodiment of the present disclosure.

FIG. 3 illustrates a tibial tray 320 fitted to a resected proximal portion of a tibia 210 for a knee replacement, according to an embodiment of the present disclosure. In this illustrated embodiment, at least a portion of the tibial tray 320 when operably attached to the resected proximal portion of the tibia 210 interfaces and increases the contact area with an inner side portion of the cortical bone 212 of the proximal portion of the tibia 210.

The tibial tray 320 may include a body 322 having a superior portion 324 and an inferior tibia-engaging portion 326. A superior surface 325 of the superior portion 324 may be a generally planar surface for supporting a plastic bearing spacer (not shown in FIG. 3). In some embodiments, the superior surface include a peripherally-extending lip for securing the plastic bearing spacer.

The tibia engaging portion 326 may include a tibia engaging center portion 330 defining a recess 340 relative to a peripheral tibia-engaging portion 350. The peripheral tibia-engaging portion 350 may be a wall or a flat portion disposed around some or all of the tibia engaging center portion 330 and at an elevation different than the tibia engaging center portion 330. The peripheral tibia-engaging portion 350 may be disposed in a cavity formed in the cancellous bone, trabecular bone, spongy bone, or light porous bone of the proximal portion of the tibia adjacent to the inner surface of the cortical bone of the proximal portion of the tibia. The peripheral tibia-engaging portion 350 may include an inner wall surface 352 and an outer wall surface 354. The inner wall surface 352 may be disposed normal or at 90 degrees to the superior surface 325 of the superior portion 324. The outer wall surface 354 may be able to be aligned with and abutting to an inner side surface 213 of the inner surface of the cortical bone 212. A depth D2 of the peripheral tibia-engaging portion 350 may exceed 0.5 mm and may not exceed 75 mm. The geometric resurfacing of the proximal portion of the tibia may result in the superior and inferior portions along a resection plane (excluding a keel and pins) having a depth D3 greater than about 0.5 mm and less than about 15 mm. In some embodiments, a tibial tray may feature a keel and support pins. As described in greater detail below, the proximal portion of the tibia 210 may be resected manually or robotically to receive the corresponding manually or robotically formed tibial tray 320.

Figure 4:
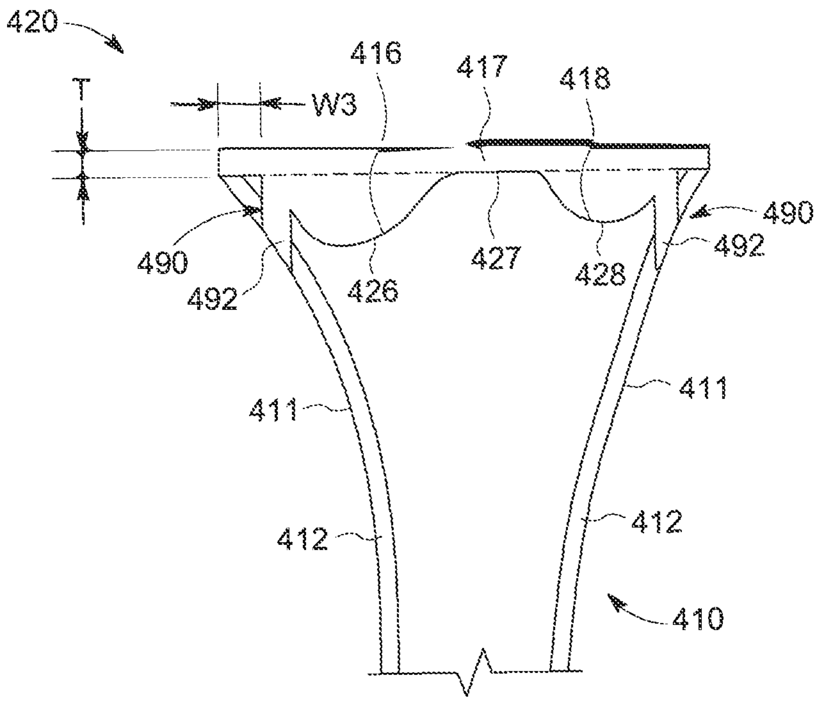
FIG. 4 is a frontal cross-sectional view of a resected proximal portion of a tibia of a patient and a tibial tray, according to an embodiment of the present disclosure.

FIG. 4 illustrates a tibial tray 420 fitted to a resected proximal portion of the tibia 410 for a knee replacement, according to an embodiment of the present disclosure. In this illustrated embodiment, the tibial tray 420 is designed to interface with curved surface geometries and support cavities of the resected proximal portion of the tibia 410.

For example, a typical proximal portion of the tibia bone may feature a concave minimum near the lateral condyle, a convex maximum near the intercondyle eminence, and a concave minimum near the medial condyle. The resected proximal portion of the tibia 410 for a knee replacement of the present disclosure may remove the damaged bone from the proximal portion of the tibia while shaping the bone to include a similar general contour of a typical tibia bone. The resurfaced proximal portion of the tibia bone 410 may feature a concave minimum 416 near the lateral condyle, a convex maximum 417 near the intercondyle eminence, and a concave minimum 418 near the medial condyle. The concave minimum 416, the convex maximum 417, and/or the concave minimum 418 may extend into the cancellous bone, trabecular bone, spongy bone, or light porous bone of the proximal portion of the tibia, which lateral portions of the concave minimum 416, the convex maximum 417, and the concave minimum 418 may be disposed adjacent to and/or in contact with the underlying inner surface of the cortical bone 412 of the proximal portion of the tibia 410. The tibial tray 420 may include an inferior tibia-engaging portion having an inferior convex surface 426, an inferior convex surface 428, and an inferior concave surface 427 disposed therebetween. The radius of the concave surfaces and the radius of the convex surface may be constant radiuses or have varying curvature. The outer edges of the convex surfaces, when viewed from below, may have an oval or a generally egg-shaped configuration.

Figure 5:
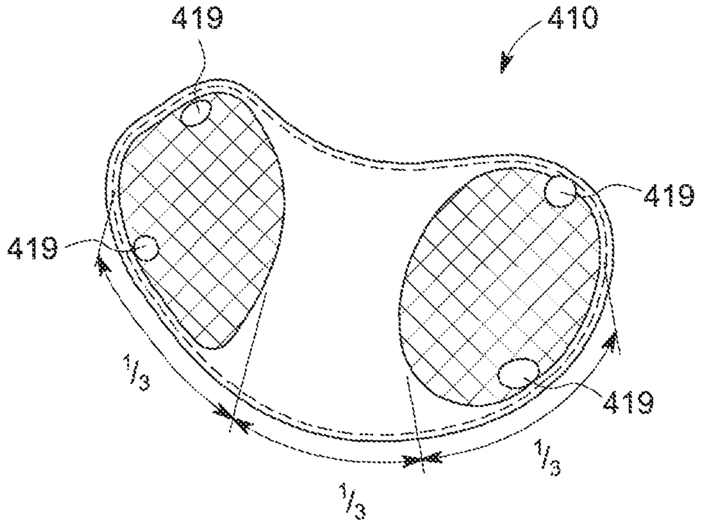
FIG. 5 is a superior view of a resected proximal portion of a tibia of a patient, according to an embodiment of the present disclosure.

The tibial tray 420 may include one or more pins 490 designed to interface with the underlying cortical bone 412. For example, as shown in FIG. 5, an array of four holes 419 may be located in each quadrant of the resected proximal portion of the tibia 410, which holes 419 receive pins 490 (FIG. 4). With reference again to FIG. 4, a bottom portion of the pins 490 may include an outer cylindrical portion that engages the sides of an opening in the cortical bone 412. Such contact area may be with the sides of the opening extending through the cortical bone, including contacting inner edge portions of the openings of the cortical bone, and/or the inner surfaces or surface portions of the cortical bone around the opening in the inner surface of the cortical bone. An inferior edge 492 of the pins 490 may be aligned with the outer surface 411 of the cortical bone 412. The periphery of the tibial tray 420 may define a shelf or lip having a thickness T, for example, of about 4 mm and a width W3 of about 2 mm.

The presently disclosed tibial trays may be operable with conventional plastic spacers and femoral components. For example, the superior surface of the presently disclosed tribal trays may include a surface having a general symmetrical or kidney bean shape designed for engagement with a standard plastic spacer component such as in a snap fit manner. A tibial tray with a variable thickness (by way of nonlimiting example, a rim) may exist at the periphery of the tibial tray such that tibial tray coverage is maximized along the resection plane, but such that engagement of a plastic spacer component is not compromised. The thickness of the tibial rim may be about 4 mm. In another embodiment the rim may exceed about 0.5 mm and be less than about 25 mm.

The tibial trays of the present disclosures may include a one-piece, monolithic, or integral body, or may be formed from two or more components. The tibial tray may be made out of a standard metallic implant material, such as titanium, cobalt chrome, or other acceptable stainless steels. In other embodiments, the tibial tray may of the present disclosure may be made out of a plastic or polymeric material.

FIG. 6 illustrates a method 600 for use in knee replacement surgery, according to an embodiment of the present disclosure. In this illustrated embodiment, the method 600 is operable in providing a customized cut plan of the proximal portion of the tibia for a patient and providing a corresponding customized tibial tray.

The method 600 may include, for example, at 610 obtaining first data representing a proximal portion of the tibia of the patient. At 620, second data of a patient-specific resected proximal portion of the tibia of the patient is determined based on the first data. The resected proximal portion of the tibia of the patient has a superior surface and one or more cavities or openings exposing an inferior portion of an underlying inner surface of the cortical bone of the tibia. At 630, a patient-specific tibial tray having an inferior surface is determined based on the second data. At 640, the patient's tibia is resected based on the second data. At 650, the tibial tray is formed based on the second data, and at 660, the formed tibial tray is secured onto the formed resected proximal portion of the tibia so that an inferior portion of the tibial tray extends into the one or more cavities and/or openings and contacts the underlying inner surface of the cortical bone of the tibia.

FIG. 7 illustrates a block diagram of a system 700 for implementing, for example, the method 600 (FIG. 6) for use in knee replacement surgery, according to an embodiment of the present disclosure. In this illustrated system 700, for example, at least a portion of a tibial tray when operably attached to a resected proximal portion of the tibia of a patient may interface and increase the contact area with an underlying inner surface of the cortical bone of the proximal portion of the tibia of the patient. System 700 may generally include a processing unit or processor 710, input/output devices 720, and memory 730.

For example, tibia data 702 such as first data representing a proximal portion of a tibia of the patient (block 610 in FIG. 6) may be inputted to system 700. Tibia data 702 may include three-dimensional data obtained by, for example, a Computed Tomography (CT) scan, a Computerized Axial Tomography (CAT) scan, a Magnetic Resonance Imaging (MRI) scan, or other suitable two-dimensional imaging or three dimensional imaging or processing. Such data may be provided directly from an imaging machine or retrievable from a database of stored medical image data. Further input data may include surgeon input 704 such as a desired general configuration of the tibial tray, desired tibial cuts, and/or other information. The processor 710 may be a computer operating, for example, WINDOWS, OSX, UNIX or Linux operating system. In some embodiments, the processor 710 may be a portable or handheld computing device. In other embodiments, the processing unit 710 may be one or more operably connected processing units, computing devices, servers, linked or operating over one or more networks such a global communications network, e.g., the Internet.

The memory 730 may include various modules for processing the input data. For example, the memory 730 may include a tibia cut generator 740, a robotic tibia cut plan generator 750, and a tibial tray generator 760.

The tibia cut generator 740 may be operable for determining the second data representative of the patient-specific resected proximal portion of the tibia of the patient based on the first data (block 620, FIG. 6). For example, the second data may be based on the first data, which the first data includes the outer shape of the proximal portion of the tibia, shape of the intercondylar eminence, the lateral condyle, medial condyle, diseased or damaged portions thereof, inner surface of the cortical bone portion, spongy bone portion, and other features. For example, the second data may be identified with sub-voxel (e.g., volumetric pixel data) accuracy of the location of "cortical bone" (e.g., the location of the inner surface of the cortical bone region) relative to "outer surface of the cortical bone" (e.g., the location of the outer surface of the cortical bone region). Using such a high fidelity bone model, suitable programing may be provided for forming a virtual representation of a proposed resected proximal portion of the tibia for receiving a tibial tray that may be generated with a high degree of compatibility with the patient's bone. The resected proximal portion of the tibia of the patient may include a superior surface and one or more openings or cavities exposing an inferior or underlying surface of the cortical bone.

The cut generator 740 may include various modules such as a resection surface generator 742, a cavity generator 744, and an optimizing generator 746. The resection generator 742 may allow for a surgeon to indicate, for example, a resection plane or such plane may be automatically generated provided, e.g., by input by a surgeon, or based on or utilizing predetermined data. For example, the resection plane may be determined as disclosed in U.S. patent application Ser. No. 16/153,334, entitled, "Apparatus, Method and System for Providing Customizable Bone Implants", the entire subject matter of which is incorporated herein by reference. The cavity generator 744 may include receiving initial inputs from a surgeon such as locations, widths, lengths, depths, or may be based on or utilizing predetermined data. Optimizing generator 746 may take the inputted or generated configuration of the tibial tray, and virtually test or compare such tibial tray installed in the resected tibia based on forces likely to be experienced. Automatically varying of the dimensions may allow for comparison to previous developed configurations to optimize the configuration of the patient-specific resected tibia and the tibial tray. In some embodiments, optimizing generator 746 may optimize the depth of the walls, the thickness of the walls, and the amount and location of the walls that extend around the tibial tray to result in a reduce removal amount needed of the cancellous bone, thereby causing less trauma to the tibial of the patient. In some embodiments, a suitable module in the memory 730 may have suitable programming or algorithms for virtually testing a resultant patient-specific proximal portion of the tibia and corresponding tibial tray, or for comparison the resultant patient-specific proximal portion of the tibia and corresponding tibial tray against exemplary acceptable configurations. Such optimizing techniques are described below.

The robotic tibia cut plan generator 750 may be operable to determine data or instructions for operating a surgical robot 790 or other automated device for forming the patient's tibia based on the second data (block 640, FIG. 6). In some embodiments, a 3D model of the resected proximal portion of the patient's tibia may be uploaded to the robot and the surgical robot being operable to effect a tibia cut plan to resize the proximal portion of the tibia autonomously, or semi-autonomously to form, for example, a resection and form the one or more cavities or openings or to expose the underlying inner surface or portion of the cortical bone. The data or instructions may be combined with data received by the surgical robot 790 such as data from local cameras imagers or sensors. A suitable surgical robot may be an LBR iiwa Kuka robot manufactured by KUKA ROBOTICS Corporation of Shelby Township, Michigan, and may be operable with one or more bone saws, rasps, saws, drills, and/or other devices.

The tibial tray generator 760 may be operable to determine a configuration of a patient-specific tibial tray having, for example, an inferior surface based on the second data (block 630, FIG. 6). For example, the tibial tray generator 760 may determine the body of the tibial tray having a periphery and inferior surface that matches or corresponds to the resected proximal portion of the tibia. In some embodiments, a 3D model of the tibial tray may be used by a 3D printer 795 or other manufacturing device known in the art for generating a tibial tray. The 3D printer or manufacturing device may be operable to form the tibial trays, as described above, as a one-piece, monolithic, or integral body, or formed from one or more components, and formed from a standard metallic material, such as titanium, cobalt chrome, or other acceptable stainless steels. Alternative, a prototype or mold may be formed and used for forming by casting or forging the tibial tray implant formed from, for example, a standard metallic material, such as titanium, cobalt chrome, or other acceptable stainless steels.

The technique of the present disclosure may solve the problem by more closely matching the native anatomy of the joint and thereby increasing the surface area contact for osseointegration and reducing shear forces along the implant to bone interface plane. Osseointegration (organic fixation) may occur from cortical contact. For example, the system may introduce patient-specific wall, supports, or pegs that interface with the underlying cortical metaphyseal bone to add stability and resist subsidence. By mapping the contours of the metaphyseal bone (the transitional zone at which the diaphysis and epiphysis of a bone come together) such that a tibial tray can be formed and readily inserted.

Programming code or algorithms, such as in the tibia cut generator 750, may include the introduction of non-planar shapes to the bottom of the tibial tray that may increase the surface area contact of the resected tibia significantly. By way of example, the surface area of a circle in a plane is characterized by the equation (Area of Circle=πr2). The surface area of a semi-spherical shape approximated by a half-sphere is characterized by the equation (Area of a half-sphere=2πr2). Thus, the introduction of semi-spherical shapes can increase the surface area contact significantly. By way of nonlimiting example, a half-sphere has twice the surface area of a circle of equal radius. The configuration of a normal proximal portion of the tibia is not a flat plane, but the anatomy is characterized by concave and convex geometries, and the tibia cut generator 750 in determining the resected proximal portion of the tibia may be based on the surface area being non-parallel.

Figure 9:
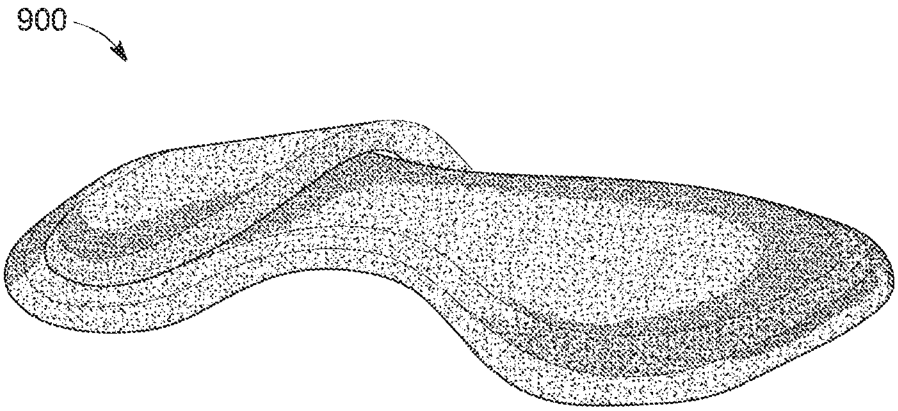
FIG. 9 is a graphical representation of a proximal portion of a tibia of a patient, according to embodiment of the present disclosure.

An approximation of these concave and convex surface features 900 is illustrated in FIG. 9, and a patient specific knee may be designed such as in the tibia cut generator 740 (FIG. 7) To generally approximate these anatomical surface features. Notably, these surface features may be geometrically approximated such that the minimum height as measured between the lowest and highest members along the resection plane excluding the keel and pins shall exceed about 0.5 mm and the maximum height as measured between the lowest and highest members along the resection plane excluding the keel and pins shall not exceed about 25 mm. It is understood that the medial and lateral condyles and intercondylar eminence may generally approximate regions of local maximum and minimum or minimum and maximum along the resection plane. In some embodiments, programming code or algorithms in the tibia cut generator 740 (FIG. 7) may determine the resected proximal portion of the tibia based on one or more angled surfaces, and the resulting shear forces. For example, the shear force at any point of the implant to bone contact plane may be characterized by and based on the equation Fx=Fcos(theta) where shear force is reduced as theta is increased.

Figure 10:
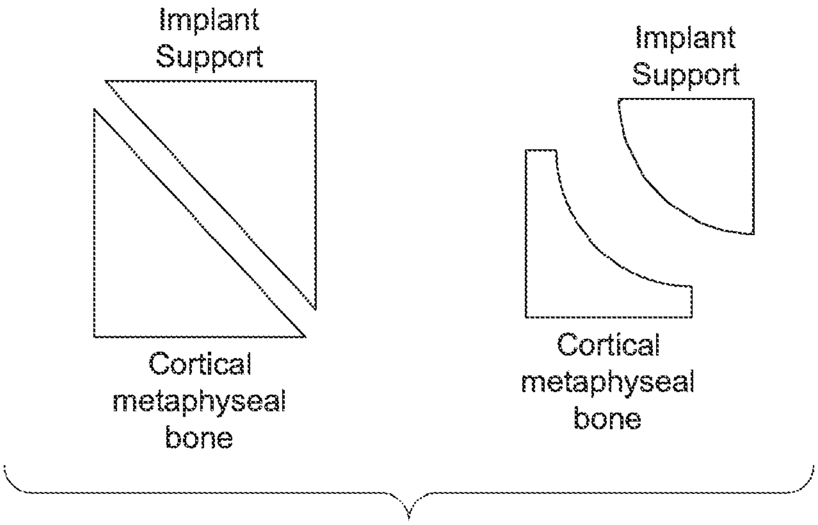
FIG. 10 illustrates two bone-to-implant interfaces for support pins, according to embodiment of the present disclosure.

FIG. 10 illustrates two bone-to-implant interfaces of the support pins and the cortical metaphyseal bone, which may be flat or curved such that the surface area contact is reasonably maximized. Such analysis may be employed in the optimizing generator 746 (FIG. 7).

In other embodiments, auto-segmentation and implant generation algorithms may be utilized with a surgical robot to introduce pre-planned semi-oblong irregular shapes and cavities into the proximal tibial surface that are designed for engagement with a conforming patient-specific tibial tray generated by the algorithms. For example, a pre-operative anatomy of the tibia is characterized by segmentation and implant generation algorithms, which are designed to output a robotic surgical plan and a corresponding patient-specific implant. The algorithm outputs may be designed to loosely reconstruct the pre-operative curvature of the native anatomy (geometric approximations of the proximal surface of the tibia, specifically the medial and lateral condyles, intercondyle eminence and medial and lateral curved plateaus) as well as may introduce cavities for pegs of variable length and with high conformity to the underlying bone. The algorithm may map the contours of the metaphyseal bone such that a high conformity implant can be inserted. The surgical robot may prepare these surface features with tissue ablation tooling (for example burrs, sagittal saws, drills, etc.) and the implant may be 3D printed, forged or cast.

The tibial tray may be aligned at the surgeon's discretion and input or by system 700. The total knee arthroplasties (TKA) of the present disclosure may be aligned with the tibial component, which is positioned perpendicular to the anatomic axis of the tibia similar to conventional TKAs. For example, the anatomic axis may be colinear with the mechanical axis unless there is some unusual deformity. Alternatively, a so-called kinematic or anatomic technique may be employed in which the goal is to recreate the native sagittal and coronal orientation of the tibial joint surface (e.g., restore the joint surface to where it was before arthritis set in). There is variation in the native alignment of the tibia. The coronal alignment typically averages 3 degrees of varus and the sagittal (posterior slope) averages 7 degrees or so but ranges widely between 0 and 15+. The algorithms in the tibia cut generator may be able to apply either technique.

Figure 8:
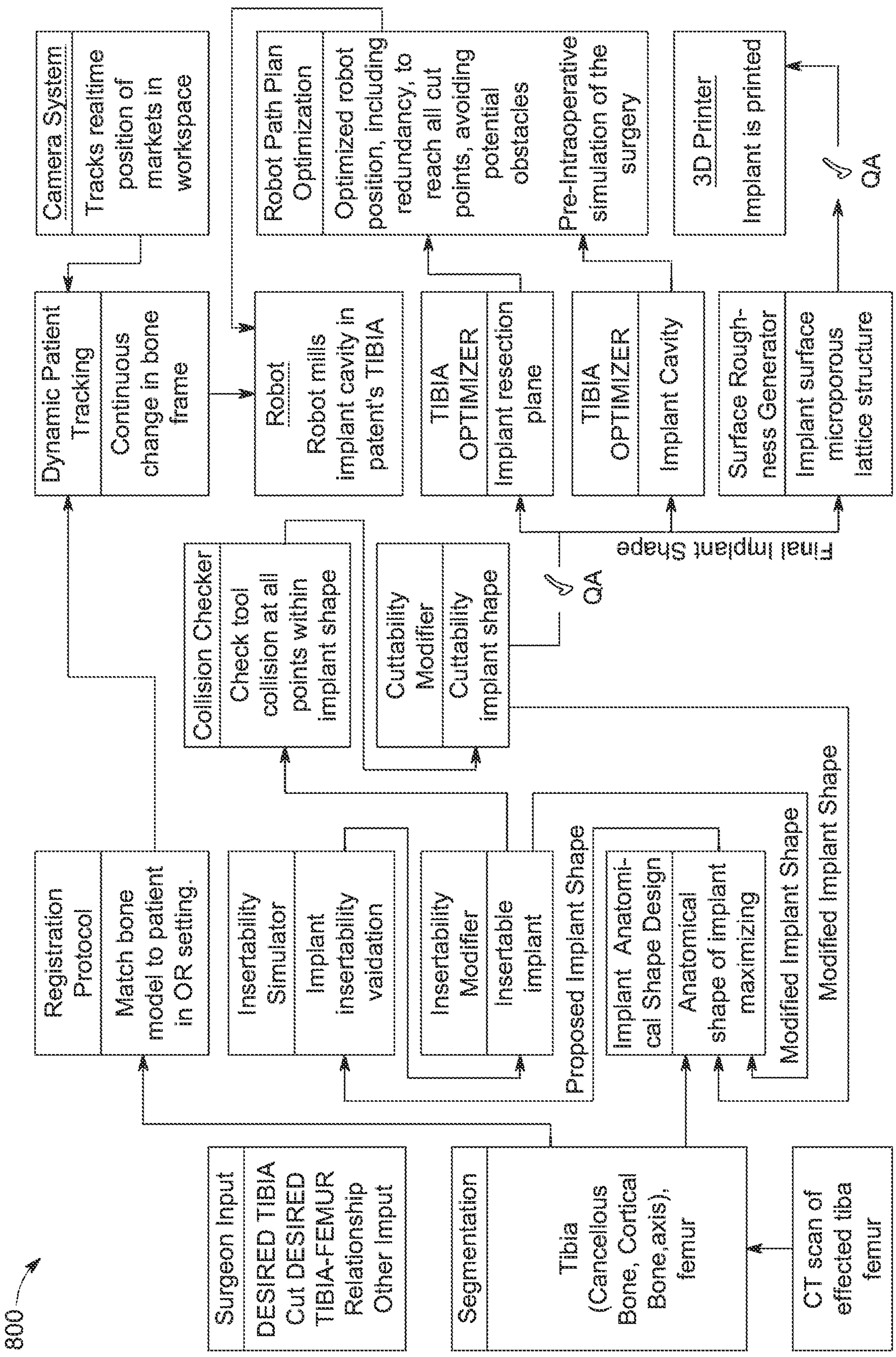
FIG. 8 is a block diagram of a system for repairing a knee joint of a patient, according to an embodiment of the present disclosure.

FIG. 8 illustrates a block diagram of a system 800 for implementing, for example, the method 600 (FIG. 6) for use in knee replacement surgery, according to an embodiment of the present disclosure.

Figure 11:
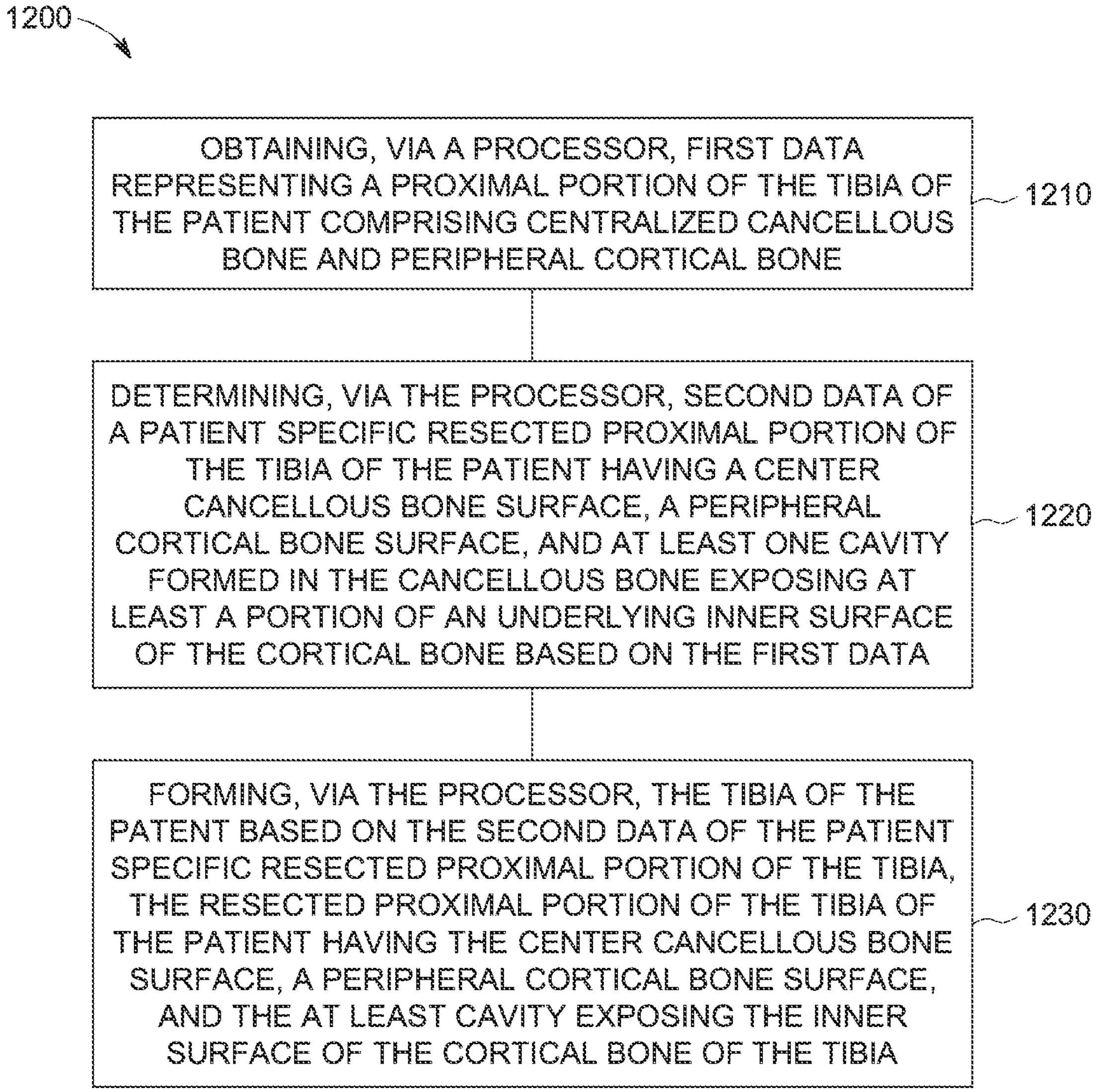
FIG. 11 is a flowchart of a robotic process for repairing a knee joint of a patient, according to an embodiment of the present disclosure.

FIG. 11 illustrates a block diagram of a robotic method 1200 for resecting a tibia of a patient for a knee replacement. The method 1200 includes, for example, at 1210 obtaining, via a processor, first data representing a proximal portion of the tibia of the patient. The method further may include at 1220 determining, via the processor, second data of a patient-specific resected proximal portion of the tibia of the patient based on the first data and based on location of an inner surface of the cortical bone of the tibia. The method may also include at 1230 forming, via the processor, the tibia of the patent based on the second data of the patient-specific resected proximal portion of the tibia, the resected proximal portion of the tibia of the patient having one or more cavities and/or openings exposing an inferior portion of an inner surface of the cortical bone of the tibia.

Figure 12:
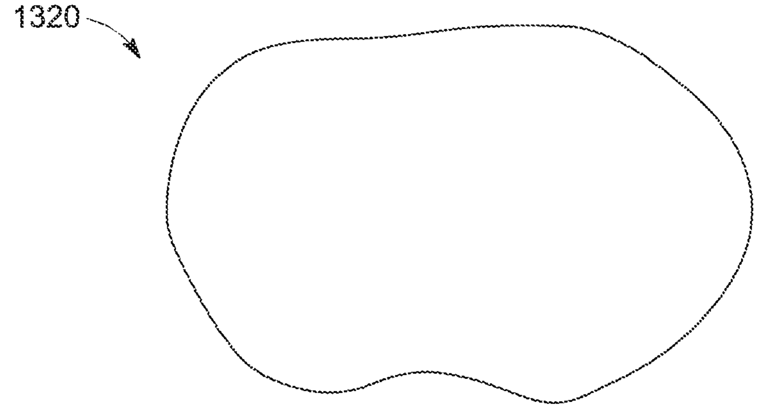
FIGS. 12-14 are superior, posterior perspective, and inferior views of a tibial tray, according to an embodiment of the present disclosure.
Figure 13:
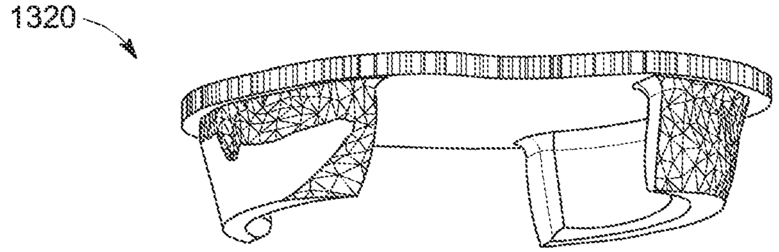
Figure 14:
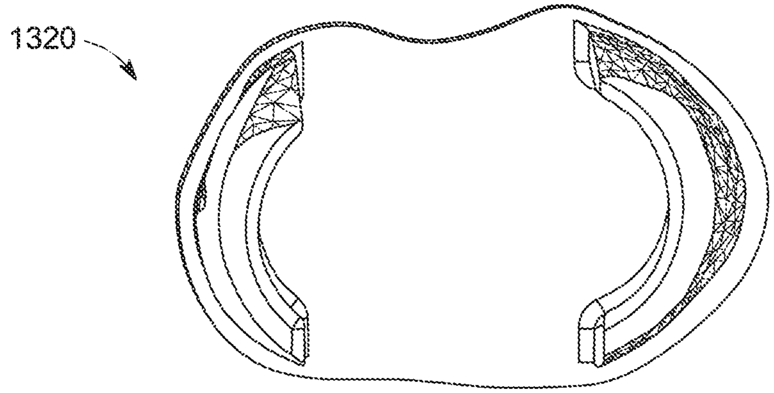
Figure 15:
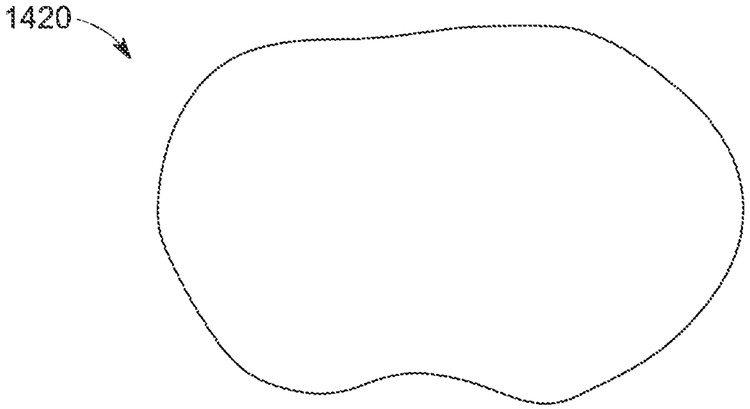
FIGS. 15-19 are superior, posterior perspective, inferior, posterior perspective, and anterior perspective views of a tibial tray, according to an embodiment of the present disclosure.
Figure 16:
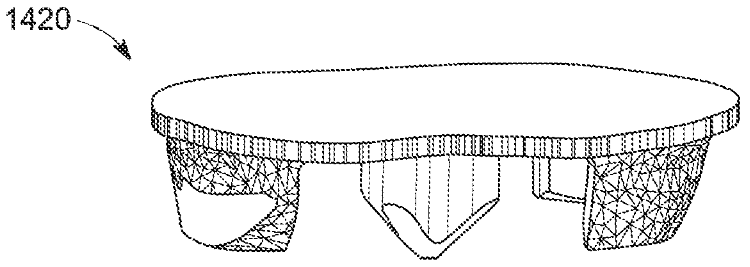
Figure 17:
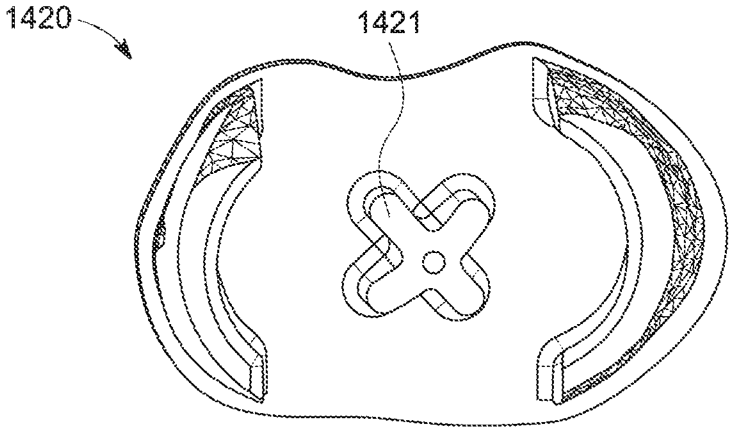
Figure 18:
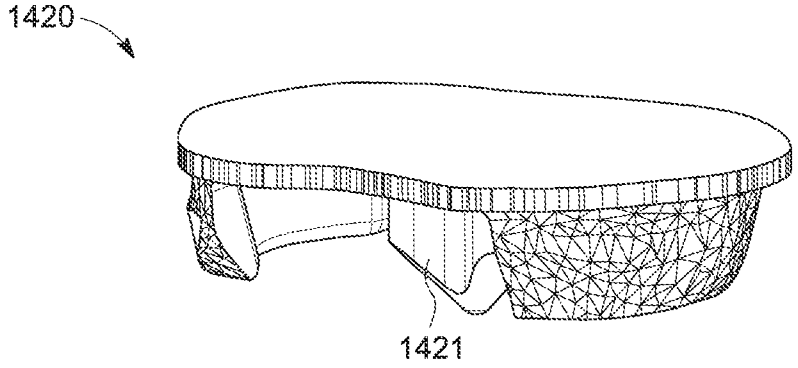
Figure 19:
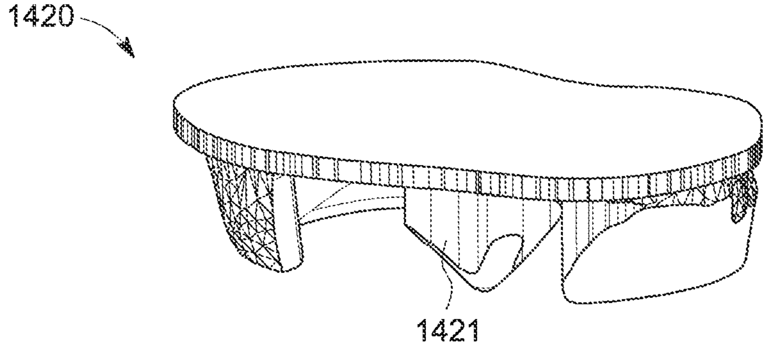

FIGS. 12-14 illustrate a tibial tray 1320, according to an embodiment of the present disclosure. In this illustrated embodiment, at least a portion of the tibial tray 1320 when operably attached to a resected proximal portion of a tibia of a patient will interface and increase the contact area with a side portion of an inner surface of the cortical bone of a proximal portion of the tibia. For example, the tibial tray 1320 may be configured similar to tibial tray 20 (FIG. 1). In this embodiment, tibial tray 1320 does not include a keel.

Figure 20:
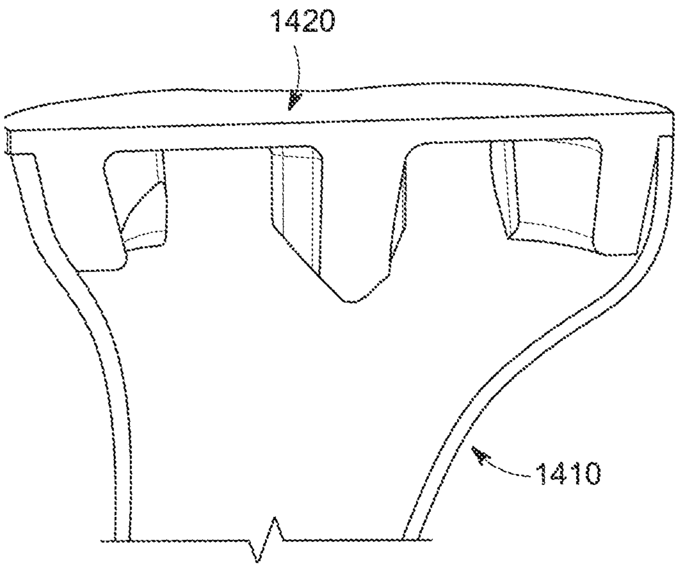
FIGS. 20 and 21 are cross-sectional views of the tibial tray of FIG. 16 disposed on a resected proximal portion of a tibia.
Figure 21:
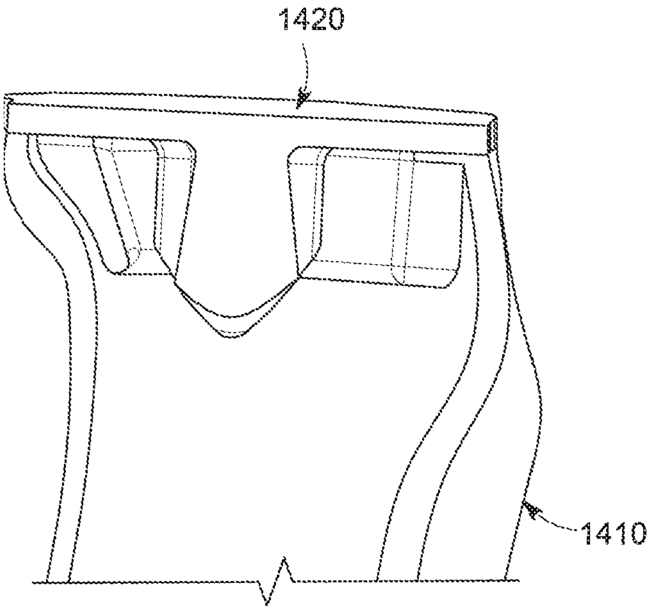

FIGS. 15-19 illustrate a tibial tray 1420, according to an embodiment of the present disclosure. For example, the tibial tray 1420 may be configured similar to tibial tray 1320 (FIGS. 12-14) with the addition of a keel 1421 (FIGS. 17-20). FIGS. 20 and 21 illustrate tibial tray 1420 disposed on a resected proximal portion of a tibia 1410 of a patient.

Figure 22:
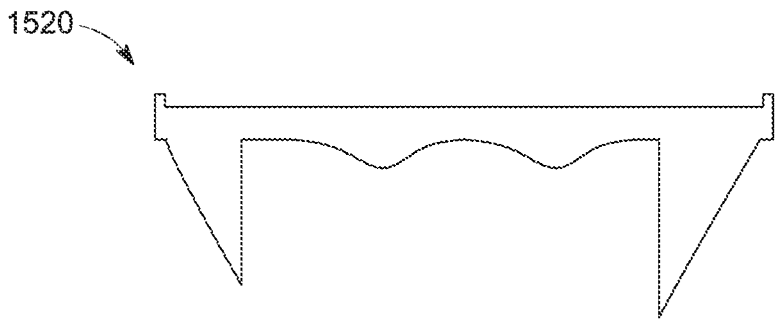
FIG. 22 is a frontal cross-sectional view of a tibial tray, according to an embodiment of the present disclosure.
Figure 23:
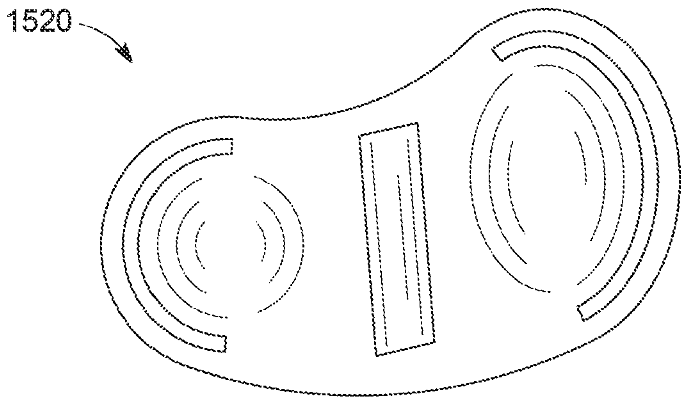
FIG. 23 is a superior view of the tibial tray of FIG. 22, according to an embodiment of the present disclosure.

FIGS. 22 and 23 illustrate a tibial tray 1520, according to an embodiment of the present disclosure. In this illustrated embodiment, at least a portion of the tibial tray 1520 when operably attached to a resected proximal portion of a tibia of a patient will interface and increase the contact area with an inner surface of an inner surface of the cortical bone of a proximal portion of the tibia. For example, the tibial tray 1520 may be configured similar to a combination of tibial tray 20 (FIG. 1) and tibial tray 420 (FIG. 4). In this embodiment, tibial tray 1520 may include a tibia engaging portion having peripheral walls and a non-planar center portion. The center portion may be designed to interface with curved surface geometries and support cavities of a resected proximal portion of a tibia. For example, the center portions of the tibial tray may include a convex minimum near the lateral condyle, a concave maximum near the intercondyle eminence, and a convex minimum near the medial condyle. The outer edges of the convex surfaces, as shown in FIG. 23, may have an oval or a generally egg-shaped configuration.

Figure 24:
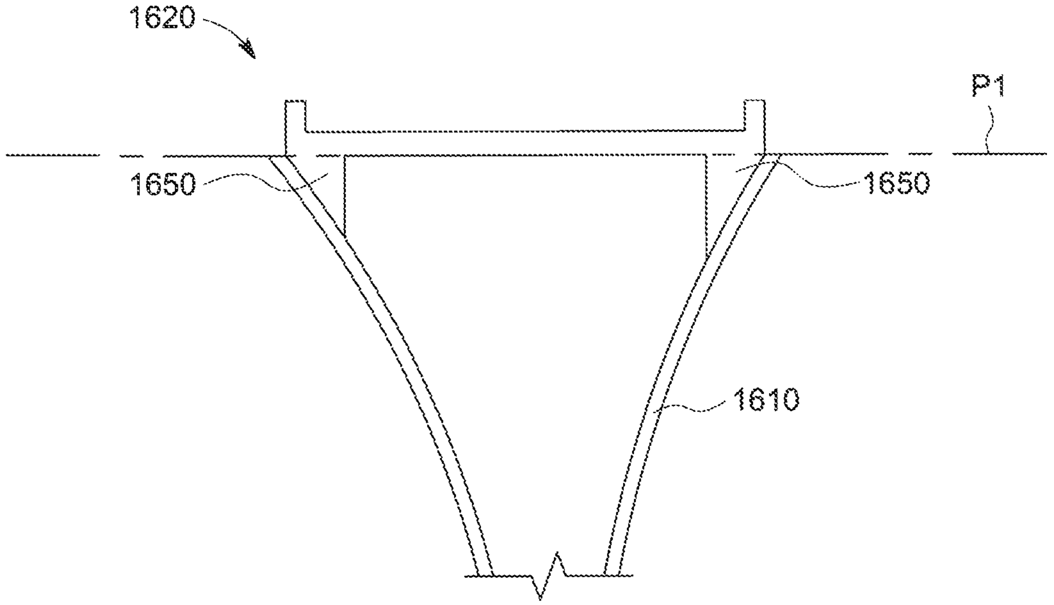
FIG. 24 is a frontal cross-sectional view of a resected proximal portion of a tibia of a patient and a tibial tray, according to an embodiment of the present disclosure.

FIG. 24 illustrates a tibial tray 1620, according to an embodiment of the present disclosure. In this illustrated embodiment, at least a portion of the tibial tray 1620 when operably attached to a resected proximal portion of a tibia 1610 of a patient will interface and increase the contact area with an inner surface of a cortical bone of a proximal portion of the tibia. For example, the tibial tray 1620 may be configured to be received between inner surface portions of the cortical bone. In this embodiment, a resected portion of the patient's tibia may be along a plane P1. Cavities may be provided in the patient's tibia for receiving inferiorly-extending peripheral portions 1650 of the tibia engaging portion of the tibial tray 1620. In this embodiment, the tibial tray does not sit on top of the resected superior edge of the cortical bone of the patient's tibia, but instead extends above the top of the resected superior edge of the cortical bone of the patient's tibia.

Figure 25:
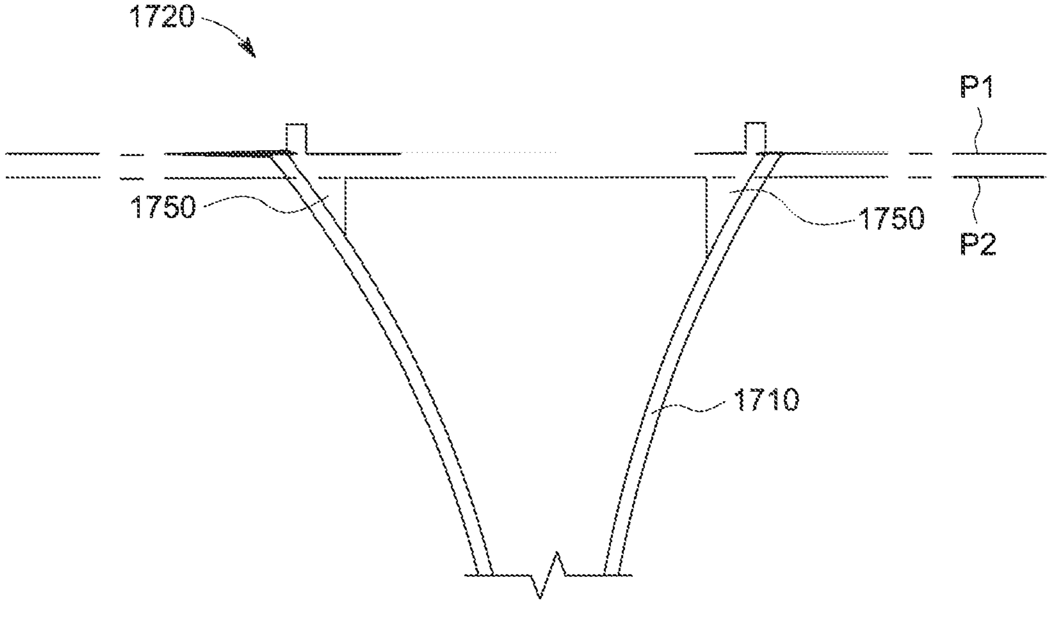
FIG. 25 is a frontal cross-sectional view of a resected proximal portion of a tibia of a patient and a tibial tray, according to an embodiment of the present disclosure.

FIG. 25 illustrates a tibial tray 1720, according to an embodiment of the present disclosure. In this illustrated embodiment, at least a portion of the tibial tray 1720 when operably attached to a resected proximal portion of a tibia 1710 of a patient will interface and increase the contact area with a side portion of an inner surface of the cortical bone of a proximal portion of the tibia. For example, the tibial tray 1620 may be configured to be received between inner surface portions of the cortical bone. In this embodiment, a resected portion of the patient's tibia may be along a plane P1. An initial cavity may be formed having an inferior surface disposed along a plane P2, and cavities may be provided in the patient's tibia for receiving inferiorly-extending peripheral portions 1750 of the tibia engaging portion of the tibial tray 1720. In this embodiment, the tibial tray does not sit on top of the resected superior edge of the cortical bone of the patient's tibia, but instead extends generally even with the top of the resected superior edge of the cortical bone of the patient's tibia.

With reference to FIGS. 26-29, therein illustrated are exemplary embodiments of tibial trays installed on a resected proximal portion of a tibia in which portions of the tibial tray are spaced from and disposed closely adjacent to an underlying inner surface of the cortical bone for use in a total knee replacement.

In some embodiments, for example, a patient-specific tibial tray design may mitigate aseptic loosening and subsidence through a combination of high underlying peripheral surface area contact and underside surface geometry that interfaces more closely with peripheral cancellous bone adjacent to the cortical bone. The present disclosure may solve and/or overcome a primary cause for knee implant failure, namely, aseptic loosening of the tibial component and subsidence.

In some embodiments, the present disclosure is directed to methods for generating a three-dimensional model of a tibia and generating a cut plan for excavating a portion of the tibia with a robot or robotic excavator according to the cut plan to allow for the insertion of a custom tibial tray designed with one or more peripheral inferiorly-extending portions designed to be spaced from the periphery of the underlying tibial cortical bone.

In some embodiments, a technique of the present disclosure is directed to increasing stability of the tibial tray relative to the resected proximal portion of the tibia by employing one or more peripheral inferiorly-extending portions designed to be spaced from the periphery of the underlying tibial cortical bone. A virtual model of the proximal portion of a tibia bone may be used to determine an improved implant that is designed to achieve a higher level of stability. A processor may be employed and configured to generate an excavation protocol for resecting the proximal tibia and excavating cancellous bone from the tibia such that the amount of contact between the tibia and the implant is increased, by, for example, an amount of 10 percent or greater contact compared to convention tibial trays.

Figure 26:
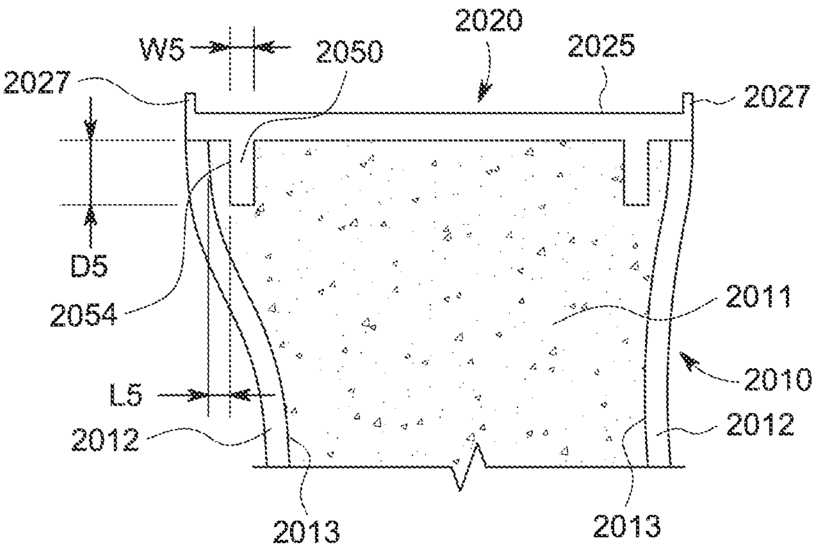
FIG. 26 is a cross-sectional view of a tibial tray disposed on a resected proximal portion of a tibia of a patient, according to an embodiment of the present disclosure.

FIG. 26 illustrates a tibial tray 2020 fitted to a resected proximal portion of a tibia 2010 for a total knee replacement, according to an embodiment of the present disclosure. In this illustrated embodiment, at least a portion of the tibial tray 2020 when operably attached to the resected proximal portion of the tibia 2010 includes peripheral inferiorly-extending portions extending onto the cancellous bone 2011 designed to be offset or spaced from the periphery of the underlying tibial cortical bone 2012 of the proximal portion of the tibia 2010.

Figure 27:
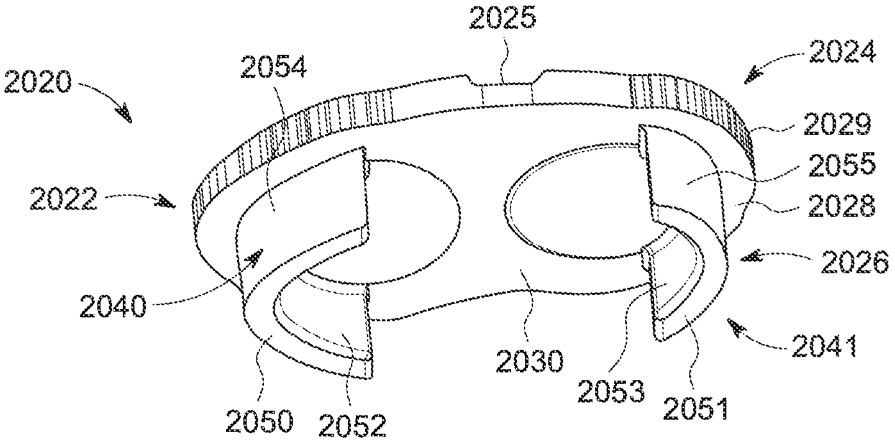
FIG. 27 is an inferior perspective view of the tibial tray of FIG. 26, according to an embodiment of the present disclosure.

For example, as shown in FIG. 27, the tibial tray 2020 may include a body 2022 having a superior portion 2024 and an inferior tibia-engaging portion 2026. The superior portion 2024 may include a generally planar superior surface 2025 (best shown in FIG. 26) for supporting a plastic bearing spacer (not shown). In some embodiments, the planar superior surface 2025 includes a peripheral upwardly-extending lip 2027 (FIG. 26) for attaching via a snap fit connection and restraining the plastic bearing spacer.

With reference still to FIG. 27, the tibia engaging portion 2026 may include a center tibia engaging portion 2030, and a first peripheral tibia engaging portion 2040. In this embodiment, the center tibia engaging portion 2030 may include a contoured surface contactable with the center cancellous bone surface of the resected proximal portion of the tibia of the patient. For example, the center tibia engaging portion may include one or more concave, convex, or planar surfaces contactable with the center cancellous bone surface of the resected proximal portion of the tibia of the patient as similarly described above.

The peripheral tibia-engaging portion 2040 may include at least one inferiorly-extending wall, and may include a first inferiorly-extending wall 2050 and a spaced apart second inferiorly-extending wall 2051. The first inferiorly-extending wall 2050 may include an inner wall surface 2052 and an outer wall surface 2054. For example, the walls 2052 and 2054 may be U-shaped walls facing each other. The second inferiorly-extending wall 2051 may include an inner wall surface 2053 and an outer wall surface 2055. The walls 2050 and 2051 may be a mirror image of wall 2050 and may have constant thicknesses, different thickness, varying thickness, or other suitable thicknesses. The inner wall surfaces 2052 and 2053 may be disposed normal or at 90 degrees to the superior surface 2025, or at any suitable angle or angles. The outer wall surfaces 2054 and 2055 may be disposed normal or at 90 degrees to the superior surface 2025. In other embodiments, the outer wall surface may be angled relative to the superior surface such as parallel with and spaced from an inner surface 2013 (FIG. 26) of the cortical bone 2012 (FIG. 26).

Figure 28:
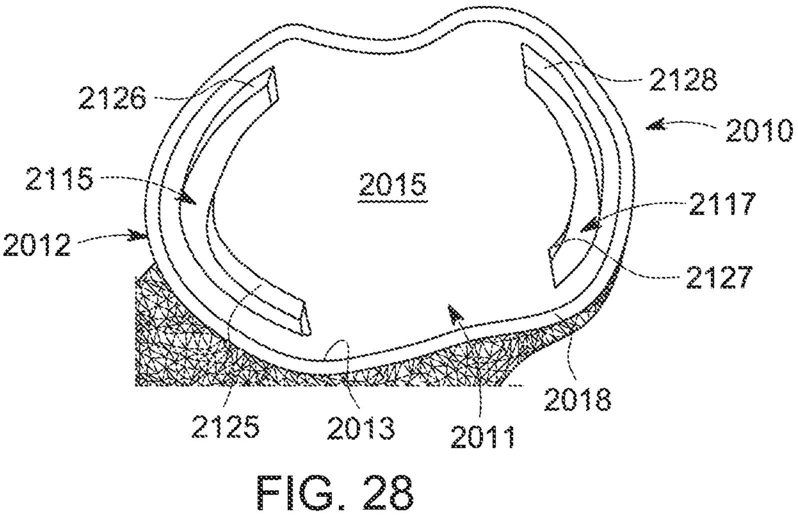
FIG. 28 is a superior view of the resected proximal portion of the tibia of FIG. 26 for receiving the tibial tray of FIG. 27, according to an embodiment of the present disclosure.

FIG. 28 illustrates a superior view of the resected proximal portion of the tibia 2010 of FIG. 26 of the patient for the total knee replacement, according to an embodiment of the present disclosure. In this illustrated embodiment, the resected proximal portion of the tibia 2010 may include the cancellous bone 2011 having a center cancellous surface 2015, and the cortical bone 2012 having a cortical bone edge surface 2018. The cancellous bone 2011 may include a first U-shaped cavity 2115 disposed along one side such as the medial side of the proximal portion of the tibia 2010, and a second U-shaped cavity 2117 disposed along an opposite side such as the lateral side of the proximal portion of the tibia 2010. The first U-shaped cavity 2115 may include an inner surface 2125 and an outer surface 2126. The second U-shaped cavity 2117 may include an inner surface 2127 and an outer surface 2128. The cavities 2115 and 2117 may extend into the cancellous bone 2011 (e.g., trabecular bone, spongy bone, or porous bone) of the proximal portion of the tibia 2010 adjacent to the inner surface 2013 of the cortical bone 2012 of the proximal portion of the tibia 2010. The walls 2050 and 2051 (FIG. 27) are receivable in cavities 2115 and 2017 formed in the resected proximal portion of the tibia 2010. For example, cavities 2115 and 2017 may be sized and configured to correspond to and receive walls 2050 and 2051 (FIG. 27) when tibial tray 2020 is positioned on resected proximal tibia 2010, The inner wall surface 2052 of the first wall 2050 may be disposed adjacent to or abut the inner surface 2125 of the first U-shaped cavity 2115, the outer wall surface 2054 of the first wall 2050 may be disposed adjacent to or abut the outer surface 2126 of the first U-shaped cavity 2115, the inner wall surface 2053 of the second wall 2051 may be disposed adjacent to or abut the inner surface 2127 of the second U-shaped cavity 2117, and the outer wall surface 2055 of the second wall 2051 may be disposed adjacent to or abut the outer surface 2128 of the second U-shaped cavity 2117.

With reference again to FIG. 26, a depth D5 of the wall 2050 may extend for example, about 0.5 millimeters (mm) to about 75 mm, about 1 mm to about 50 mm, about 2 mm to about 40 mm, about 4 mm to about 20 mm, exceed 0.5 mm, about 1 mm, about 2 mm, about 3 mm, about 5 mm, about 7 mm, or other suitable depth. A width W5 of the wall 2050 may be, for example, about 5 mm to about 6 mm and is desirably greater than about 0.5 mm and less than about 50 mm. The lower portion of the outer surface 2054 of the wall 2050 may be spaced from the inner surface 2013 of the cortical bone 2012 a distance L5 of, for example, about 0.5 mm, about 1 mm, about 2 mm, between 0.05 mm and about 10 mm, between about 0.5 mm and about 5 mm, between about 1 mm and about 2 mm, or other suitable distance.

With reference again to FIG. 27, in some embodiments, the inferiorly-extending walls 2050 and 2051 may extend along, for example, at least 25 percent of the periphery of the body 2022, along at least 50 percent of the periphery of the body 2022, extend along the entire periphery of the body 2022, or extend along another suitable amount along the periphery of the body 2022. In some embodiments, a peripheral edge 2029 of the tibial tray 2020 may include a lower surface 2028 that extends over the superior cut cortical bone 2018 (FIG. 28). In some embodiments, the tibial tray 2020 may feature a keel (not shown in FIG. 27). The resection of the proximal tibia and access cavities in the cancellous bone in the proximal portion of the tibia and the corresponding tibial tray may be sized and formed manually by a surgeon or as described above, prepared automatically by a robot.

Figure 29:
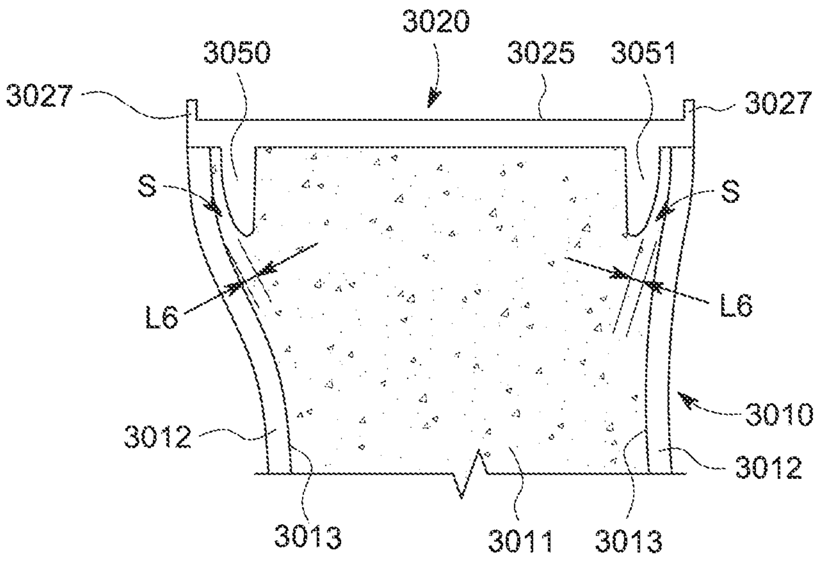
FIG. 29 is a cross-sectional view of a tibial tray disposed on a resected proximal portion of a tibia of a patient, according to an embodiment of the present disclosure.

FIG. 29 illustrates a tibial tray 3020 fitted to a resected proximal portion of a tibia 3010 for a total knee replacement, according to an embodiment of the present disclosure. In this illustrated embodiment, at least a portion of the tibial tray 3020, when operably attached to the resected proximal portion of the tibia 3010, includes peripheral inferiorly-extending portions extending onto the cancellous bone 3011. The peripheral inferiorly-extending portions are designed to be spaced such as offset and parallel to the periphery of the underlying tibial cortical bone 3012 of the proximal portion of the tibia 3010.

Figure 30:
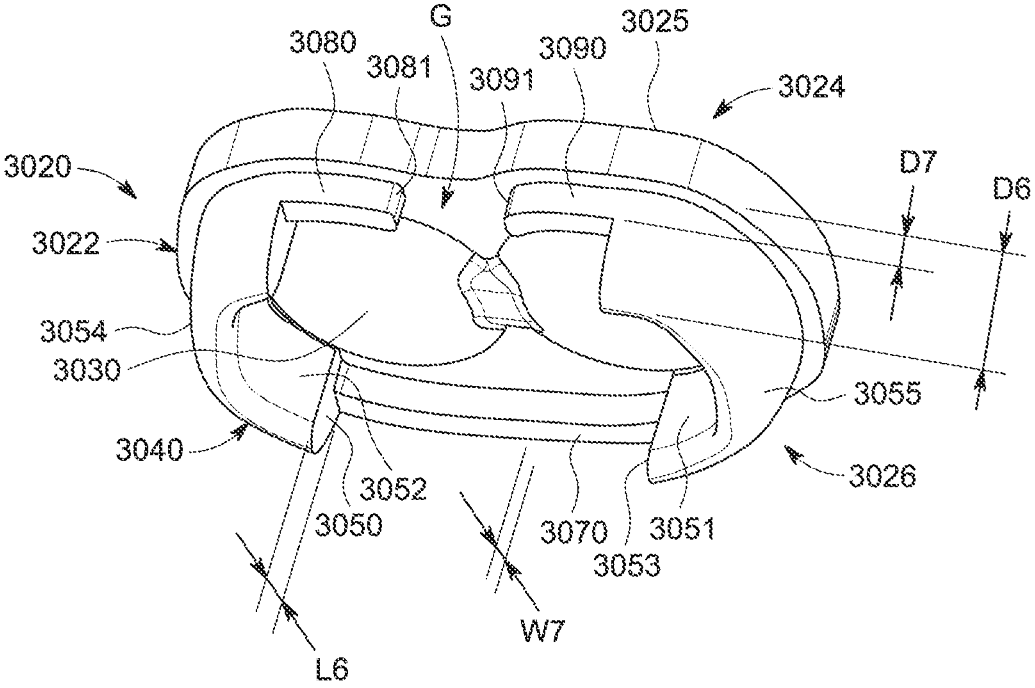
FIG. 30 is an inferior perspective view of the tibial tray of FIG. 29, according to an embodiment of the present disclosure.

For example, as shown in FIG. 30, the tibial tray 3020 may include a body 3022 having a superior portion 3024 and an inferior tibia-engaging portion 3026. The superior portion 3024 may include a generally planar superior surface 3025 (best shown in FIG. 29) for supporting a plastic bearing spacer (not shown). In some embodiments, the planar superior surface 3025 includes a peripheral upwardly-extending lip 3027 (FIG. 29) for attaching via a typical snap fit connection and restraining the plastic bearing spacer.

The tibia engaging portion 3026 may include a center tibia engaging portion 3030 and a peripheral tibia engaging portion 3040. In this embodiment, the center tibia engaging portion 3030 may include a contoured surface contactable with the center cancellous bone surface of the resected proximal portion of the tibia of the patient. For example, the center tibia engaging portion may include one or more concave, convex, or planar surfaces contactable with the center cancellous bone surface of the resected proximal portion of the tibia of the patient as similarly described above.

The peripheral tibia-engaging portion 3040 may include at least one inferiorly-extending wall having portions disposed at different depths. Peripheral tibia-engaging portion 3040 may include, for example, a first inferiorly-extending wall 3050 and a spaced apart second inferiorly-extending wall 3051. Peripheral tibia-engaging portion 3040 may further include a connecting inferiorly-extending wall 3070, a first inwardly-extending wall 3080, and a second inwardly-extending wall 3090. The connecting inferiorly-extending wall 3080 may extend between the first inferiorly-extending wall 3050 and the spaced apart second inferiorly-extending wall 3051. The inwardly facing ends 3081 and 3091 of first inwardly-extending wall 3080 and a second inwardly-extending wall 3090, respectively, may define a gap G disposed along the posterior side of the tibial tray 3020. The gap G may inhibit the need to sacrifice tendons and ligaments at the posterior side of the proximal tibia.

The first inferiorly-extending wall 3050 may include an inner wall surface 3052 and an outer wall surface 3054. The second inferiorly-extending wall 3051 may include an inner wall surface 3053 and an outer wall surface 3055. The walls 3050 and 3051 may have generally constant thicknesses being rounded at the inferiormost end.

The inner wall surfaces 3052 and 3053 may be disposed normal or at 90 degrees to the superior surface 3025, or at any suitable angle or angles. The outer wall surfaces 3054 and 3055 may be sized and configured to provide a generally constant space S (FIG. 29) between the outer wall surfaces 3054 and 3055 and the adjacent inner surface 3013 (FIG. 29) of the cortical bone 3012 (FIG. 29).

With reference again to FIG. 29, the outer surfaces of the walls may be spaced from the inner surface 3031 of the cortical bone, for example, by a distance L6 of about 0.5 mm, about 1 mm, about 2 mm, between 0.05 mm and about 10 mm, between about 0.5 mm and about 5 mm, between about 1 mm and about 2 mm, or other suitable distance.

With reference again to FIG. 30, a depth D6 of the walls 3050 and 3051 may extend, for example, about 0.5 mm to about 75 mm, about 1 mm to about 50 mm, about 2 mm to about 40 mm, about 4 mm to about 20 mm, exceed about 0.5 mm, about 1 mm, about 2 mm, about 3 mm, about 5 mm, about 7 mm, or other suitable depths. A depth D7 of the connecting wall 3070 and inwardly extending walls 3080 and 3090 may extend, for example, about 0.5 mm to about 75 mm, about 1 mm to about 50 mm, about 2 mm to about 40 mm, about 4 mm to about 20 mm, exceed about 0.5 mm, about 1 mm, about 2 mm, about 3 mm, about 5 mm, about 7 mm, or other suitable depths. In some embodiments, the depth D7 of the connecting wall 3070 and inwardly extending walls 3080 and 3090 may be, for example, about 20 percent, about 25 percent, about 30 percent, or other suitable percentage of depth D6. A width W6 of the walls 3050 and 3051 may be, for example, about 5 mm to about 6 mm and is desirably greater than about 0.5 mm and less than about 50 mm. A width W7 of the walls 3070, 3080, and 3090 may be, for example, about 5 mm to about 6 mm and is desirably greater than about 0.5 mm and less than about 50 mm. In some embodiments width W7 may be, for example, less that width W6, such as width W7 being half the width compared to width W6.

With reference again to FIG. 29, the resection of the proximal tibia 3010 and access cavities in the cancellous bone in the proximal portion of the tibia and the corresponding tibial tray 3020 may be sized and formed manually by a surgeon or as described above, prepared automatically by a robot.

Figure 31:
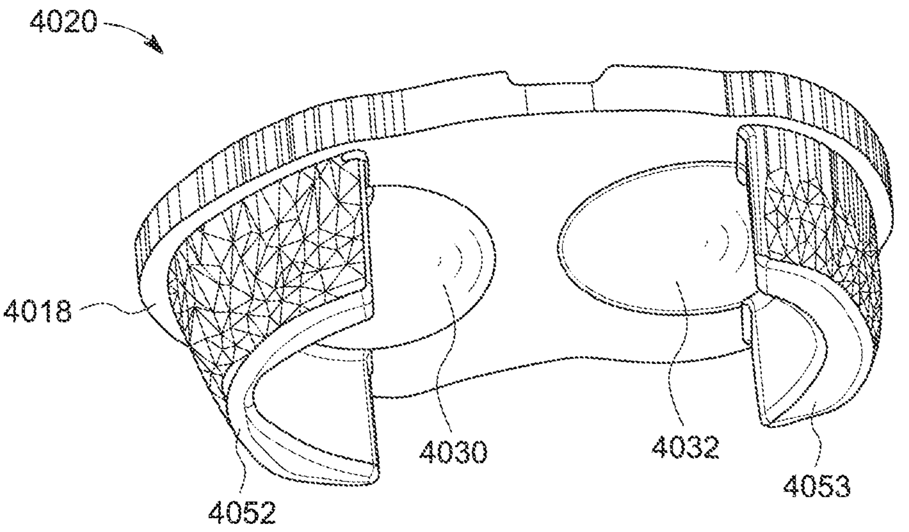
FIG. 31 is an inferior perspective view of a tibial tray, according to an embodiment of the present disclosure.
Figure 32:
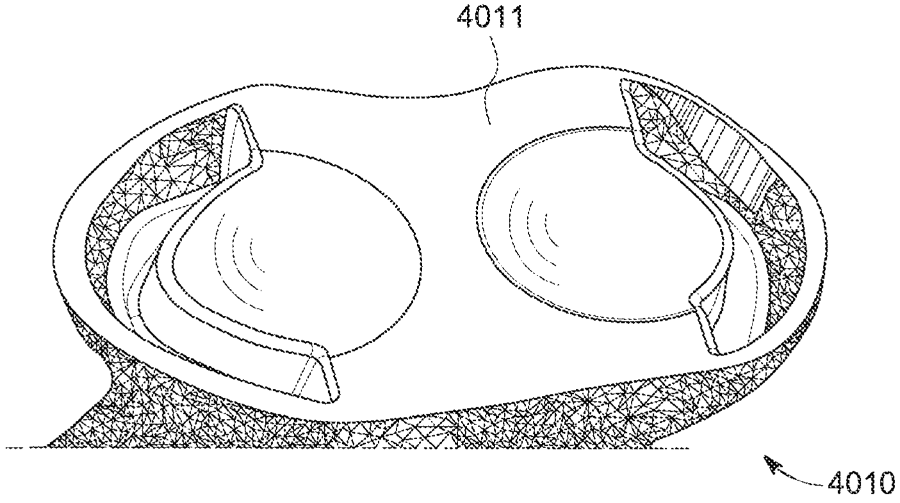
FIG. 32 is a superior view of the resected proximal portion of a tibia for receiving the tibial tray of FIG. 31, according to an embodiment of the present disclosure.

FIGS. 31 and 32 illustrate a tibial tray 4020 (FIG. 31) according to an embodiment of the present disclosure, which may be fitted to a resected proximal portion of a tibia 4010 (FIG. 32) of a patient for a total knee replacement. In this illustrated embodiment, at least a portion of the tibial tray 4020, when operably attached to the resected proximal portion of a tibia 4010 (FIG. 32) of a patient, includes peripheral inferiorly-extending portions extending onto the cancellous bone 4011 (FIG. 32) in close proximity to the cortical wall of the resected proximal tibia. The peripheral inferiorly-extending portions may be designed to be spaced such as offset and/or parallel to the periphery of the underlying tibial cortical bone of the proximal portion of the tibia of the patient.

As illustrated in FIG. 31, tibial tray 4020 may have asymmetrical convex surfaces 4030 and 4031, and asymmetrical peripheral inferiorly-extending portions 4052 and 4053 extending from the undersurface of the tibial tray 4020 to enhance force distribution over the medial and lateral compartments, and may further include a rim 4018 that extends around some, almost all, or all of the entire periphery of the tibial tray 4020. In addition to portions of the tibial tray being asymmetrical, the peripheral inferiorly-extending portion 4052 may be angled and thinner that the peripheral inferiorly-extending portion 4053, which is thicker and aligned more vertically.

In the various embodiments, desirably, the cavities and walls do not penetrate the outer cortical bone. In other embodiments, a portion of the cavities or walls such as the lower portions thereof may contact or extend into the cortical bone.

FIG. 33 illustrates a method 6000 for use in total knee replacement surgery, according to an embodiment of the present disclosure. In this illustrated embodiment, the method 5000 is operable in providing a customized cut plan of the proximal portion of the tibia for a patient and in providing a corresponding customized tibial tray. The method 5000 may include, for example, at 5100 obtaining first data representing a proximal portion of the tibia of the patient. At 5200, second data of a patient-specific resected proximal portion of the tibia of the patient is determined based on the first data. The resected proximal portion of the tibia of the patient has a superior surface and at least one cavity in the cancellous bone exposing a peripheral underlying portion of the cancellous bone of the tibia of the patient. At 5300, a patient-specific tibial tray having an inferior surface is determined based on the second data. At 5400, the patient's tibia is resected based on the second data. At 5500, the tibial tray is formed based on the second data, and at 5600, the formed tibial tray is secured onto the resected proximal portion of the tibia so that a peripheral inferior portion of the tibial tray extends into the at least one cavity and is spaced apart from the underlying cortical bone of the tibia of the patient.

FIG. 34 illustrates a block diagram of a robotic method 6000 for resecting a tibia of a patient for a total knee replacement. The method 6000 includes, for example, at 6100 obtaining, via a processor, first data representing a proximal portion of the tibia of the patient having centralized cancellous bone and peripheral cortical bone. The method further may include at 6200 determining, via the processor, second data representing a patient-specific resected proximal portion of the tibia of the patient having a center cancellous bone surface, a peripheral cortical bone surface, and at least one cavity formed in the cancellous bone surface spaced apart from the cortical bone exposing a peripheral underlying portion of the cancellous bone of the tibia of the patient based on the first data. The method may also include at 6300 forming, via the processor, the tibia of the patent based on the second data representing the patient-specific resected proximal portion of the tibia, the resected proximal portion of the tibia of the patient having a center cancellous bone surface, a peripheral cortical bone surface, and at least one cavity exposing a peripheral underlying portion of the cancellous bone spaced apart from the underlying inner surface of the cortical bone of the tibia of the patient.

In further embodiments, a patient matched or customized tibial tray may include, for example, inferiorly-extending pegs, flanges, fins, etc. that are positioned at or near the peripheral edge of the tibial tray and which, when installed, is received in one or more cavities or holes in the cancellous bone spaced apart from and in close proximity with the underlying inner surface of the cortical bone in the resected proximal portion of the patient's tibia. An alternative embodiment of the tibial tray may have, for example, asymmetrical convex elements extending from the undersurface of the tray to enhance force distribution over the medial and lateral compartments and a rim that extends around all, almost the entire, or a portion of the peripheral superior surface of the resected cortical bone.

The present disclosure is also directed to methods and systems for generating a three dimensional cut plan for excavating portions of the proximal tibia for a total knee replacement using a robot or robotic excavator according to the cut plan to create cavities that allow for the insertion of the custom tibial trays shown and described in connection with FIGS. 26-30, which may be effected using the system 700 of FIG. 7 and system 800 of FIG. 8, and which may result in increased or maximized stabilization of the tibial tray post-implantation. The robot may employ images or cameras for optical tracking to navigate the anatomy and may actively create the custom cavities, for example, may not need to rely on haptic feedback or a surgeon to execute the cuts.

Figure 35:
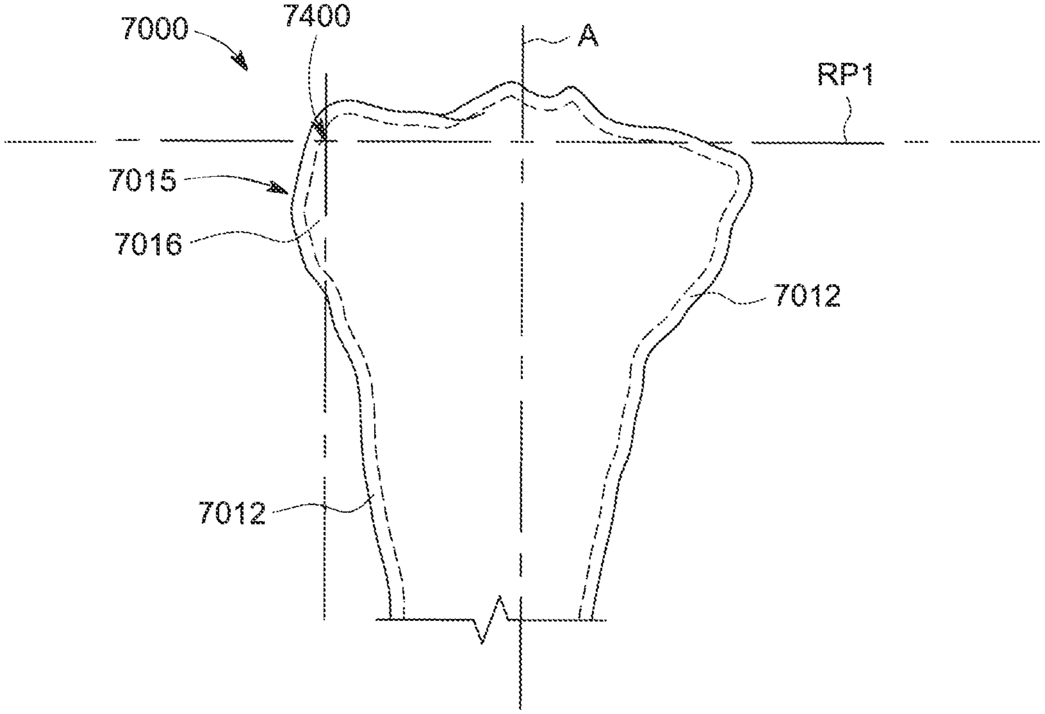
FIG. 35 is an elevational anterior view of a proximal portion of a tibia of a patient for a knee replacement, according to an embodiment of the present disclosure.

FIG. 35 illustrates a proximal portion of a tibia 7000 of a patient for a total knee replacement, according to an embodiment of the present disclosure. The lateral portion and/or the medial portion may include a portion of the cortical bone 7012 that extends inwardly towards the uppermost portion of the tibia 7000. For example, as show in FIG. 35, a proximal lateral portion 7015 of the cortical bone 7012 of the tibia 7000 may extend inwardly towards the uppermost portion of the tibia 7000 resulting in an inner surface 7016 of the cortical bone 7012 having an inner concave surface.

As described above, the tibial trays according to the present disclosure for use in a total knee replacement may include one or more inferiorly-extending walls with an outer wall surface and an inner wall surface. The outer wall surface may be configured to correspond and contact an underlying inner surface of the cortical bone or be spaced from and disposed closely adjacent to an underlying inner surface of the cortical bone. It will be appreciated that a tibial tray having an inferiorly-extending wall corresponding to the location of the lateral cortical bone having an inner concave surface 7016 below a resection plane RP1 may result in the one or more inferiorly-extending walls of the tibial tray not being insertable in the resected proximal tibia with one or more cavities for receiving the one or more inferiorly-extending walls.

Figure 36:
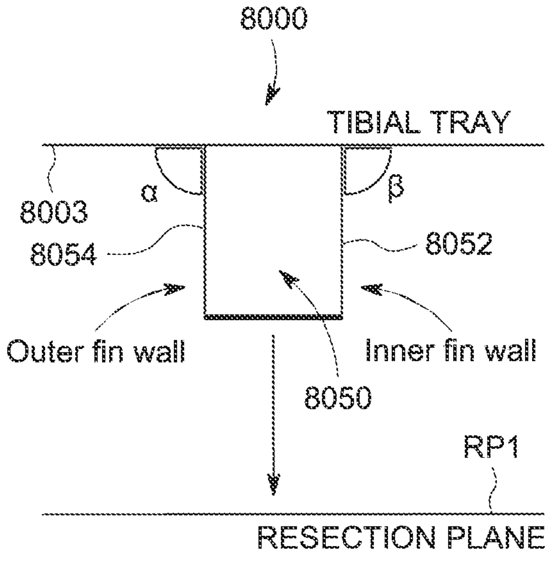
FIG. 36 is a diagrammatic illustration of a portion of a tibial tray, according to an embodiment of the present disclosure.

As shown in FIG. 35, a flat resection plane may be resection plane RP1 that is positioned perpendicular to an anatomic axis A of the tibia 7000. With reference to FIG. 36, in order for a tibial tray 8000 to be insertable close proximity to the inner surface of the cortical bone 7012 (FIG. 35), an angle $\alpha$ between a bottom surface 8003 of the tibial tray 8000, which bottom surface 8003 rests on the flat resection plane RP1, and an outer surface 8054 of the one or more inferiorly-extending walls 8050 must be equal to or greater than 90 degrees. For the tibial tray 8000 to be insertable the angle $\beta$ between the bottom surface 8003 of the tibial tray 8000 and an inner surface 8052 of the one or more inferiorly-extending walls 8050 must be equal to or greater than 90 degrees.

Figure 37:
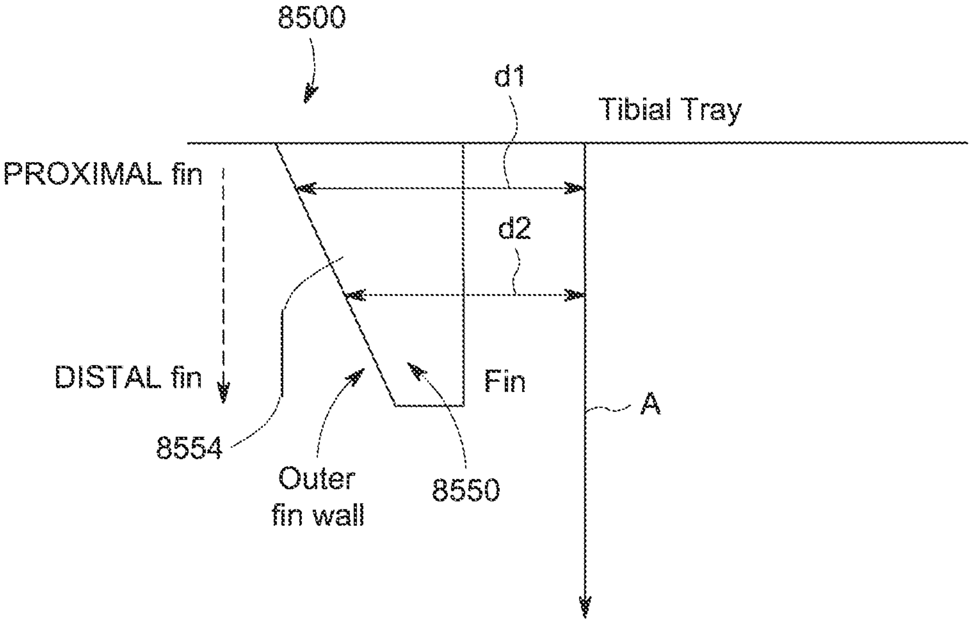
FIG. 37 is a diagrammatic illustration of a portion of a tibial tray, according to an embodiment of the present disclosure.

With reference to FIG. 37, in the design and/or fabrication of a tibial tray, for example, using the system 700 (FIG. 7) or system 800 (FIG. 8) the method may include algorithms or programing code to maintain the ability to insert a tibial tray 8500 with the one or more inferiorly-extending walls 8550 in a resected proximal portion of a tibia. To maintain the ability to insert the tibial tray implant, one of more constraints may be imposed on the design of the outer surface of the one or more inferiorly-extending walls 8550 of the tibial tray 8500. For example, in the design and/or fabrication of the one or more inferiorly-extending walls 8550 of the tibial tray 8500 where the cortical bone underlying a resection plane defines an inner concave surface (e.g., inner concave surface 7016 in FIG. 35), the superior edge 7400 (FIG. 35) of the cortical bone 7012 (FIG. 35) along the resection plane RP1 (FIG. 35) may define a constraint so that the resulting outer surface 8554 of the inferiorly-depending wall 8550 is vertical or extends inwardly. In some embodiments, relative to an anatomic axis A (or other arbitrary axis or vertical reference) of the tibia 7000, horizontal distances d1 and d2 between the outer surface of the inferiorly-extending wall and the anatomic axis A may decrease from the proximal portion of the outer surface of the inferiorly-extending wall to the distal portion of the outer surface of the inferiorly-extending wall.

Figure 38:
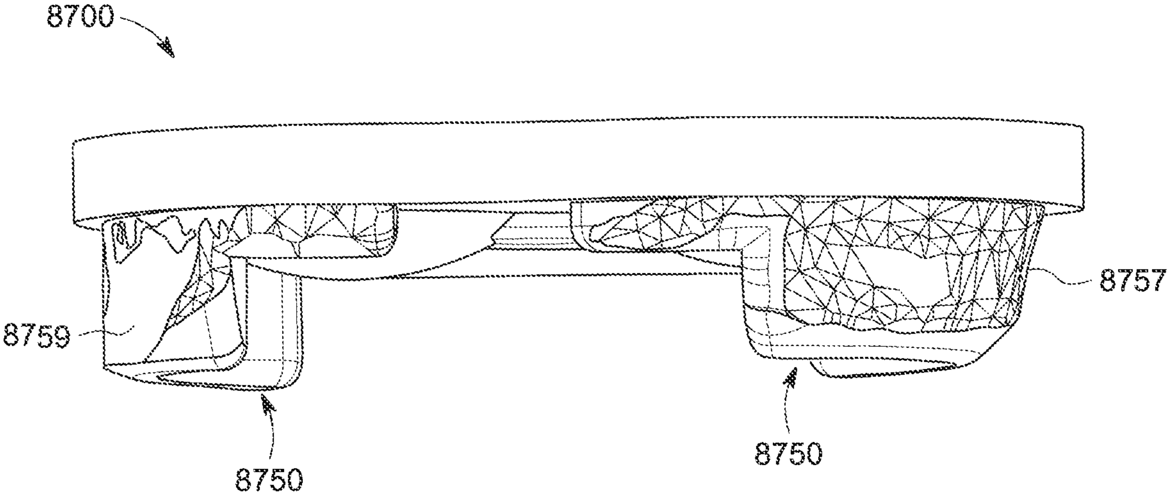
FIG. 38 is an elevational anterior view of a tibial tray for knee replacement, according to an embodiment of the present disclosure.

As shown in FIG. 38, a tibial tray 8700 may be designed and/or fabricated with constraints on the outer surface of the inferiorly-extending wall 8750 based on an underlying contoured cortical bone inner surface. For example, an outer surface portion 8757 of the inferiorly-extending wall 8750 may be configured to correspond to the shape of the underlying contoured cortical bone inner surface. Outer surface portion 8759 of the inferiorly-extending wall 8750 may be constrained by the superior edge 7400 (FIG. 35) of the cortical bone 7012 (FIG. 35) along the resection plane RP1 (FIG. 35) resulting in the outer surface portion 8759 having an outer vertical wall surface or a curved outer wall surface perpendicular to the bottom surface of the tibial tray.

In some embodiments, for example, for clinical reasons a resection plane may not be flat, but instead need to be disposed on an angle. If the implant was designed assuming a flat resection plane, but inserted onto an angled resection plane, clinical problems may be introduced. For example, the inferiorly-extending wall may not accurately correspond to the inner surface of a cortical wall and/or may even contact and/or penetrate the cortical bone.

Figure 39:
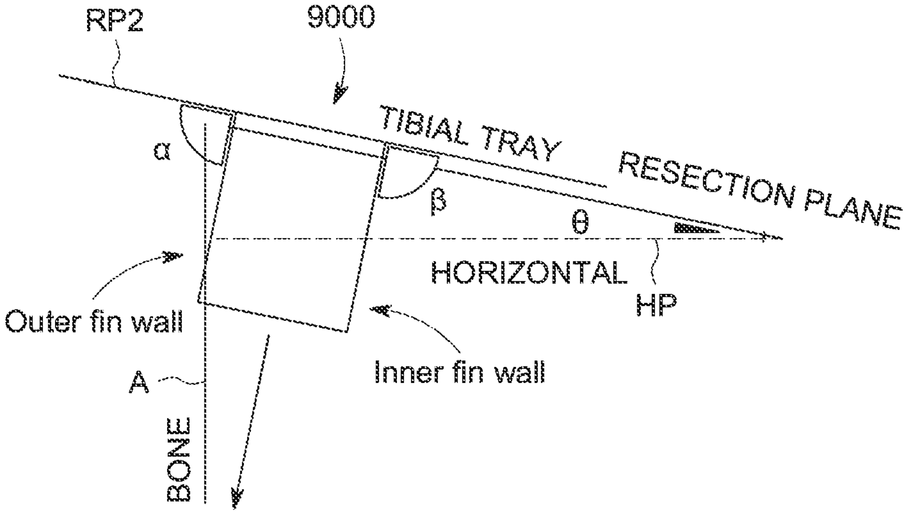
FIG. 39 is a diagrammatic illustration of a portion of a tibial tray, according to an embodiment of the present disclosure.

With reference to FIG. 39, in some embodiments, due to clinical reasons such as injury or disease, a resection plane RP2 may be required and designed and/or fabricated using the system 700 (FIG. 7) or system 800 (FIG. 8) to be on an angle, e.g., a resection plane RP2 may be resection plane that is positioned at a non-perpendicular angle to the anatomic axis A of the tibia. To compensate for this approach, a tibial tray 9000 design process may account for the angle of the resection plane relative to the anatomic axis A of the tibia, which angle may be determined pre-operatively by algorithms or program code and/or by a surgeon. In the event of an angled resection plane, the insertion calculations described above may be employed, but amended to account for the angle $\theta$, between the resection plane RP2 and a horizontal plane HP perpendicular to the anatomic axis A of the tibia. For example, angle $\theta$ may be added to angle $\alpha$ and angle $\beta$.

Figure 40:
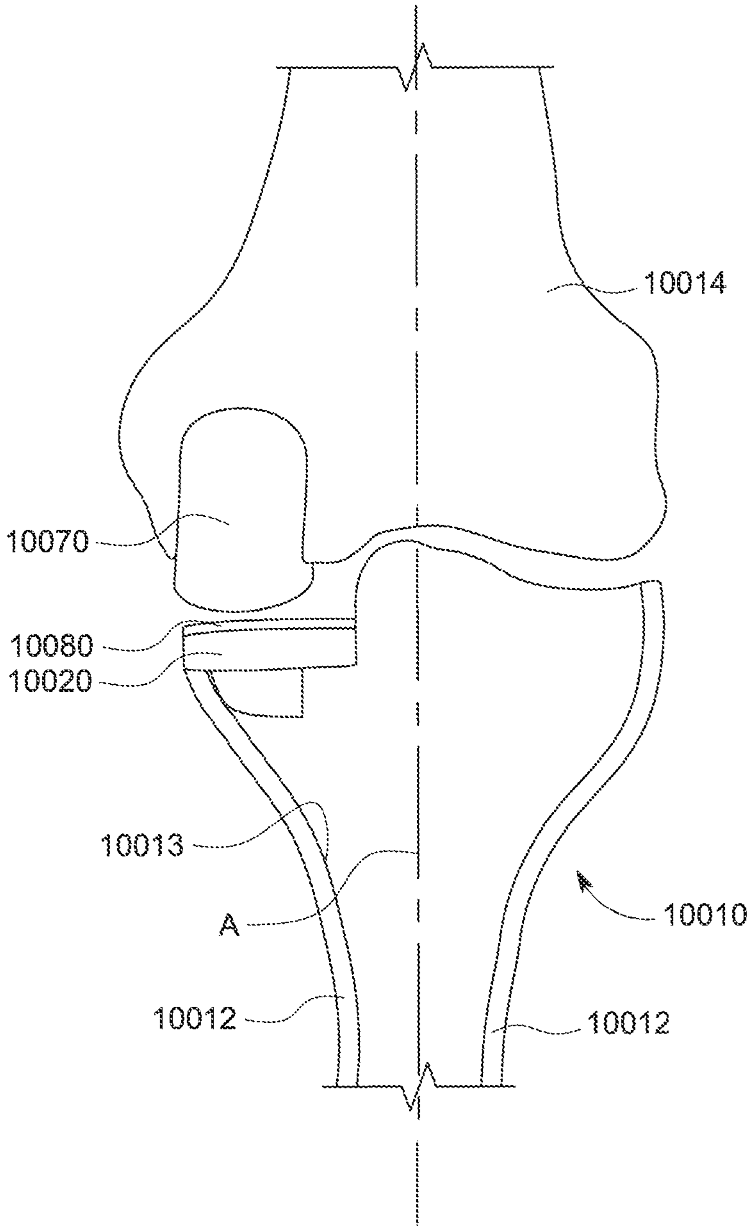
FIG. 40 is an anterior, in part cross-sectional, view of a distal portion of a femur and a partial resected proximal portion of a tibia of a patient, and a femoral component and a tibial tray for a partial knee replacement, according to an embodiment of the present disclosure.

FIG. 40 illustrates a tibial tray 10020 fitted to a partial resected proximal portion of a tibia 10010 for a partial knee replacement, according to an embodiment of the present disclosure. As illustrated, such a partial unicompartmental knee replacement (PUKR) replaces only a portion of a proximal portion of a damaged tibia as it leaves intact at least one of the natural bearing surfaces of the knee. For example, the tibial tray 10020 may replace either an inside (medial) part of a proximal tibia or an outside (lateral) part of a proximal part of a tibia. In this illustrated embodiment, at least a portion of the tibial tray 10020 when operably attached to the resected proximal portion of the tibia 10010 interfaces and increases contact with or may be spaced closely to an inner surface or side portion of the cortical bone 100012 of the proximal portion of the tibia 10010.

Figure 41:
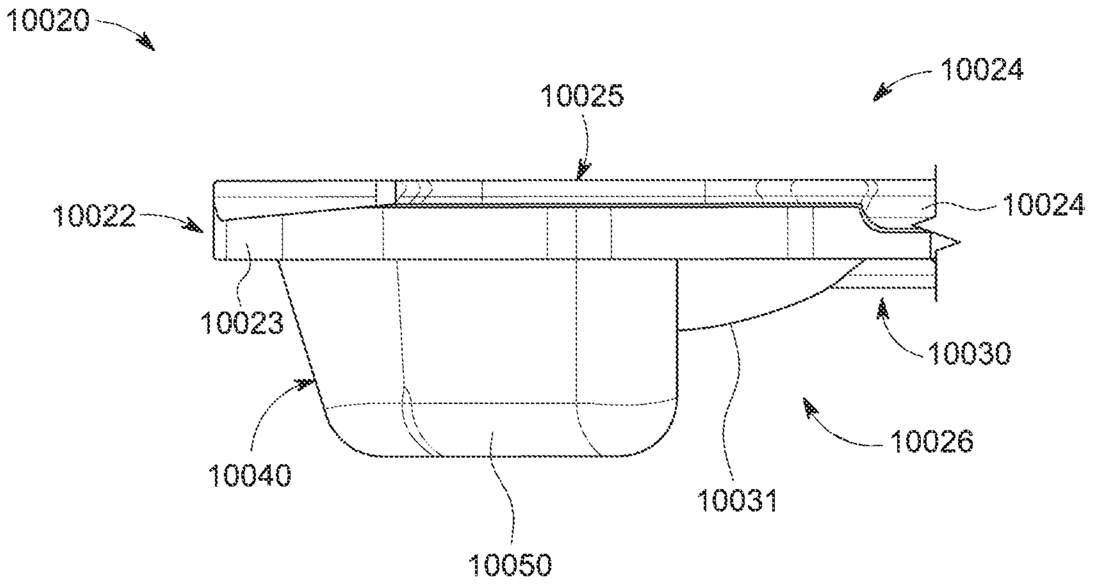
FIG. 41 is a side view of the tibial tray of FIG. 40, according to an embodiment of the present disclosure.
Figure 42:
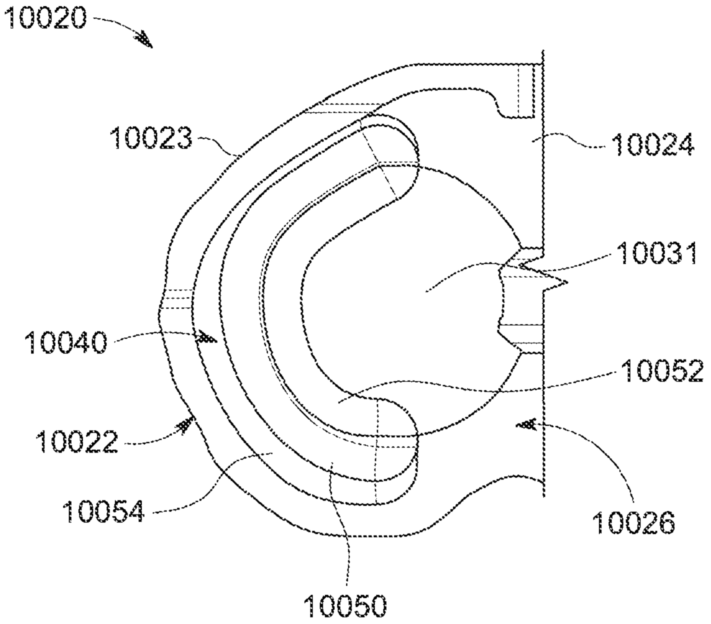
FIG. 42 is an inferior view of the tibial tray of FIG. 40, according to an embodiment of the present disclosure.

For example, as shown in FIGS. 41 and 42, the tibial tray 10020 may include a body 10022 having a superior portion 10024 (FIG. 41) and an inferior tibia-engaging portion 10026. The body 10022 may include a peripheral edge 10023 that corresponds to a portion of the outer surface of the cortical bone along the resected surface of the tibia, and a peripheral edge 10024 that spans across the center of the resected surface of the tibia. Peripheral edge 10024 may be disposed across the axis A (FIG. 40) of the tibia or spaced from the axis A (FIG. 40) of the tibia.

The superior portion 10024 may include a generally planar superior surface 10025 (FIG. 41) for supporting a plastic bearing spacer (not shown). In some embodiments, the planar superior surface 10025 may include a peripheral upwardly-extending lip (not shown) for attaching via a snap fit connection and restraining the plastic bearing spacer.

With reference again to FIG. 41, the tibia engaging portion 10026 may include a center tibia engaging portion 10030, and a peripheral tibia engaging portion 10040. In this embodiment, the center tibia engaging portion 10030 may include a surface contactable with a center cancellous bone surface of the resected proximal portion of the tibia of the patient. For example, the center tibia engaging portion may include one or more concave, convex, or planar surfaces contactable with the center cancellous bone surface of the partial resected proximal portion of the tibia of the patient as similarly described above. As illustrated in FIGS. 41 and 42, center tibia engaging portion 10030 may include a convex surface 10031. The convex undersurface may be designed to maximize surface area contact and reduce shear forces along the resection plane.

The peripheral tibia-engaging portion 10040 may include an inferiorly-extending wall 10050. The inferiorly-extending wall 10050 may include an inner wall surface 10052 (FIG. 42) and an outer wall surface 10054. For example, the wall surfaces 10052 and 10054 may be U-shaped walls. The wall 10050 may have a constant thickness, different thicknesses, varying thicknesses, or other suitable thicknesses. The inner wall surface 10052 may be disposed normal or at 90 degrees to the superior surface 10025, or at any suitable angle or angles. The outer wall surfaces 10054 may be disposed normal or at 90 degrees to the superior surface 10025. In other embodiments, the outer wall surface may be angled relative to the superior surface such as parallel with and spaced from an inner surface 10013 (FIG. 40) of the cortical bone 10012 (FIG. 40). As described above, outer wall surface 10054 may be configured to contact the inner surface of the cortical bone or may be configured to be closely spaced from the inner cortical bone.

As described above, various surgical robot methods may be employed for excavating the one or more cavities in the cancellous bone in the resected proximal portion of the tibia for insertion of the various tibial components as described above.

Figure 43:
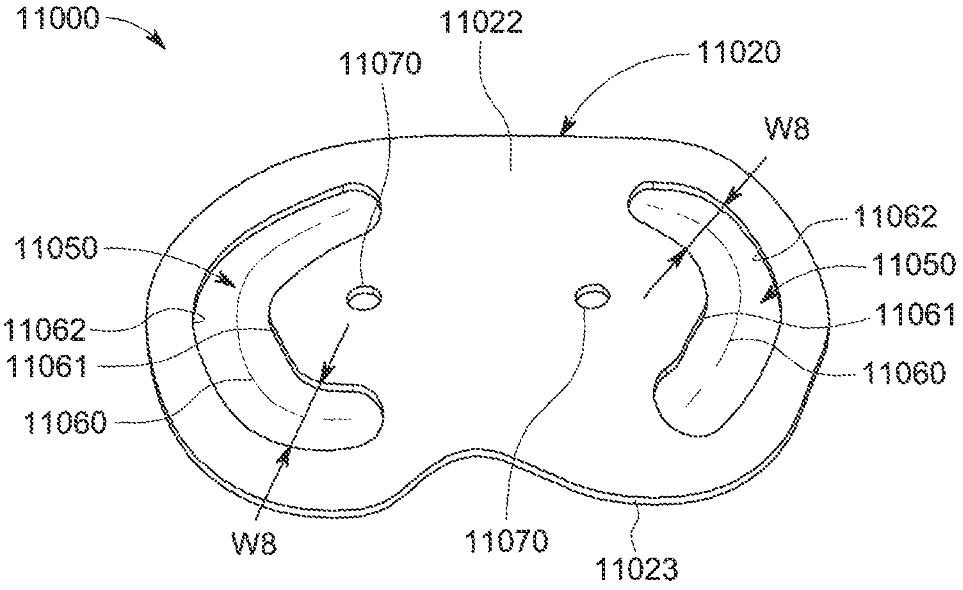
FIG. 43 is a superior perspective view of a tibia cavity cutting guide for the tibial tray of FIG. 40, according to an embodiment of the present disclosure.

FIG. 43 illustrates a patient-specific jig or tibia cavity cutting guide 11000 with openings 11050 to accommodate a non-robotic burr or milling tool 12000 (FIG. 44) to allow a surgeon to manually excavate the cavities as described above. For example, cutting guide 11000 may be used by a surgeon for forming at least one cavity in a resected proximal portion of a tibia of a patient for knee replacement. The resected proximal portion of the tibia includes a center cancellous bone surface and a peripheral cortical bone surface as described above. The cutting guide 11000 may include a planar member 11020 having a first planar surface 11022 and a second planar surface (not shown in FIG. 43).

Planar member 11020 may include a peripheral outer edge 11023, which corresponds to an outer peripheral cortical bone along the resected proximal portion of the tibial of the patient. A pair of U-shaped openings 11050 extends through the planar member from the first planar surface 11022 to the second planar surface (not shown) and is spaced from the peripheral outer edge. Each of the pair of U-shaped openings 11050 defines a U-shaped axis 11060, and the U-shaped opening has a constant width W8 normal to the U-shape axis. Width W8 desirably corresponds to the width of the inferiorly-extending portions of corresponding patient-specific tibial tray. Each of the pair of U-shaped openings have an inner edge 11061 and an outer edge 11062. The outer edge 11062 may be disposed parallel to the peripheral outer edge 11023. Cutting guide 11000 may be, for example, a patient-specific cutting guide and which may be effected using the system 700 of FIG. 7 and system 800 of FIG. 8. For example, suitable algorithms and programming code stored in memory 730 (FIG. 7) along with the patient tibia data 702 (FIG. 7) and the surgeon input 704 (FIG. 7) may be operably processed in processor 710 (FIG. 7) to generate a patient-specific cutting guide, which cutting guide may be produced or manufactured using 3D printer 795 (FIG. 7).

Figure 44:
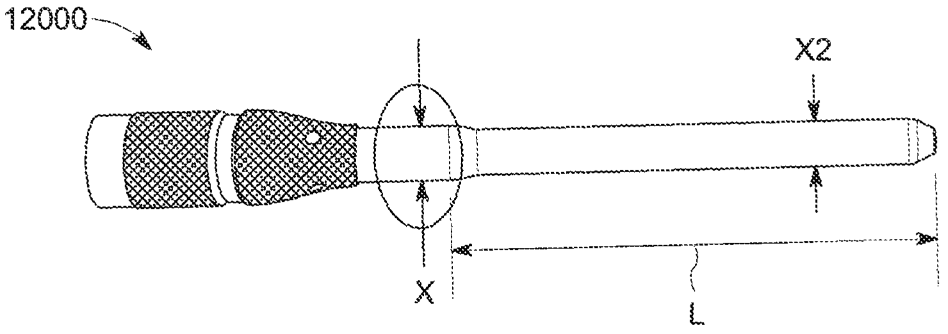
FIG. 44 is a perspective view of a milling tool, according to an embodiment of the present disclosure.

With reference to FIG. 44, the milling tool 12000 includes a proximal diameter X1 sized larger than the width W8 (FIG. 43) of U-shaped openings 11050, and a distal diameter X2 sized for passing through the width W8 of the U-shaped openings 11050. As such, patient-specific tibia cavity cutting guide 11000 (FIG. 43) with openings 11050 into which the milling tool 12000 fits, constrains movement of the milling tool 12000 in a fixed shape. With reference again to FIG. 43, cutting guide 11000 may include one or more fixing holes 11070 to accommodate temporary fixation, e.g., via screws, of the cutting guide to the resected tibia. The periphery of the cutting guide may be sized to match the outer periphery of the resected tibia such that visual alignment and proper placement on the resected tibia is readily performed.

With reference again to FIG. 44, a manual excavation of the cavities for the inferiorly-extending portions of the tibial tray may be made to the proper depth. For example, the cutting portion for of the milling guide 12000 may be sized to extend a length L that correspond to the depth of the inferiorly-extending portions of the tibial tray and to allow for receipt of the inferiorly-extending portions of the tibial tray when the tibial tray is placed on the resected proximal portion of the patient's tibia.

Figure 45:
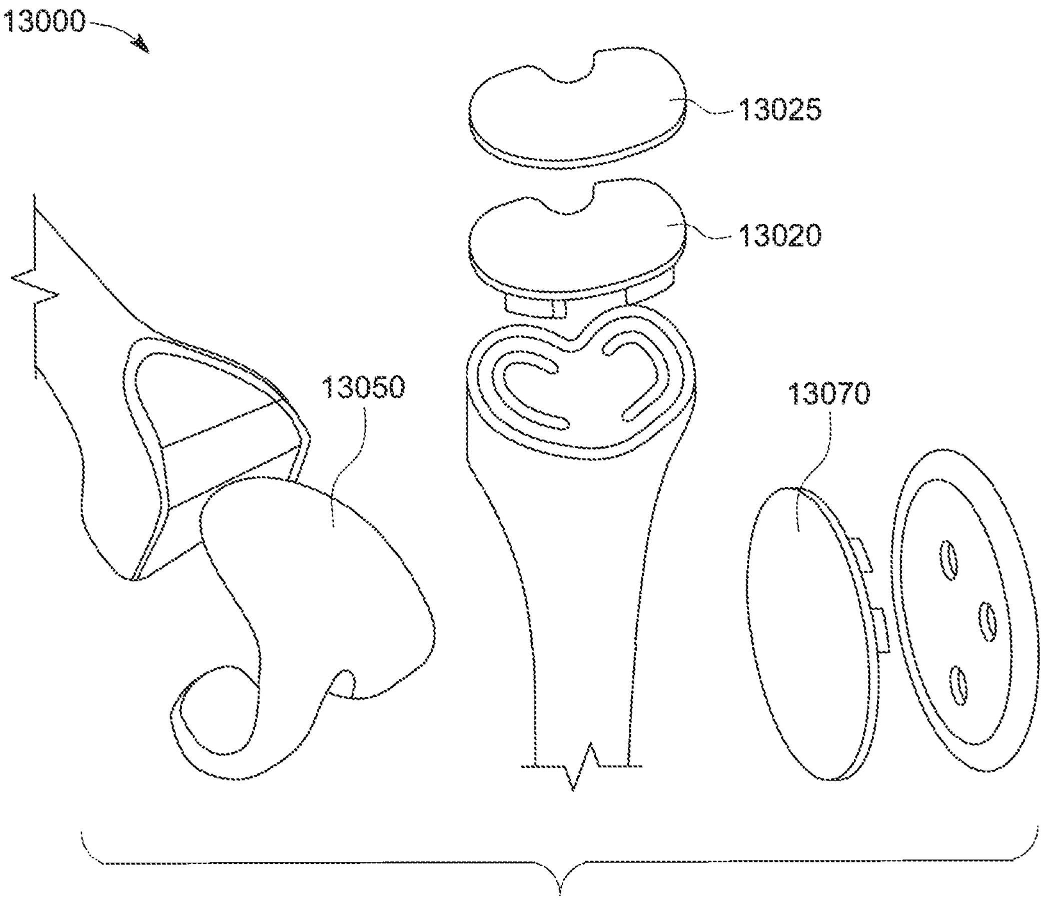
FIG. 45 are perspective views of the three components for a total knee replacement, according to an embodiment of the present disclosure.

FIG. 45 illustrates a patient-specific implant system 13000 for a total knee replacement, according to an embodiment of the present disclosure. For example, the patient-specific implant system 13000 may include a tibial tray 13020, such as configured and manufactured as described above, a spacer 13025, a femoral implant component 13050, and a patellar implant component 13070.

Figure 46:
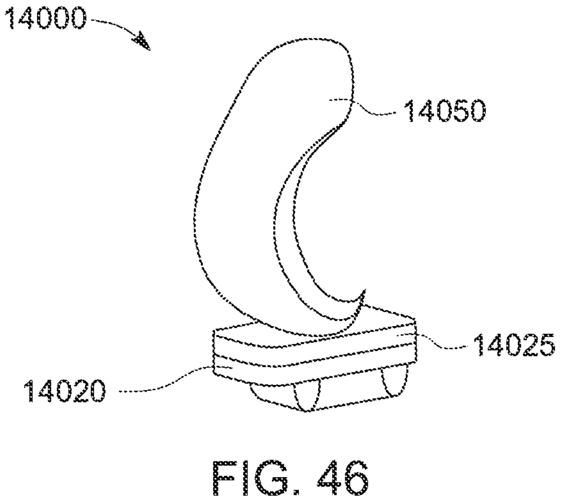
FIG. 46 is a perspective view of the components for a partial knee replacement, according to an embodiment of the present disclosure.

FIG. 46 illustrates a patient-specific implant system 14000 for a partial total knee replacement, according to an embodiment of the present disclosure. For example, the patient-specific implant system 14000 may include a partial tibial tray 14020, such as configured and manufactured as described above, a spacer 14025, and a partial femoral implant component 14050.

FIGS. 47-50 illustrate a tibial tray 15000, according to an embodiment of the present disclosure. For example, the tibial tray 15000 may be configured similar to tibial tray 2020 (FIGS. 26-28) with the exception of having a circumferential wall or fin 15040. Tibial tray 15000 may be installed on a resected proximal portion of a tibia in which the circumferential wall or fin 15040 is disposed closely adjacent to an underlying inner surface of the cortical bone for use in a total knee replacement.

In this illustrated embodiment, the tibial tray 15000 may include a body 15022 having a superior portion 15024 and an inferior tibia-engaging portion 15026. The superior portion 15024 may include a generally planar superior surface 15025 (best shown in FIG. 48) for supporting a plastic bearing spacer (not shown). In some embodiments, the planar superior surface 15025 may include a peripheral upwardly-extending lip (not shown) for attaching via a snap fit connection and restraining a plastic bearing spacer.

The inferior tibia-engaging portion 15026 may include the circumferential wall or fin 15040, which when operably attached to the resected proximal portion of a tibia 10 (FIG. 50) extends into the cancellous bone of the resected tibia. The circumferential wall or fin 15040 may be designed to be offset or spaced from the periphery of the underlying tibial cortical bone of the proximal portion of the tibia.

Figure 47:
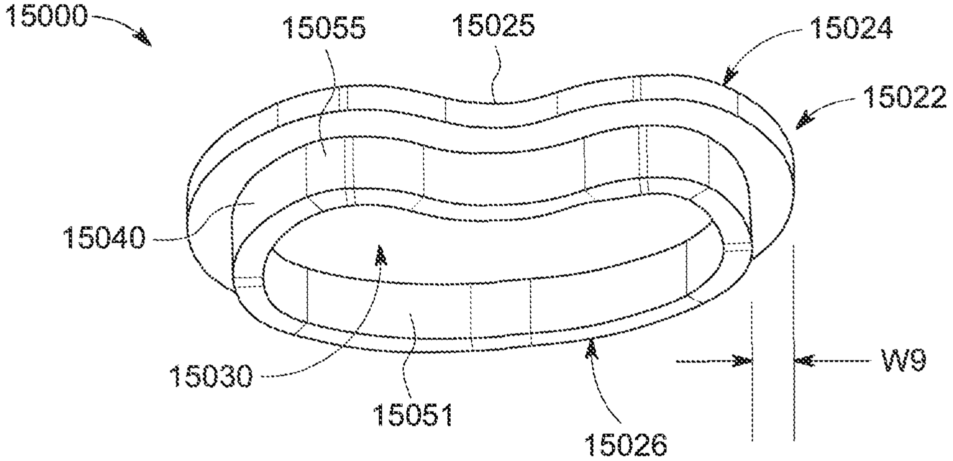
FIG. 47 is an inferior perspective view of a tibial tray, according to an embodiment of the present disclosure.
Figure 48:
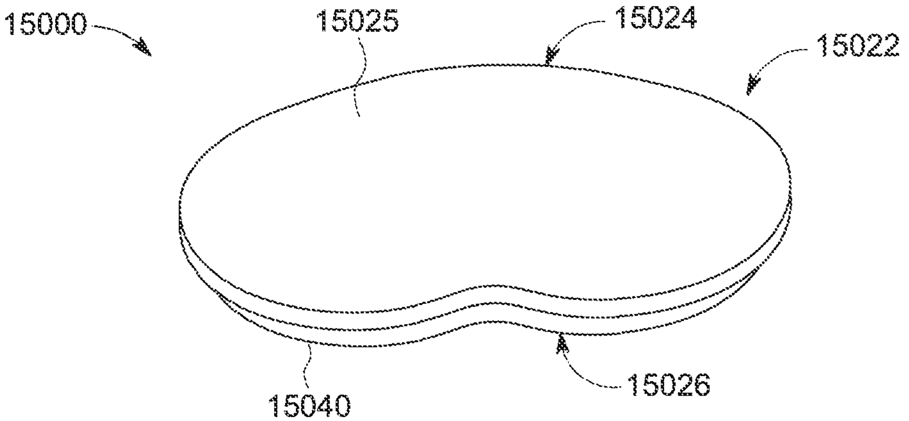
FIG. 48 is a superior perspective view of the tibial tray of FIG. 47, according to an embodiment of the present disclosure.
Figure 49:
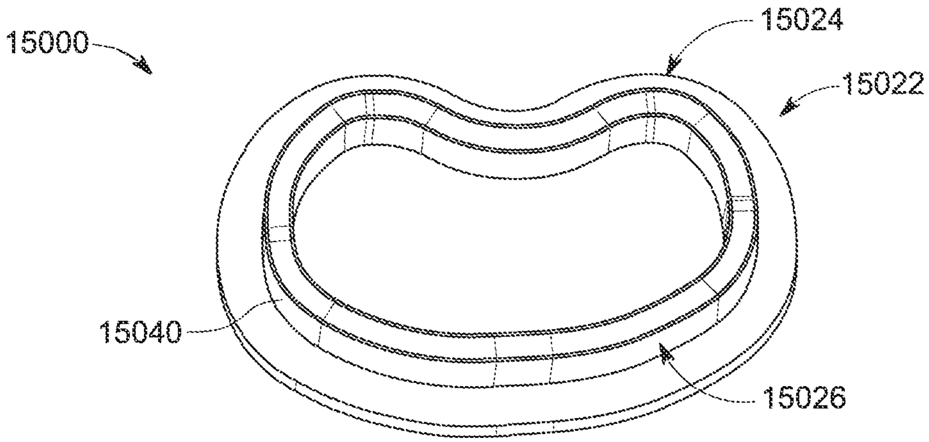
FIG. 49 is another inferior perspective view of the tibial tray of FIG. 47, according to an embodiment of the present disclosure.

As shown in FIG. 47, the tibia engaging portion 15026 may include a center tibia engaging portion 15030, and the single inferiorly-extending circumferential wall or fin 15040. In this embodiment, the center tibia engaging portion 15030 may include a flat surface contactable with the center cancellous bone surface of the resected proximal portion of the tibia of the patient. In other embodiments, the center tibia engaging portion may have a contoured surface as described above.

Figure 50:
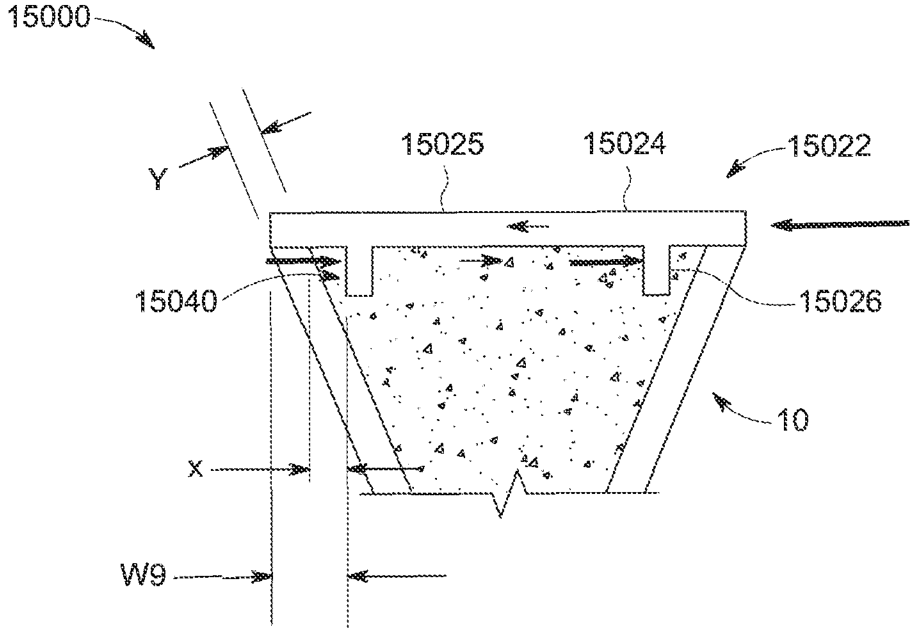
FIG. 50 is cross-sectional anterior view of a resected proximal portion of a tibia and the tibial tray of FIG. 47, according to an embodiment of the present disclosure.
Figure 51:
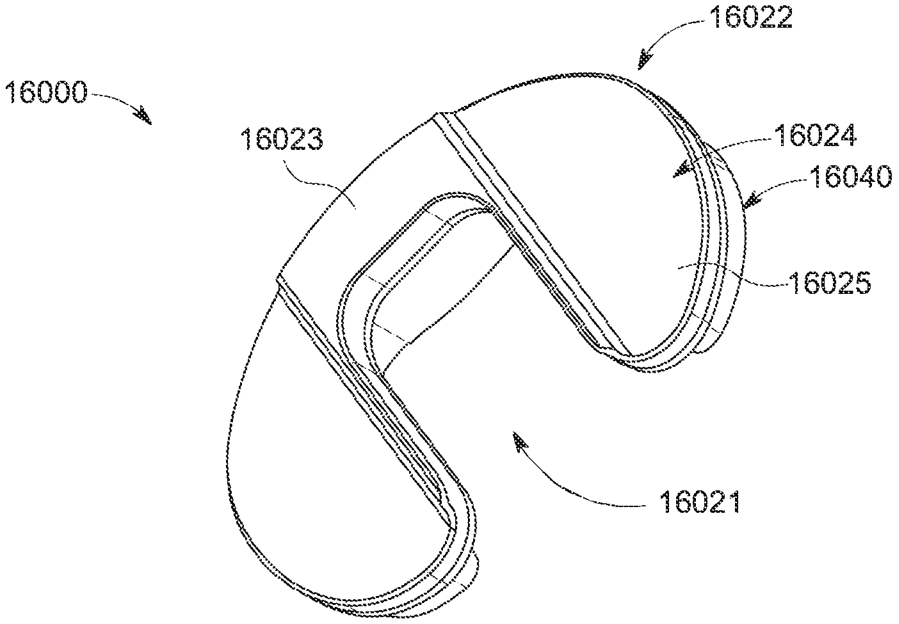
FIG. 51 is a superior perspective view of a tibial tray, according to an embodiment of the present disclosure.
Figure 52:
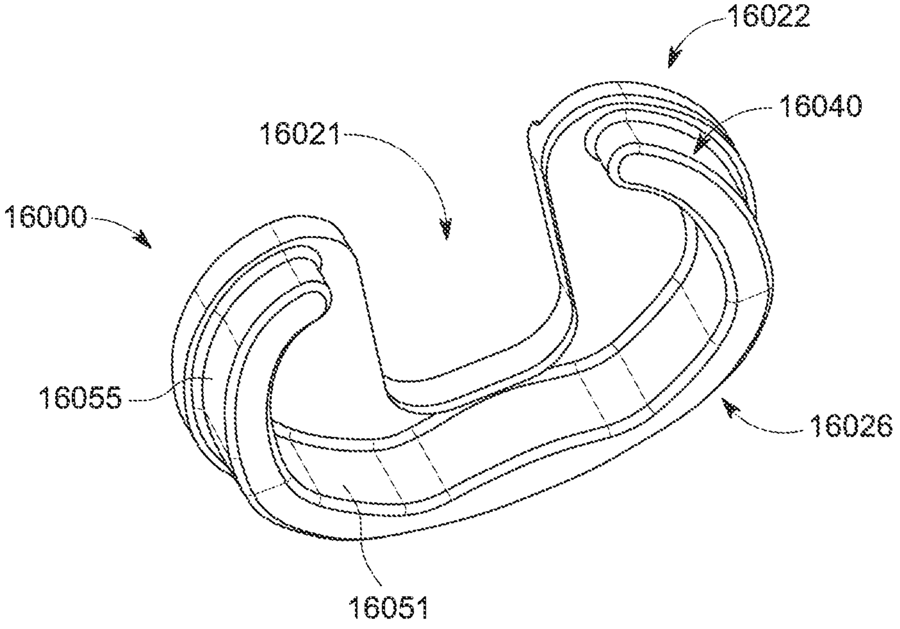
FIG. 52 is an inferior perspective view of the tibial tray of FIG. 51, according to an embodiment of the present disclosure.
Figure 53:
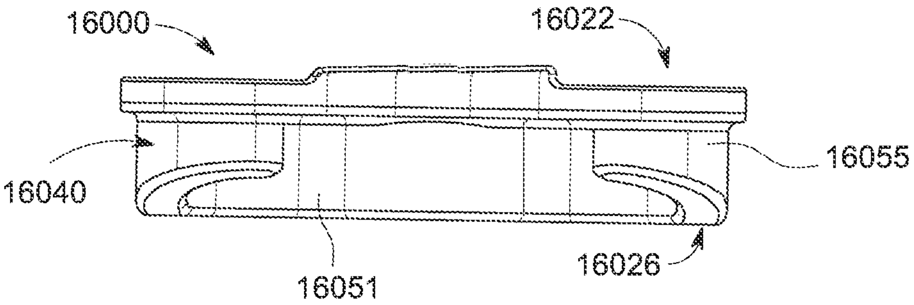
FIG. 53 is a posterior elevational view of the tibial tray of FIG. 51, according to an embodiment of the present disclosure.
Figure 54:
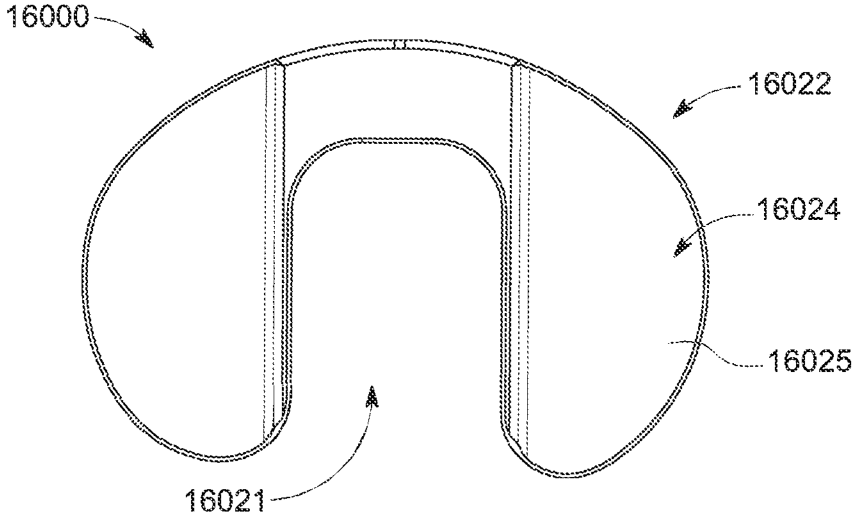
FIG. 54 is a superior view of the tibial tray of FIG. 51, according to an embodiment of the present disclosure.
Figure 55:
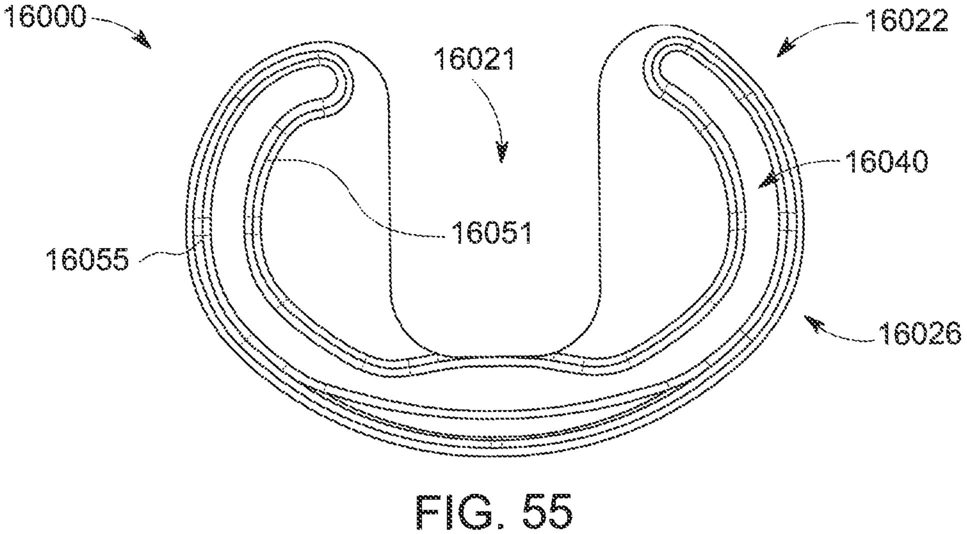
FIG. 55 is an inferior view of the tibial tray of FIG. 51, according to an embodiment of the present disclosure.
Figure 56:
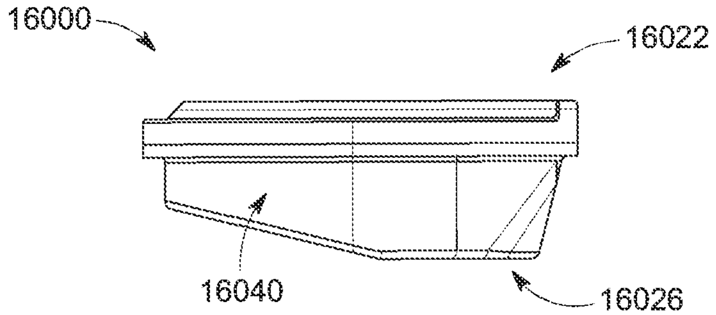
FIG. 56 is a side elevational view of the tibial tray of FIG. 51, according to an embodiment of the present disclosure.
Figure 57:
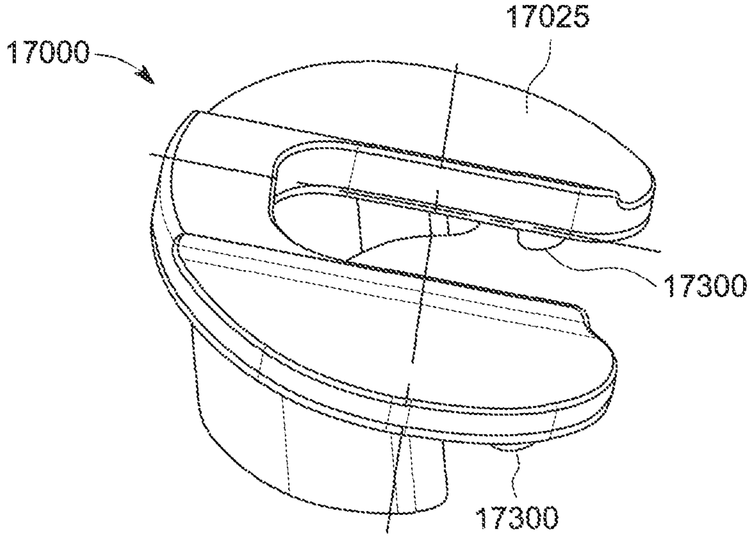
FIG. 57 is a superior perspective view of a tibial tray, according to an embodiment of the present disclosure.
Figure 58:
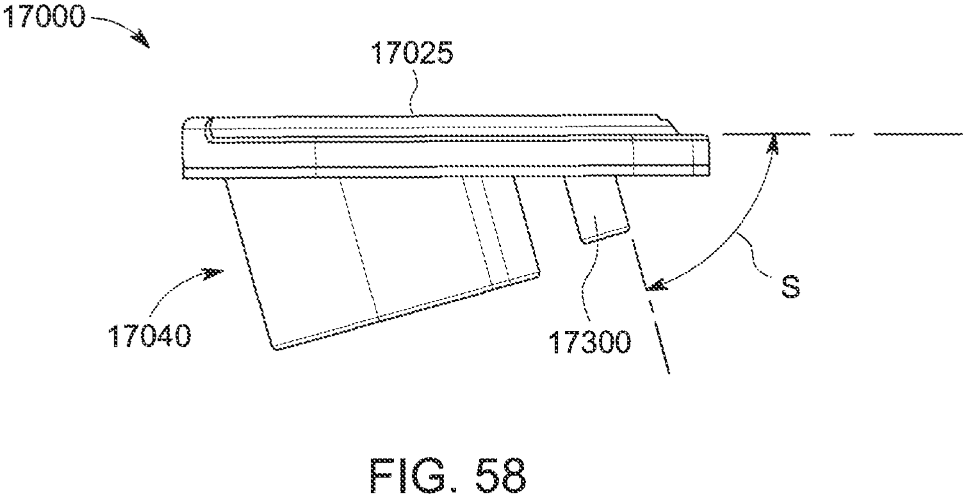
FIG. 58 is a side elevational view of the tibial tray of FIG. 57, according to an embodiment of the present disclosure.
Figure 59:
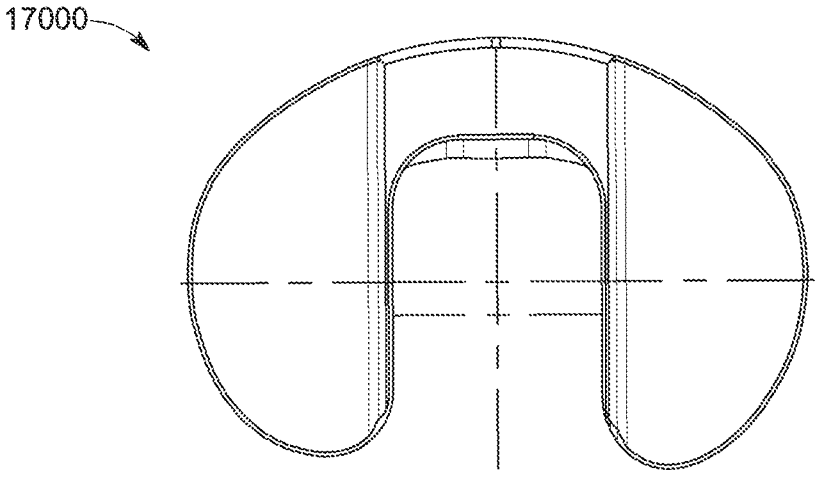
FIG. 59 is a superior view of the tibial tray of FIG. 57, according to an embodiment of the present disclosure.
Figure 60:
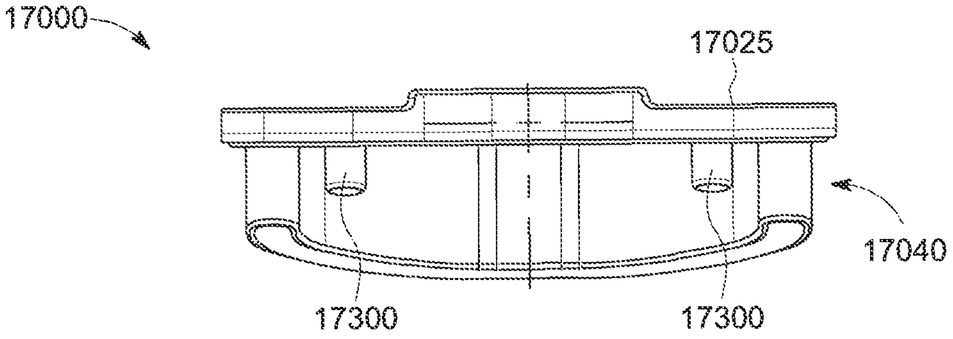
FIG. 60 is a posterior view of the tibial tray of FIG. 57, according to an embodiment of the present disclosure.
Figure 61:
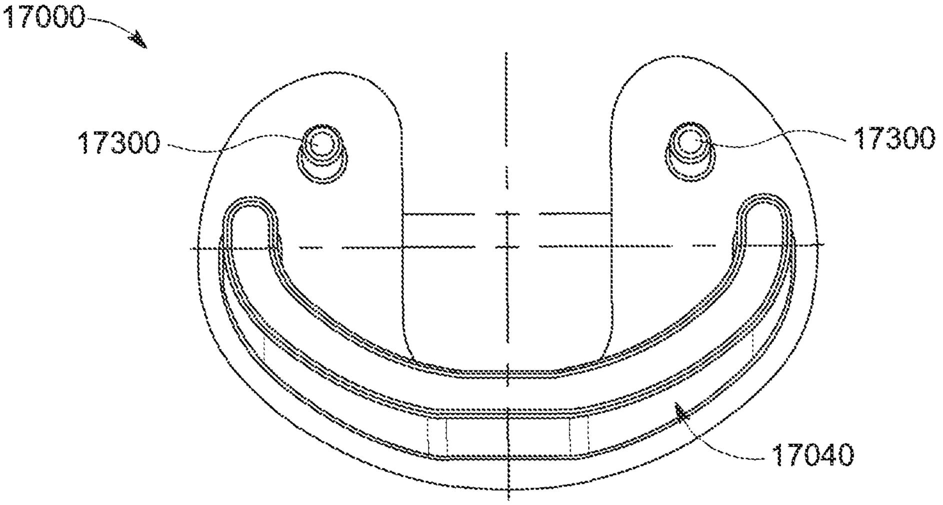
FIG. 61 is another inferior view of the tibial tray of FIG. 57, according to an embodiment of the present disclosure.

The single inferiorly-extending circumferential wall or fin 15040 may include an inner wall surface 15051 and an outer wall surface 15055. For example, the wall may have a cross-sectional kidney shape similar to the superior portion 15024. The superior portion 15024 may have constant thicknesses, different thickness, varying thickness, or other suitable thicknesses. The inner wall surface 15051 may be disposed normal or at 90 degrees to the superior surface 15025, or at any suitable angle or angles. The outer wall surface 15055 may be disposed normal or at 90 degrees to the superior surface 15025. In other embodiments, the outer wall surface may be angled relative to the superior surface such as parallel with and spaced from an inner surface of the cortical bone as shown in FIG. 50. In other embodiments, the outer wall surface 15055 may be configured to rest against the inner surface of the underlying cortical bone.

With reference again to FIG. 47, in this illustrated embodiment, the wall or fin 15040 may be circumferential and extend completely around and located towards a periphery of the implant or tibial tray undersurface or inferior surface 15030. The outer surface of the circumferential wall or fin may be based on pre-operative imaging data of the inner cortical wall of a patient, specifically to design the implant or tibial tray such that the fin outer wall is a fixed and a constant distance from the mapped inner surface of the cortical wall.

An implant ledge width W9 from the location of the mapped inner cortical wall and the location of the outer fin wall can be determined. With reference to FIG. 50, for example, an outer fin wall may be defined having a distance X from the inner cortical wall. A width Y, based on generally accepted pre-operative patient sample data for cortical wall thicknesses may allow designing an implant ledge W9 such that the width of the ledge is characterized by the formula:

$$W9=X+Y$$

For example, a distance X from the inner cortical wall to an outer fin wall may be defined as being 3 mm from the inner cortical wall at every point. The thickness of the cortical wall may be based on a patient's age. For example, a cortical wall thickness Y may be 2.2 mm for a certain age as predetermined based on, e.g., Gosman et al. "Development of Cortical Bone Geometry in the Human Femoral and Tibial Diaphysis", *The Anatomical Record,* 296 (5), 774-787, 2013. Thus, a tibial tray may be designed and configured having a ledge width W9 of 5.2 mm for example, from the exterior surface of the fin at every point along the periphery. The width Y may be variable based on anatomical observation or further study. For example, further research may find the average resected wall thickness is not uniform. For example, if the medial wall thickness is generally a value different from the lateral thickness, that information may be incorporated into the design of the tibial tray. In other embodiments of the present disclosure, a patient-specific design may employ a mapping of the inner cortical wall to design a patient-specific tibial tray having a matched wall or fin. An implant ledge width W9 may then be determined based on the mapped cortical wall thicknesses and a known distance of the wall or fin from the inner cortical wall.

With reference still to FIG. 50, in a total knee replacement an as indicated by the arrows in FIG. 50, a greater portion of a shearing force acting transversely on the tibial tray and the resected portion of the proximal portion of the tibia of the patient may be resisted by the at least one inferiorly-extending wall and the periphery of the resected proximal portion of the tibia compared to a portion of the shearing force being resisted along the center inferior surface of the tibial tray and the resected cancellous bone surface. In some embodiments, the greater portion may be greater than 50 percent, greater than 60 percent, greater than 70 percent, greater than 80 percent, greater than 90 percent, between 50 percent and 60 percent, between 50 percent and 70 percent, between 50 percent and 80 percent, between 50 percent and 90 percent, between 60 percent and 70 percent, between 70 percent and 80 percent, between 80 percent and 90 percent, between 60 percent and 80 percent, about 60 percent, about 70 percent, about 80 percent, about 90 percent, or other suitable parentage or range of percentages. In the other described and illustrated embodiments of the tibial trays in the present disclosure, such a shearing force may be similarly counteracted in a total knee replacement. Such embodiments may not include a center keel or may include a center keel such as a shallow keel, wherein such shearing force is primarily counteracted along the periphery of the resected proximal portion of the tibia of the patient.

FIGS. 51-56 illustrate a bi-cruciate tibial tray 16000, according to an embodiment of the present disclosure. For example, in a bi-cruciate retaining knee replacement both the anterior cruciate ligament (ACL) and posterior cruciate ligament (PCL) may be maintained. For example, this may be provided by bone resections and an implant geometry that circumvents these ligaments. The bi-cruciate tibial tray 16000 may include a circumferential or partially circumferential wall or fin. The lateral, anterior and medial fin walls are designed to abut or to be in close proximity to the inner cortical wall. The posterior portion of the implant undersurface may not feature a rim, or feature a rim that is generally inset from and designed to match the periphery of the posterior implant surface. The posterior implant surface is curved such that the anterior cruciate ligament (ACL) and posterior cruciate ligament (PCL) are maintained. In this illustrated embodiment, the tibial tray 16000 may include a U-shaped body 16022 having a U-shaped superior portion 16024 and a C-shaped inferior tibia-engaging portion 16026 (best shown in FIGS. 52 and 55). The U-shaped superior portion 16024 (FIGS. 51 and 54) may define portions (a lateral portion and a medial portion) defining a cavity 16021 therebetween. The superior portion 16024 may include a generally planar superior surface 16025 (best shown in FIGS. 51 and 54) for supporting a plastic bearing spacer (not shown). The superior portion 16024 may include a raised land or portion 16023 (best shown in FIG. 51) disposed between lateral portions for the superior portion 16024. In some embodiments, the planar superior surface 16025 may include a peripheral upwardly-extending lip (not shown) for attaching via a snap fit connection and restraining a plastic bearing spacer.

The inferior tibia-engaging portion 16026 may include the C-shaped wall or fin 16040, which when operably attached to the resected proximal portion of a tibia (not shown in FIGS. 51-56) extends into the cancellous bone of the resected tibia. The wall or fin 16040 may be designed to be offset or spaced from the periphery of the underlying tibial cortical bone of the proximal portion of the tibia.

The single inferiorly-extending C-shaped wall or fin 16040 may include an inner wall surface 16051 and an outer wall surface 16055. For example, the wall may have a cross-sectional shape similar to the cross-sectional U-shaped superior portion 16024 along with periphery thereof. The superior portion 16024 may have constant thicknesses, different thickness, varying thickness, or other suitable thicknesses. The inner wall surface 16051 may be disposed normal or at 90 degrees to the superior surface 16025, or at any suitable angle or angles. The outer wall surface 16055 may be disposed normal or at 90 degrees to the superior surface 16025. In other embodiments, the outer wall surface may be angled relative to the superior surface such as parallel with and spaced from an inner surface of the cortical bone (not shown in FIG. 51-56). In other embodiments, the outer wall surface 15055 may be configured to rest against the inner surface of the underlying cortical bone. The outer surface of the circumferential wall or fin 15055 may be based on pre-operative imaging data of the inner cortical wall of a patient, specifically to design the implant such that the fin outer wall is a fixed and a constant distance from the mapped inner surface of the cortical wall.

FIGS. 57-61 illustrate a bi-cruciate tibial tray 17000, according to an embodiment of the present disclosure. For example, in a bi-cruciate retaining knee replacement both the anterior cruciate ligament (ACL) and posterior cruciate ligament (PCL) may be maintained. For example, this may be provided by bone resections and an implant geometry that circumvents these ligaments. The bi-cruciate tibial tray 17000 may include a circumferential or partially circumferential wall or fin. The lateral, anterior and medial fin walls are designed to abut or to be in close proximity to the inner cortical wall. The posterior portion of the implant undersurface may: a) not feature a rim; or b) feature a rim that is generally inset from and designed to match the periphery of the posterior implant surface. The posterior implant surface is curved such that the anterior cruciate ligament (ACL) and posterior cruciate ligament (PCL) are maintained.

In this illustrated embodiment, the tibial tray 17000 may be essentially the same the bi-cruciate tibial tray 16000 (FIGS. 51-56) with the exception of a wall 17040 being disposed at an angle relative to a superior surface 17025 and being spaced from a plurality of inferiorly-extending projections or pins 17300. The wall 17040 and the pins 17300 may be dispose at a non-perpendicular angle S relative to the superior surface 17000 and to a medial-lateral direction. For example, angle S may be between about 70 degrees and 80 degrees, or may be about 75 degrees, or other suitable non-perpendicular angle.

During the insertion of a traditional style tibial baseplate with a post and fins, the tibia is subluxed in the anterior direction to a great extent to allow the post and fins to be prepared with a punch used from the superior direction. The tibia must remain subluxed anteriorly in order to place the tibial implant directly onto the resected tibia surface and seated in a directly inferior direction. In the embodiment of the tibial tray 17000, the wall and pegs are angled generally in the posterior direction to allow the implant to be inserted from the anterior side on an angle rather than directly down from the superior direction. This may allow the surgeon to sublux the tibia anteriorly less than in some traditional systems in order to insert the tibial baseplate, which may cause less soft tissue damage due to extreme subluxation of the tibia.

Figure 62:
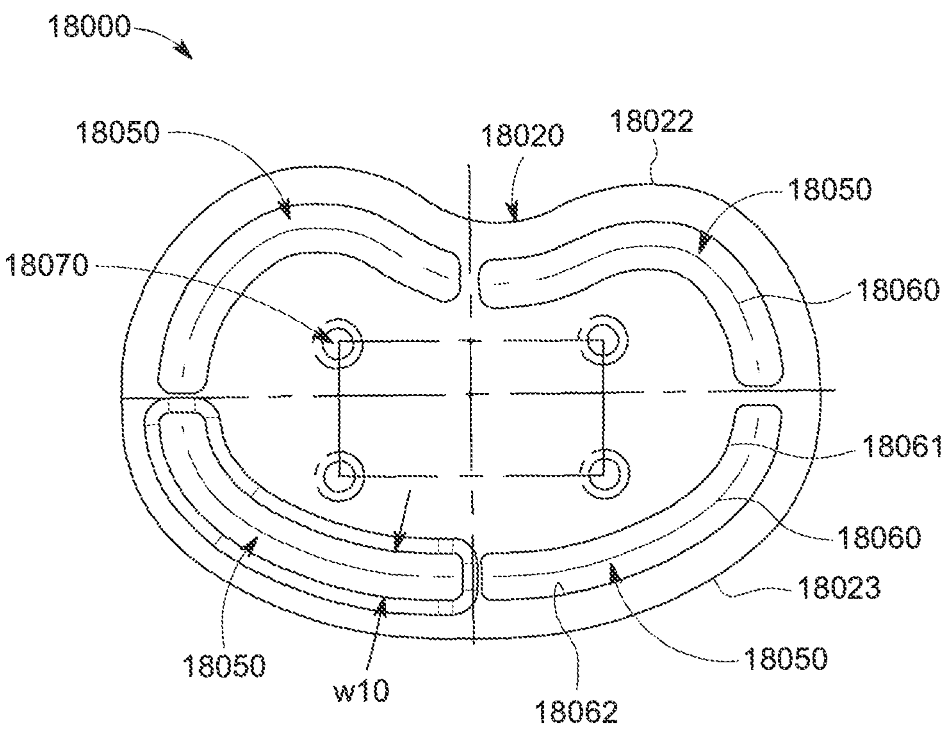
FIG. 62 is a superior perspective view of a tibia cavity cutting guide for the tibial tray of FIG. 47, according to an embodiment of the present disclosure.

FIG. 62 illustrates a patient-specific jig or tibia cavity cutting guide 18000 with a series of openings 18050 to accommodate a non-robotic burr or milling tool 12000 (FIG. 44) to allow a surgeon to manually excavate the cavities as described above. For example, cutting guide 18000 may be used by a surgeon for forming at least one cavity such as a continuous cavity in a resected proximal portion of a tibia of a patient for knee replacement. The resected proximal portion of the tibia includes a center cancellous bone surface and a peripheral cortical bone surface as described above. The cutting guide 18000 may include a planar member 18020 having a first planar surface 18022 and a second planar surface (not shown in FIG. 62).

Planar member 18020 may include a peripheral outer edge 18023, which corresponds to an outer peripheral cortical bone along the resected proximal portion of the tibial of the patient. A series curved openings 18050 extends through the planar member from the first planar surface 18022 to the second planar surface (not shown) and is spaced from the peripheral outer edge. Each of the openings 18050 defines an axis 18060, and the opening has a constant width W10 normal to the axis. The width desirably corresponds to the width of the inferiorly-extending portions of corresponding patient-specific tibial tray. Each of the openings have an inner edge 18061 and an outer edge 18062. The outer edge 18062 may be disposed parallel to the peripheral outer edge 18023. The cutting guide 18000 may include one or more fixing holes 18070 to accommodate temporary fixation, e.g., via screws, of the cutting guide to the resected tibia. The periphery of the cutting guide may be sized to match the outer periphery of the resected tibia such that visual alignment and proper placement on the resected tibia is readily performed.

Cutting guide 18000 may be, for example, a patient-specific cutting guide and which may be effected using the system 700 of FIG. 7 and system 800 of FIG. 8. For example, suitable algorithms and programming code stored in memory 730 (FIG. 7) along with the patient tibia data 702 (FIG. 7) and the surgeon input 704 (FIG. 7) may be operably processed in processor 710 (FIG. 7) to generate a patient-specific cutting guide, which cutting guide may be produced or manufactured using 3D printer 795 (FIG. 7).

The cutting guide 18000 may be operable with a milling tool such as the milling tool 12000 (FIG. 44). As such, patient-specific tibia cavity cutting guide 18000 with openings 18050 into which the milling tool 12000 fits, constrains movement of the milling tool 1200 in a fixed shape. A manual excavation of the at least one cavity for the inferiorly-extending portions of the tibial tray may be made to the proper depth. For example, the cutting portion for of the milling guide 12000 (FIG. 44) may be sized to extend a length L (FIG. 44) that correspond to the depth of the inferiorly-extending portion of the tibial tray and to allow for receipt of the inferiorly-extending portion of the tibial tray when the tibial tray is placed on the resected proximal portion of the patient's tibia. As will be appreciated, the cutting guide 18000 may be removed and the remaining portions between the series of cavities may be removed by aa surgeon to compete the continuous cavity in the resected portion of the proximal portion of the tibia of the patient.

Figure 63:
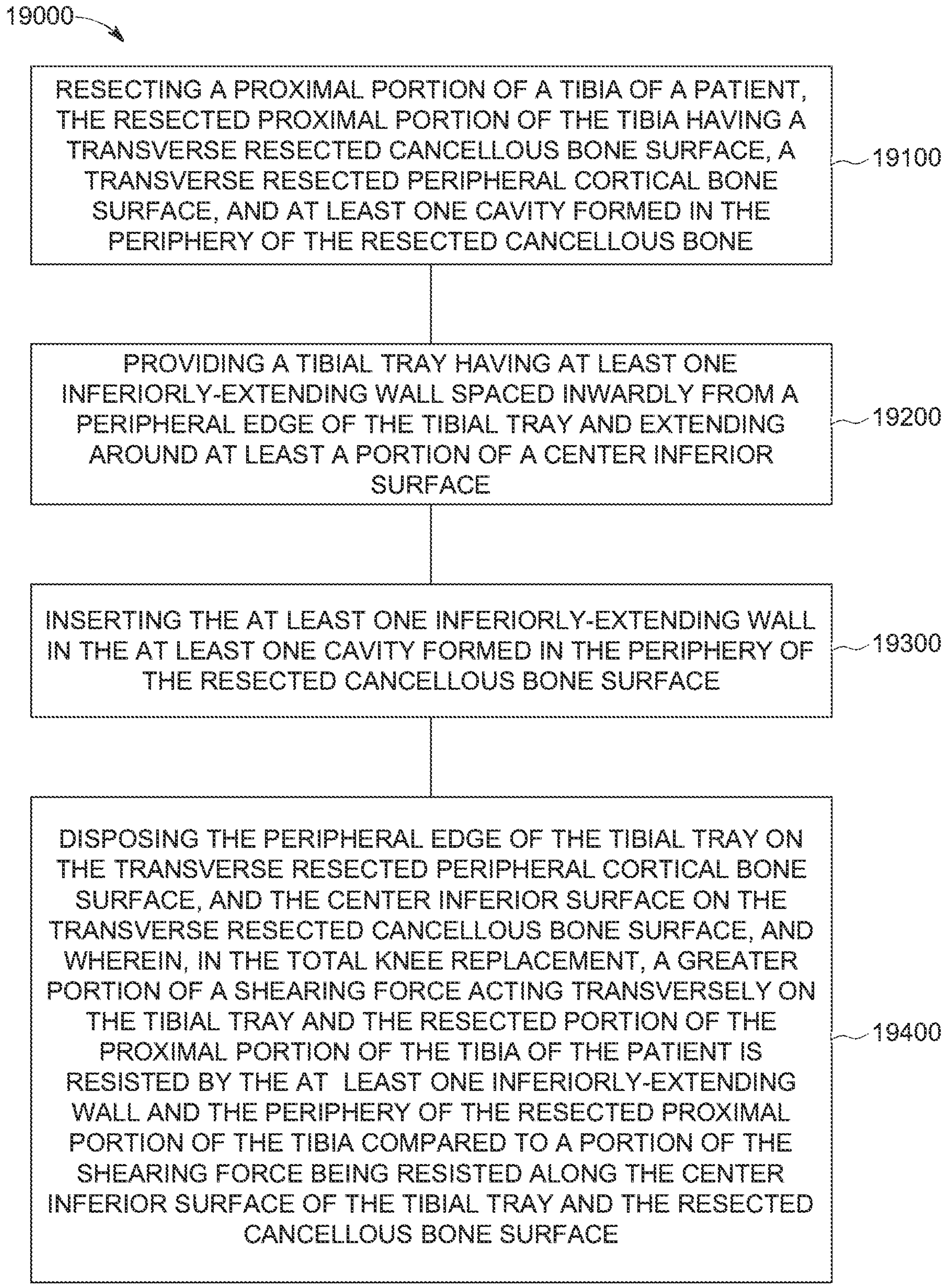
FIG. 63 is a flowchart of a method, according to an embodiment of the present disclosure.

FIG. 63 illustrates a block diagram of a method 19000 for use in a total knee replacement. The method 19000 includes, for example, at 19100 resecting a proximal portion of a tibia of a patient, the resected proximal portion of the tibia having a transverse resected cancellous bone surface, a transverse resected peripheral cortical bone surface, and at least one cavity formed in the periphery of the resected cancellous bone, at 19200 providing a tibial tray having at least one inferiorly-extending wall spaced inwardly from a peripheral edge of the tibial tray and extending around at least a portion of a center inferior surface, at 19300 inserting the at least one inferiorly-extending wall in the at least one cavity formed in the periphery of the resected cancellous bone surface, at 19400 disposing the peripheral edge of the tibial tray on the transverse resected peripheral cortical bone surface, and the center inferior surface on the transverse resected cancellous bone surface, and wherein, in the total knee replacement, a greater portion of a shearing force acting transversely on the tibial tray and the resected portion of the proximal portion of the tibia of the patient is resisted by the at least one inferiorly-extending wall and the periphery of the resected proximal portion of the tibia compared to a portion of the shearing force being resisted along the center inferior surface of the tibial tray and the resected cancellous bone surface.

It will be appreciated from the technique of the present disclosure for the tibial trays and the resected proximal portion of the tibia may overcome the problems of conventional non-patient-specific tibial trays that are designed to rest on a flat resection plane that minimizes surface area contact and maximizes shear forces, lack redundant modes of support, provide poor implant surface area coverage influencing the risk of subsidence. The patient-specific tibial trays and patient-specific resected proximal portion of the tibia overcome the problems associated with conventional tibial trays, which conventional tibial trays are designed as geometric approximations of multiple bone models that are manually segmented from large image databases and proportionally constrained and scaled to accommodate a range of sizes and resecting of the proximal portion of the tibia being flat cut often using a sagittal saw.

The technique of the present disclosure may provide increased surface area contact and/or reduced shear forces along the resection plane of the implant-to-bone interface resulting in less failures or loosening by poor alignment and natural lateral loading of the joint.

The algorithms of the present disclosure may be operable to generate a patient-specific tibial tray and robotic cut path of the proximal portion of the tibia that solves the primary failures modes of press-fit tibial knee implants by restoring the pre-operative anatomy and specifically 1) maximizing the surface area contact for increased osseointegration, 2) reducing shear forces and localizing forces to either side of the intercondylar eminence, 3) maximizing cortical contact at the periphery of the implant, and 3) minimizing subsidence and increasing stability with patient-specific support pins.

A1. A tibial tray for a resected proximal portion of a tibia of a patient for a total knee replacement. The resected proximal portion of the tibia has a center cancellous bone surface, a peripheral cortical bone surface, and at least one cavity formed in the periphery of the cancellous bone spaced apart from the cortical bone exposing an underlying portion of the cancellous bone of the tibia. The tibial tray may include a body having a superior portion with a superior surface, and an inferior tibia-engaging portion. The body may include an inferior tibia-engaging portion having a center portion having a center surface contactable with the center cancellous bone surface, and a peripheral, inferiorly-extending portion receivable in the at least one cavity formed in the cancellous bone surface so that the peripheral inferiorly-extending portion is spaced apart from the underlying inner surface of the cortical bone of the tibia of the patient.

A2. The tibial tray of A1, wherein the inferior tibia-engaging portion comprises a peripheral edge portion having an inferior surface supportable on the peripheral cortical bone surface of the tibia of the patient, and the peripheral, inferiorly-extending portion being disposed inwardly of the peripheral edge portion. A3. The tibial tray of A1 or A2, wherein the center surface of the inferior tibia-engaging portion comprises a non-planar surface. A4. The tibial tray of any of A1 through A3, wherein the inferiorly-extending portion of the inferior tibia-engaging portion is extendable around at least 10 percent of a perimeter of the underlying peripheral inner surface of the cortical bone of the tibia of the patient. A5. The tibial tray of any of A1 through A4, wherein the inferior tibia-engaging portion comprises an inferior convex surface, an inferior concave surface, and/or an inferior convex surface and an inferior concave surface. A6. The tibial tray of any of A1 through A5, wherein the inferior tibia-engaging portion comprises a pair of spaced-apart inferior convex surfaces corresponding in size to a medial condyle and a lateral condyle of the proximal portion of the tibia of the patient. A7. The tibial tray of any of A1 through A6, wherein the peripheral, inferiorly-extending portion comprises a wall spaced apart from the inner surface of the cortical bone. A8. The tibial tray of A7, wherein the wall comprises a surface configured to be spaced apart from the underlying inner surface of the cortical bone, is angled at about 35 degrees relative to the superior surface of the superior portion of the body, and extends about 7 mm below the superior surface of the superior portion of the body. A9. The tibial tray of any of A7 or A8, wherein the wall extends along at least 30 percent of a perimeter of the underlying peripheral cancellous bone of the tibia of the patient. A10. The tibial tray of any of A7 through A9, wherein the wall extends along the entire peripheral portion of the body. A11. The tibial tray of any of A1 through A10, wherein the inferiorly-extending portion comprises a pair of curved walls configured to be spaced apart from the inner surface the cortical bone. A12. The tibial tray of any of A1 through A11, wherein the inferiorly-extending portion comprises a pair of curved walls configured to be spaced apart from the inner surface the cortical bone, and the center surface comprises a pair of spaced-apart inferior convex surfaces corresponding in size to a medial condyle and a lateral condyle of the proximal portion of the tibia of the patient.

A13. The tibial tray of any of A1 through A12, wherein the peripheral inferiorly-extending portion defines a constant gap between the peripheral inferiorly-extending portion and an inner surface of the cortical bone. A14. The tibial tray of any of A1 through A13, wherein the center portion of the body comprises an inferiorly-extending keel. A15. The tibial tray of any of A1 through A14, wherein the body comprises a one-piece body.

B1. A method for forming a patient-specific tibial tray for a total knee replacement of the patient, the method comprising: determining a patient-specific resected proximal portion of a tibia of the patient, the resected proximal portion of the tibia of the patient having a center cancellous bone surface, a peripheral cortical bone surface, and at least one cavity formed in the periphery of the cancellous bone spaced apart from the cortical bone exposing an underlying portion of the cancellous bone of the tibia; and forming the patient-specific tibial tray comprising a body having a superior portion having a superior surface and an inferior tibia-engaging portion, the inferior tibia engaging portion having a center portion contactable with the center cancellous bone surface, and a peripheral, inferiorly-extending portion receivable in the at least one cavity so that the peripheral inferiorly-extending portion is spaced apart from the underlying inner surface of the cortical bone of the tibia of the patient.

B2. The method of B1 further comprising, obtaining first data, via a processor, representing a proximal portion of the tibia of the patient, and determining, via the processor, second data corresponding the patient-specific resected proximal portion of the tibia of the patient based on the first data, and the forming, via the processor, comprises 3D printing, forging, casting based on the second data. B2. The method of B1, wherein the obtaining first data comprises obtaining CT scan data and/or X-rays, and the determining comprises determining the patient-specific resected proximal portion of the tibia of the patient based on the obtained first data. B3. The method of B1 or B2 further comprising, maximizing the size and shape of the inferior tibia-engaging portion based on a depth and an amount extending along the periphery of the underlying cancellous bone. B20. The method of and of B17 through B19 further comprising, reducing shear forces and localized forces based on the implant to bone contact plane based on the equation Fx=Fcos(theta).

C1. A tibial tray for a resected proximal portion of a tibia of a patient for a total knee replacement, the resected proximal portion of the tibia having a central cancellous bone surface, a peripheral cortical bone surface, and at least one cavity formed in the periphery of the cancellous bone. The tibial tray comprising a body the body comprising a superior portion with a superior surface; and an inferior tibia-engaging portion. The inferior tibia-engaging portion comprises a center portion having a center surface contactable with the central cancellous bone surface, and a peripheral, inferiorly-extending portion receivable in the at least one cavity formed in the cancellous bone surface so that the peripheral inferiorly-extending outer surface portion corresponds to the contour of the underlying inner surface of the cortical bone of the tibia of the patient.

C2. The tibial tray of C1, wherein the peripheral, inferiorly-extending portion comprises at least a portion of the peripheral inferiorly-extending outer surface portion extending from a proximal portion of the peripheral, inferiorly-extending portion to a distal portion of the peripheral, inferiorly-extending portion contoured to correspond to a contour of a superior edge portion of the cortical bone along the resection plane so that the at least the portion of the peripheral inferiorly-extending outer surface portion is disposable adjacent to a underlying concave inner surface of the cortical bone. C3. The tibial tray of C2, wherein the contour of the at least the portion of the peripheral inferiorly-extending outer surface portion from the proximal portion to the distal portion of the peripheral, inferiorly-extending portion is perpendicular to the resection plane. C4. The tibial tray of C1, wherein the peripheral, inferiorly-extending portion comprises at least a portion of the peripheral inferiorly-extending outer surface portion extending from a proximal portion of the peripheral, inferiorly-extending portion to a distal portion of the peripheral, inferiorly-extending portion having a proximal portion contoured to correspond to a contour of a superior edge portion of the cortical bone along the resection plane, and a distal portion contoured to being disposable inwardly from the contour of the superior edge portion of the cortical bone along the resection plane.

D1. A tibial tray for a resected proximal portion of a tibia of a patient for a knee replacement, the resected proximal portion of the tibia having a center cancellous bone surface, a peripheral cortical bone surface, and at least one cavity formed in the cancellous bone exposing at least a portion of an underlying inner surface of the cortical bone. The tibial tray includes a body comprising a superior portion with a superior surface; and an inferior tibia-engaging portion. The inferior tibia-engaging portion comprises a center portion having a center surface contactable with the center cancellous bone surface, and a peripheral, inferiorly-extending portion receivable in the at least one cavity formed in the cancellous bone surface, a surface of the peripheral inferiorly-extending portion contactable with the exposed underlying inner surface of the cortical bone of the tibia of the patient.

D2. The tibial tray of D1 wherein the inferior tibia-engaging portion comprises: a peripheral edge portion having an inferior surface supportable on the peripheral cortical bone surface of the tibia of the patient, and the peripheral, inferiorly-extending portion being disposed inwardly of the peripheral edge portion. D3. The tibial tray of D1 wherein the center surface of the inferior tibia-engaging portion comprises a non-planar surface. D4. The tibial tray of D1 wherein the surface of the inferiorly-extending portion of the inferior tibia-engaging portion is contactable with at least 10 percent of a perimeter of the underlying peripheral inner surface of the cortical bone of the tibia of the patient. D5. The tibial tray of D1 wherein the inferior tibia-engaging portion comprises an inferior convex surface, an inferior concave surface, and/or an inferior convex surface and an inferior concave surface. D6. The tibial tray of D1 wherein the inferior tibia-engaging portion comprises a pair of spaced-apart inferior convex surfaces corresponding in size to a medial condyle and a lateral condyle of the proximal portion of the tibia of the patient. D7. The tibial tray of D1 wherein the peripheral, inferiorly-extending portion comprises a wall contactable against the exposed inner surface of the cortical bone. D8. The tibial tray of D7 wherein the wall comprises the surface contactable with the exposed underlying inner surface of the cortical bone and is angled at about 35 degrees relative to the superior surface of the superior portion of the body and extending about 7 mm below the superior surface of the superior portion of the body. D9. The tibial tray of D7 wherein the wall extends along at least 30 percent of a perimeter of the underlying peripheral inner surface of the cortical bone of the tibia of the patient. D10. The tibial tray of D7 wherein the wall extends along the entire center portion of the body. D11. The tibial tray of D1 wherein the inferiorly-extending portion comprises a pair of curved walls contactable against spaced apart portions of the inner surface the cortical bone. D12. The tibial tray of D1 wherein the inferiorly-extending portion comprises a pair of curved walls contactable against spaced apart portions of the inner surface the cortical bone, and the center surface comprises a pair of spaced-apart inferior convex surfaces corresponding in size to a medial condyle and a lateral condyle of the proximal portion of the tibia of the patient. D13. The tibial tray of D1 wherein the inferiorly-extending portion comprises at least one inferiorly-extending pin extendable through an aperture in the inner cortical bone and having an edge alignable with an outer surface of the cortical bone. D14. The tibial tray of D1 wherein the center portion of the body comprises an inferiorly-extending keel. D15. The tibial tray of D1 wherein the body comprises a one-piece body.

E1. A method for forming a patient-specific tibial tray for a knee replacement of the patient, the method comprising: determining a patient-specific resected proximal portion of a tibia of the patient, the resected proximal portion of the tibia of the patient having a superior center cancellous bone surface, a peripheral cortical bone surface, and one or more cavities and/or openings in the cancellous bone exposing at least a portion of an underlying inner surface of the cortical bone of the tibia; and forming the patient-specific tibial tray comprising a body having an superior portion having a superior surface and an inferior tibia-engaging portion, the inferior tibia engaging portion having a center portion contactable with the cancellous bone surface, and a peripheral, inferiorly-extending portion receivable in the one or more cavities and/or openings and having one or more surfaces contactable with the exposed underlying inner surface of the cortical bone of the tibia of the patient.

E2. The method of E1 further comprising obtaining first data, via a processor, representing a proximal portion of the tibia of the patient, and determining, via the processor, second data corresponding the patient-specific resected proximal portion of the tibia of the patient based on the first data, and the forming, via the processor, comprises 3D printing, forging, casting based on the second data. E3. The method of E2 wherein the obtaining first data comprises obtaining CT scan data and/or X-rays, and the determining comprises determining the patient-specific resected proximal portion of the tibia of the patient based on the obtained first data. E4. The method of E2 further comprising maximizing the one or more surfaces of the inferior tibia-engaging portion based on a depth and an amount of the surface extending along the perimeter of the underlying inner surface portion of the cortical bone. E5. The method of E2 further comprising reducing shear forces and localized forces based on the implant to bone contact plane based on the equation Fx=Fcos(theta).

As may be recognized by those of ordinary skill in the art based on the teachings herein, numerous changes and modifications may be made to the above-described and other embodiments of the present invention without departing from the scope of the invention. The implants and other components of the devices and/or apparatus as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices and apparatus may include more or fewer components or features than the embodiments as described and illustrated herein. Accordingly, this detailed description of the currently-preferred embodiments is to be taken as illustrative, as opposed to limiting the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general apparatus operation. Modifications and alterations will occur to others upon a reading and understanding of the preceding detailed description. It is intended that the invention be construed as including all such modifications and alterations.

The invention claimed is:

1. A method for forming a patient-specific tibial tray for a total knee replacement of a patient, the method comprising:

obtaining first data, via at least one processor, representing a proximal portion of the tibia of the patient, the first data corresponding to the proximal portion of the tibia of the patient having an inner cancellous bone, and a peripheral cortical bone having an outer surface and an inner surface;

determining, via the at least one processor, second data representing a patient-specific resected proximal portion of the tibia of the patient based on the first data, the resected proximal portion of the tibia of the patient having a center cancellous bone surface, a peripheral cortical bone surface, and at least one cavity formed in the underlying periphery of the resected cancellous bone, the at least one cavity having an outer contoured surface portion corresponding to an adjacent inner surface portion of the resected cortical bone;

forming, via the at least one processor, the tibial tray based on the second data, the patient-specific tibial tray comprising a body having a superior portion having a superior surface and an inferior tibia-engaging portion, the inferior tibia engaging portion having a center portion contactable with the resected center cancellous bone surface, and at least one inferiorly-extending wall receivable in the at least one cavity;

the determining, via the at least one processor, the second data comprises the at least one cavity extending into the resected cancellous bone comprising a first U-shaped cavity and a spaced apart second U-shaped cavity; and the forming, via the at least one processor, the patient-specific tibial tray based on the second data comprises the at least one inferiorly-extending wall comprising a first U-shaped wall and a spaced apart second U-shaped wall receivable in the first U-shaped cavity and the spaced apart second U-shaped cavity, respectively, the first U-shaped wall having:

a first outer wall surface, a first inner wall surface, and a pair of substantially planar first end surfaces connecting between ends of the first outer wall surface and first inner wall surface, the second U-shaped wall having:

a second inner wall surface, a second outer wall surface, and a pair of substantially planar second end surfaces connecting between ends of the second outer wall surface and second inner wall surface, and wherein the pair of first end surfaces of the first U-shaped wall are facing the pair of second end surfaces of said second U-shaped wall.

2. The method of claim 1, wherein:

for the total knee replacement, a greater portion of a shearing force acting transversely on the patient-specific tibial tray and the resected portion of the proximal portion of the tibia of the patient is resistible by the at least one inferiorly-extending wall and the periphery of the resected proximal portion of the tibia compared to a portion of the shearing force being resistible along the center inferior surface of the tibial tray and the resected cancellous bone surface.

3. The method of claim 1, wherein the determining, via the at least one processor, the second data comprises reducing shear forces and localized forces based on an implant to bone contact plane employing the equation Fx=Fcos(theta).

4. The method of claim 1, wherein the forming, via the at least one processor, comprises at least one of 3D printing, forging, or casting, and the obtaining first data comprises obtaining CT scan data and/or X-ray data.

5. The method of claim 1, wherein:

the determining, via the at least one processor, the second data comprises the at least one cavity extending into the resected cancellous bone comprising a C-shaped cavity; and forming, via the at least one processor, the patient-specific tibial tray based on the second data comprises the at least one inferiorly-extending wall comprising a C-shaped wall receivable in the C-shaped cavity.

6. The method of claim 1, wherein:

the determining, via the at least one processor, the second data comprises the at least one cavity extending into the resected cancellous bone comprising a cavity extending continuously around the center cancellous bone surface and adjacent to the inner surface of the underlying cortical bone; and the forming, via the at least one processor, the patient-specific tibial tray based on the second data comprises the at least one inferiorly-extending wall comprising a continuous inferiorly-extending wall receivable in the cavity extending continuously around the center cancellous bone surface and adjacent to the inner surface of the underlying cortical bone.

7. The method of claim 1, wherein:

the determining, via the at least one processor, the second data representing a patient-specific resected proximal portion of the tibia of the patient comprises the at least one cavity having a constant thickness; and the forming, via the at least one processor, the patient-specific tibial tray based on the second data, the patient-specific tibial tray comprising the at least one inferiorly-extending wall having a constant thickness.

8. The method of claim 1, wherein:

the determining, via the at least one processor, the second data representing a resected proximal portion of the tibia of the patient comprises the at least one cavity having a constant thickness between 2 millimeters and 10 millimeters; and the forming, via the at least one processor, the patient-specific tibial tray based on the second data, wherein the patient-specific tibial tray comprises the at least one inferiorly-extending wall having a constant thickness between 2 millimeters and 10 millimeters.

9. The method of claim 1, wherein:

the determining, via the at least one processor, the second data representing a resected proximal portion of the tibia of the patient comprises the at least one cavity having a tapering depth; and the forming, via the at least one processor, the patient-specific tibial tray based on the second data, wherein the patient-specific tibial tray comprises the at least one inferiorly-extending wall having a tapering wall.

10. The method of claim 1, wherein:

the determining, via the at least one processor, the second data comprises the resected center cancellous bone surface having a contoured surface; and the forming, via the at least one processor, the patient-specific tibial tray based on the second data comprises the inferior tibia-engaging portion having a center portion having a contoured surface.

11. The method of claim 1, wherein:

the determining, via the at least one processor, the second data comprises the at least one cavity extending and spaced from the inner surface portion of the underlying cortical bone; and the forming, via the at least one processor, the patient-specific tibial tray based on the second data comprises the at least one inferiorly-extending wall disposable in the resected cancellous bone and spaced from the inner surface portion of the underlying cortical bone.

12. The method of claim 1, wherein:

the determining, via the at least one processor, the second data comprises the at least one cavity extending into the cancellous bone to expose the inner surface portion of underlying cortical bone; and the forming, via the at least one processor, the patient-specific tibial tray based on the second data comprises the at least one inferiorly-extending wall engageable with the exposed inner surface portion of the underlying cortical bone.

13. The method of claim 1, wherein:

the determining, via the at least one processor, the second data comprises the at least one cavity extending into the cancellous bone having an outer inferiorly-extending surface and an inner inferiorly-extending surface terminating at an acute angle in the resected cancellous bone; and the forming, via the at least one processor, the patient-specific tibial tray based on the second data comprises the at least one inferiorly-extending wall having an outer inferiorly-extending surface and the inner inferiorly-extending surface terminating at an acute angle receivable in the at least one cavity extending into the cancellous bone having the outer inferiorly-extending surface and the inner inferiorly-extending surface terminating at an acute angle in the resected cancellous bone.

14. The method of claim 1, wherein:

the determining, via the at least one processor, the second data comprises the at least one cavity extending into the resected cancellous bone having an outer inferiorly-extending surface along a depth that corresponds exactly to the contour of the inner surface of the corresponding adjacent inner surface of underlying cortical bone; and the forming, via the at least one processor, the patient-specific tibial tray based on the second data comprises the at least one inferiorly-extending wall having an outer inferiorly-extending surface that corresponds exactly to the contour of the inner surface of the corresponding adjacent inner surface of the underlying cortical bone.

15. The method of claim 1, wherein:

the determining, via the at least one processor, the second data representing a resected proximal portion of the tibia of the patient based on the first data comprises the resected proximal portion of the tibia of the patient having a center cancellous bone surface with attachment of the anterior cruciate ligament (ACL) and the posterior cruciate ligament (PCL), a peripheral cortical bone surface, and at least one cavity extending into the resected cancellous bone adjacent to the inner surface of the underlying cortical bone; and forming, via the at least one processor, the patient-specific tibial tray based on the second data, the patient-specific tibial tray comprising the body comprising a superior portion, the superior surface having a lateral portion and a spaced apart medial portion, and the inferior tibia-engaging portion, the inferior tibia engaging portion having the center portion contactable with the resected center cancellous bone surface, and the at least one inferiorly-extending wall receivable into the at least one cavity.

16. The method of claim 1, wherein:

the determining, via the at least one processor, the second data comprises the at least one cavity extending into the resected cancellous bone further comprising a first inwardly extending wall cavity and a spaced apart second inwardly-extending wall cavity;

the forming, via the at least one processor, the patient-specific tibial tray based on the second data comprising the at least one inferiorly extending wall further comprises:

a first inwardly-extending wall receivable within the first inwardly-extending wall cavity, the first inwardly-extending wall integrally connected to a one of the pair of first end surfaces of the first U-shaped wall, wherein the first inwardly-extending wall:

extends along a posterior side of the tibial tray, and has a depth that is less than the depth of the first U-shaped wall, and a second inwardly-extending wall receivable within the second inwardly-extending wall cavity, the second inwardly-extending wall integrally connected to a one of the pair of second end surfaces of the second U-shaped wall, wherein the second inwardly-extending wall:

extends along a posterior side of the tibial tray, and has a depth that is less than the depth of the second U-shaped wall; and wherein the first inwardly-extending wall and the second inwardly-extending wall are spaced apart and define a gap disposed along the posterior side of the tibial tray, the gap configured to inhibit the need to sacrifice tendons and ligaments at the posterior side of the resected proximal portion of the tibia.

* * * * *